US011540745B2

(12) United States Patent
Yu et al.

(10) Patent No.: US 11,540,745 B2
(45) Date of Patent: Jan. 3, 2023

(54) CUSTOM PATIENT INTERFACE AND METHODS FOR MAKING SAME

(71) Applicant: ResMed Pty Ltd, Bella Vista (AU)

(72) Inventors: Tzu-Chin Yu, Sydney (AU); Aaron Samuel Davidson, Mona Vale (AU); Robert Henry Frater, Lindfield (AU); Benjamin Peter Johnston, Sydney (AU); Paul Jan Klasek, Bonnyrigg Heights (AU); Robert Anthony Paterson, Sydney (AU); Quangang Yang, Kellyville (AU); Gerard Michael Rummery, Woodford (AU); Priyanshu Gupta, Sydney (AU); Liam Holley, Sydney (AU); Gordon Joseph Malouf, Sydney (AU)

(*) Notice: Subject to any disclaimer, the term of this patent is extended or adjusted under 35 U.S.C. 154(b) by 166 days.

(21) Appl. No.: 16/946,773

(22) Filed: Jul. 6, 2020

(65) Prior Publication Data
US 2021/0008320 A1   Jan. 14, 2021

Related U.S. Application Data

(63) Continuation of application No. 15/312,921, filed as application No. PCT/AU2015/050370 on Jul. 2, 2015, now Pat. No. 10,799,662.
(Continued)

(51) Int. Cl.
*G06K 9/00* (2022.01)
*A61B 5/107* (2006.01)
(Continued)

(52) U.S. Cl.
CPC .......... *A61B 5/107* (2013.01); *A61B 5/1077* (2013.01); *A61B 5/6819* (2013.01);
(Continued)

(58) Field of Classification Search
CPC .......... A61M 16/0616; A61M 16/0683; A61M 16/1055; A61M 16/107; A61M 16/0618;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| CN | 1623609 A | 6/2005 |
| CN | 1688358 A | 10/2005 |

(Continued)

OTHER PUBLICATIONS

CN Office Action issued in corresponding CN application No. 2015800467647 dated Aug. 3, 2018.
(Continued)

*Primary Examiner* — Amir Alavi
(74) *Attorney, Agent, or Firm* — Botos Churchill IP Law LLP

(57) ABSTRACT

A method of manufacturing a patient interface for sealed delivery of a flow of air at a continuously positive pressure with respect to ambient air pressure to an entrance to the patient's airways includes collecting anthropometric data of a patient's face. Anticipated considerations are identified from the collected anthropometric data during use of the patient interface. The collected anthropometric data is processed to provide a transformed data set based on the anticipated considerations, the transformed data set corresponding to at least one customised patient interface component. At least one patient interface component is modeled based on the transformed data set.

22 Claims, 70 Drawing Sheets

Related U.S. Application Data

(60) Provisional application No. 62/067,535, filed on Oct. 23, 2014, provisional application No. 62/020,147, filed on Jul. 2, 2014.

(51) Int. Cl.

| | | |
|---|---|---|
| *A61B 5/00* | (2006.01) | |
| *A61M 16/10* | (2006.01) | |
| *A61M 16/00* | (2006.01) | |
| *A61M 16/16* | (2006.01) | |
| *A61M 16/06* | (2006.01) | |
| *G06T 19/00* | (2011.01) | |
| *G16H 20/40* | (2018.01) | |
| *G16H 40/67* | (2018.01) | |
| *G06T 19/20* | (2011.01) | |
| *G16H 50/50* | (2018.01) | |

(52) U.S. Cl.
CPC ........ *A61M 16/0066* (2013.01); *A61M 16/06* (2013.01); *A61M 16/0683* (2013.01); *A61M 16/0688* (2014.02); *A61M 16/107* (2014.02); *A61M 16/16* (2013.01); *G06T 19/00* (2013.01); *G06T 19/20* (2013.01); *G16H 20/40* (2018.01); *G16H 40/67* (2018.01); *A61M 16/109* (2014.02); *A61M 16/1055* (2013.01); *A61M 16/1095* (2014.02); *A61M 2016/0033* (2013.01); *A61M 2016/0661* (2013.01); *A61M 2205/3368* (2013.01); *A61M 2207/00* (2013.01); *G06T 2210/41* (2013.01); *G16H 50/50* (2018.01); *Y02A 90/10* (2018.01)

(58) Field of Classification Search
CPC ............ A61M 16/161; A61M 16/0622; A61M 16/0666; G06K 9/74; G06K 9/745; G06K 9/82; G06K 9/20; G06T 7/0012; G06T 7/0083; G06T 7/0081; G06T 2207/30004; G06F 19/321

See application file for complete search history.

(56) References Cited

U.S. PATENT DOCUMENTS

| | | | |
|---|---|---|---|
| 5,753,931 A | 5/1998 | Borchers et al. | |
| 5,918,598 A | 7/1999 | Belfer et al. | |
| 6,044,170 A | 3/2000 | Migdal et al. | |
| 6,196,223 B1 | 3/2001 | Belfer et al. | |
| 6,397,847 B1 | 6/2002 | Scarberry et al. | |
| 6,464,924 B1 | 10/2002 | Thornton | |
| 6,532,959 B1 | 3/2003 | Berthon-Jones | |
| 6,581,594 B1 | 6/2003 | Drew et al. | |
| 6,728,589 B1 | 4/2004 | Delache et al. | |
| 6,857,428 B2 | 2/2005 | Thornton | |
| 7,128,069 B2* | 10/2006 | Farrugia | A61B 5/417 128/204.23 |
| 7,243,650 B2 | 7/2007 | Thornton | |
| 7,525,663 B2* | 4/2009 | Kwok | A61M 16/161 128/203.27 |
| 7,658,189 B2* | 2/2010 | Davidson | A61M 16/06 128/207.18 |
| 7,672,973 B2 | 3/2010 | Lordo | |
| 7,726,313 B2 | 6/2010 | Meyer et al. | |
| 7,770,579 B2* | 8/2010 | O'Connor | A61M 16/00 128/204.26 |
| 7,827,038 B2 | 11/2010 | Richard et al. | |
| 7,866,944 B2 | 1/2011 | Barton et al. | |
| 7,904,193 B2 | 3/2011 | Janbakhsh | |
| 7,909,035 B2 | 3/2011 | Thornton | |
| 7,934,501 B2* | 5/2011 | Fu | A61M 16/08 128/205.25 |
| 8,020,276 B2 | 9/2011 | Thornton | |
| 8,236,216 B2 | 8/2012 | Thornton | |
| 8,254,637 B2 | 8/2012 | Abourizk et al. | |
| 8,291,906 B2 | 10/2012 | Kooij et al. | |
| 8,297,285 B2 | 10/2012 | Henry et al. | |
| 8,603,006 B2* | 12/2013 | Mulqueeny | A61B 5/0871 600/533 |
| 8,636,479 B2 | 1/2014 | Barton et al. | |
| 8,638,014 B2 | 1/2014 | David | |
| 8,875,709 B2 | 11/2014 | Davidson et al. | |
| 9,010,330 B2 | 4/2015 | Barlow et al. | |
| 9,108,014 B2 | 8/2015 | Carroll et al. | |
| 9,149,593 B2 | 10/2015 | Dravitzki et al. | |
| 9,427,545 B2 | 8/2016 | Eves et al. | |
| 9,744,324 B2 | 8/2017 | Davidson et al. | |
| 9,889,267 B2 | 2/2018 | Wells et al. | |
| 9,937,312 B2 | 4/2018 | Kwok et al. | |
| 9,981,102 B2* | 5/2018 | Veliss | A61M 16/0616 |
| 10,034,995 B2* | 7/2018 | Kooij | F16L 3/13 |
| 10,420,909 B2* | 9/2019 | Martin | A61M 16/0683 |
| 10,792,450 B2* | 10/2020 | Holley | A61M 16/0605 |
| 10,799,662 B2* | 10/2020 | Yu | A61M 16/107 |
| 2001/0005425 A1 | 6/2001 | Watanabe et al. | |
| 2004/0117165 A1 | 6/2004 | Selim | |
| 2004/0263863 A1 | 12/2004 | Rogers et al. | |
| 2005/0284479 A1 | 12/2005 | Schrader et al. | |
| 2005/0284484 A1 | 12/2005 | Curti et al. | |
| 2006/0005837 A1 | 1/2006 | Thornton | |
| 2006/0023228 A1 | 2/2006 | Geng | |
| 2006/0185673 A1 | 8/2006 | Critzer et al. | |
| 2008/0060652 A1 | 3/2008 | Selvarajan et al. | |
| 2008/0078396 A1 | 4/2008 | Janbakhsh | |
| 2008/0083412 A1 | 4/2008 | Henry et al. | |
| 2008/0021289 A1 | 9/2008 | Ramazan et al. | |
| 2009/0044808 A1 | 2/2009 | Guney et al. | |
| 2009/0050156 A1 | 2/2009 | Ng et al. | |
| 2009/0266362 A1 | 10/2009 | Mark | |
| 2010/0000534 A1 | 1/2010 | Kooij et al. | |
| 2011/0088699 A1 | 4/2011 | Skipper et al. | |
| 2012/0305003 A1 | 12/2012 | Mark | |
| 2015/0352306 A1* | 12/2015 | Scheiner | A61M 16/0672 128/205.25 |
| 2016/0082214 A1 | 3/2016 | Barlow et al. | |
| 2016/0250434 A1* | 9/2016 | Asvadi | A61M 16/0057 128/205.25 |
| 2017/0326320 A1 | 11/2017 | Baigent et al. | |

FOREIGN PATENT DOCUMENTS

| | | |
|---|---|---|
| DE | 10138416 A1 | 2/2003 |
| EP | 2460435 A1 | 6/2012 |
| EP | 1116492 B1 | 5/2017 |
| FR | 2824739 B1 | 4/2004 |
| JP | 2008501375 A | 1/2008 |
| JP | 2010131091 A | 6/2010 |
| WO | 1998004310 A1 | 2/1998 |
| WO | 1998034665 A1 | 8/1998 |
| WO | 200050121 A1 | 8/2000 |
| WO | 2000059567 A1 | 10/2000 |
| WO | 2000078381 | 12/2000 |
| WO | 2004073778 A1 | 9/2004 |
| WO | 2005063328 A1 | 7/2005 |
| WO | 2005118041 A1 | 12/2005 |
| WO | 2006074513 A1 | 7/2006 |
| WO | 2006130903 A1 | 12/2006 |
| WO | 2009052560 A1 | 4/2009 |
| WO | 2009063402 A1 | 5/2009 |
| WO | 2009066202 A2 | 5/2009 |
| WO | 2010066004 A1 | 6/2010 |
| WO | 2010135785 A1 | 12/2010 |
| WO | 2012045127 A1 | 4/2012 |
| WO | 2013020167 A1 | 2/2013 |
| WO | 2013068950 A1 | 5/2013 |
| WO | 2013072823 A1 | 5/2013 |
| WO | 2013088293 A1 | 6/2013 |
| WO | 2013136246 A1 | 9/2013 |
| WO | 2013144797 A1 | 10/2013 |
| WO | 2014015382 A1 | 1/2014 |
| WO | 2014024086 A1 | 2/2014 |

(56) References Cited

FOREIGN PATENT DOCUMENTS

| WO | 2014057392 A1 | 4/2014 |
| WO | 2014053966 A3 | 5/2014 |
| WO | 2014075797 A1 | 5/2014 |

OTHER PUBLICATIONS

EP Search Report to EP Application No. 15815762.8.
International Search Report and Written Opinion for Application No. PCT/AU2015/050370 dated Nov. 2, 2015.
Written Opinion for Application No. PCT/AU2015/050370 dated Mar. 15, 2016.
West, John B, "Respiratory Physiology", Lippincott Williams & Wilkins, 9th edition published 2011.
Office Action for New Zealand Patent Application No. 727827, dated May 3, 2021.
The Extended European Search Report for European Patent Application No. 21162413.5, dated Oct. 5, 2021.
Examination Report for New Zealand Application No. 765662, dated Nov. 29, 2021.
First Chinese Office Action for Chinese Patent Application No. 201911082917.X, dated Jan. 13, 2022.
Notice of Reasons for Refusal for Japanese Patent Application No. 2020-126698, dated Mar. 8, 2022.

\* cited by examiner

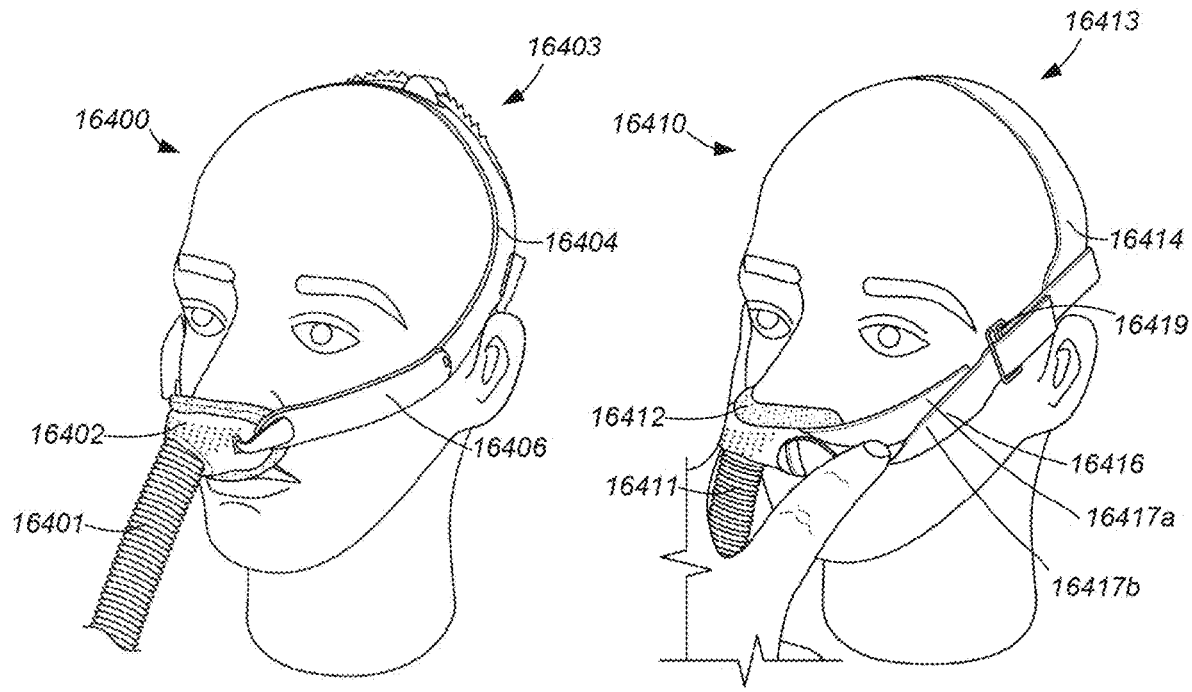
FIG. 16H
FIG. 16I
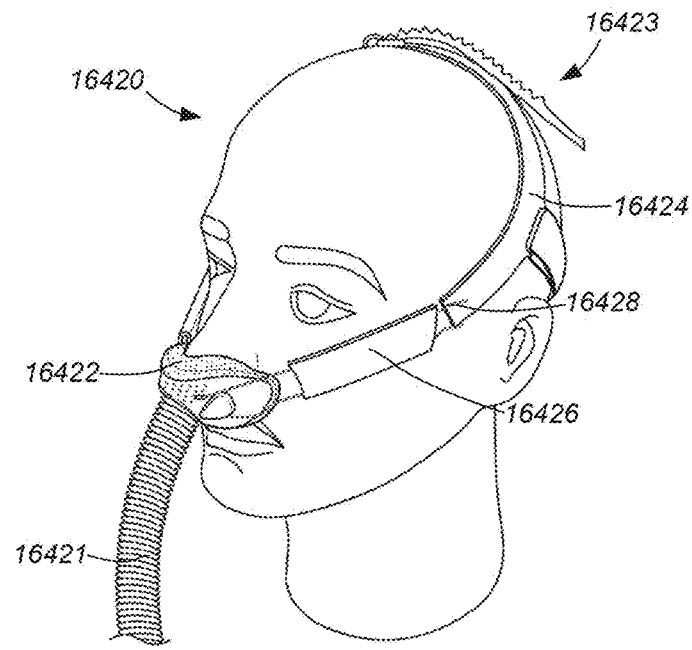
FIG. 16J

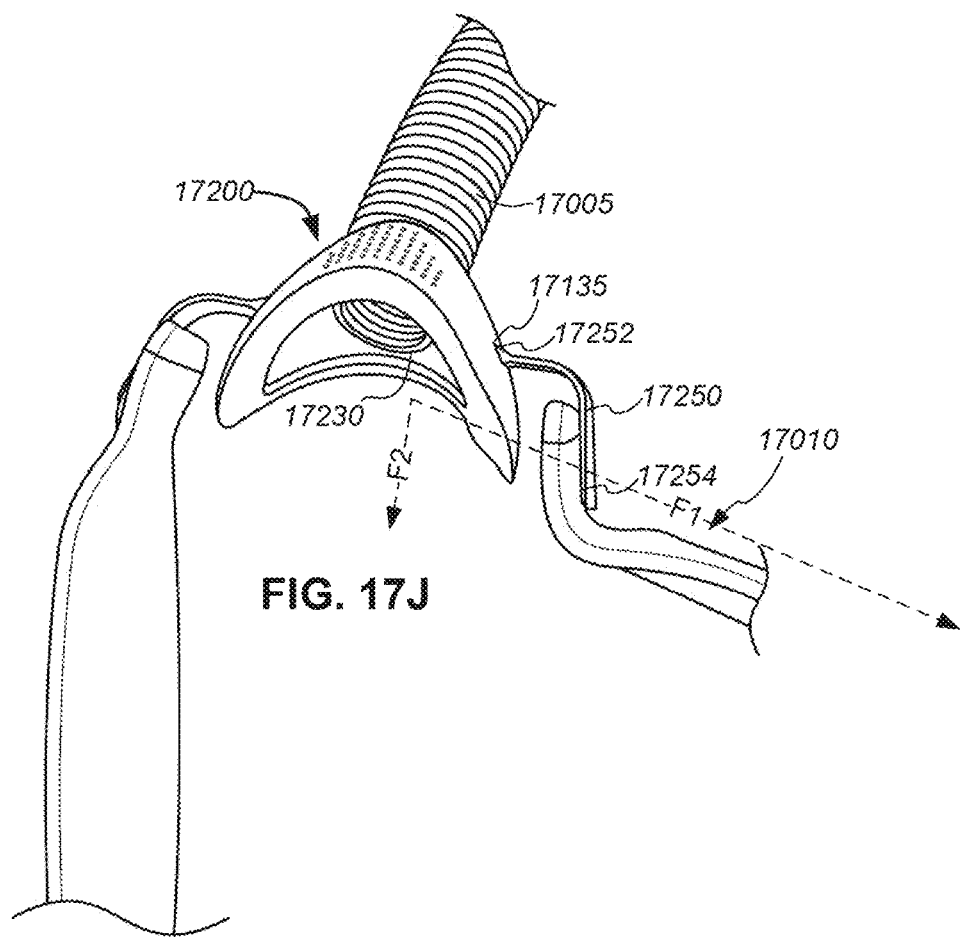

CUSTOM PATIENT INTERFACE AND METHODS FOR MAKING SAME

CROSS-REFERENCE TO RELATED APPLICATIONS

This application is a continuation of U.S. patent application Ser. No. 15/312,921 filed Nov. 21, 2016 which is a national phase entry under 35 U.S.C. § 371 of International Application No. PCT/AU2015/050370 filed Jul. 2, 2015, published in English, which claims priority from U.S. Provisional Patent Application No. 62/067,535 filed Oct. 23, 2014 and U.S. Provisional Patent Application No. 62/020,147 filed Jul. 2, 2014, all of which are incorporated herein by reference.

BACKGROUND OF THE TECHNOLOGY

1.1 Field of the Technology

The present technology relates to one or more of the detection, diagnosis, treatment, prevention and amelioration of respiratory-related disorders. In particular, the present technology relates to medical devices or apparatus, and their use.

Description of the Related Art 1.1.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.1.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.1.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

1.1.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g. several hours. This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

1.1.3.1.1 Seal-Forming Portion

Patient interfaces may include a seal-forming portion (also referred to herein as a sealing element). Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fits and is comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may unintentionally leak. Furthermore, if the shape of the seal-forming portion does not match that of the patient, it may crease or buckle in use, giving rise to unintentional leaks.

Another type of seal-forming portion may comprise a friction-fit element, e.g. for insertion into a naris, however some patients find these uncomfortable.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and LIBERTY™ full-face mask. The following patent applications, assigned to ResMed Limited, describe nasal pillows masks: International Patent Application WO2004/073,778 (describing amongst other things aspects of ResMed SWIFT™ nasal pillows), US Patent Application 2009/0044808 (describing amongst other things aspects of ResMed SWIFT™ LT nasal pillows); International Patent Applications WO 2005/063,328 and WO 2006/130,903 (describing amongst other things aspects of ResMed LIBERTY™ full-face mask); International Patent Application WO 2009/052,560 (describing amongst other things aspects of ResMed SWIFT™ FX nasal pillows).

1.1.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However the use of adhesives may be uncomfortable for some.

Another technique is the use of one or more straps and stabilising harnesses. Many such harnesses suffer from being one or more of ill-fitting, bulky, uncomfortable and awkward to use.

1.1.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Others may be noisy. Many such vents may become blocked in use and thus provide insufficient washout. Some vents may be disruptive of the sleep of a bed-partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

| Table of noise of prior masks (ISO 17510-2: 2007, 10 cmH2O pressure at 1 m) | | | | |
|---|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

| Object | A-weighted sound pressure dB(A) | Notes |
|---|---|---|
| Vacuum cleaner: Nilfisk Walter Broadly Litter Hog: B + Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

(*) one specimen only, measured using test method specified in ISO3744 in CPAP mode at 10 cmH2O)Sound pressure values of a variety of objects are listed below

1.1.3.1.4 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cmH2O).

| RPT Device name | A-weighted sound power level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

1.1.3.1.5 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfill the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.1.3.1.6 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.1.3.1.7 Monitoring Systems

Polysomnography (PSG) is a conventional system for diagnosis and prognosis of cardio-pulmonary disorders. PSG typically involves the placement of 15 to 20 contact sensors on a person in order to record various bodily signals such as electroencephalography (EEG), electrocardiography (ECG), electrooculograpy (EOG), etc. However, while they may be suitable for their usual application in a clinical setting, such systems are complicated and potentially expensive, and/or may be uncomfortable or impractical for a patient at home trying to sleep.

The designer of a device may be presented with an infinite number of choices to make to design a product or system. Design criteria often conflict, meaning that certain design choices are far from routine or inevitable. Furthermore, the comfort and efficacy of certain aspects may be highly sensitive to small, subtle changes in one or more parameters.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance with respiratory therapy.

One form of the present technology comprises customisation of certain elements of a patient interface.

Another aspect of one form of the present technology is the optimisation of a patient interface based on collected data from a patient.

Another aspect of one form of the present technology is the modification of at least one of a frame, an intermediate structure, a sealing element or a headgear of a patient interface.

Another aspect of one form of the present technology is manufacture of comfortable patient interfaces having superior sealing that are more likely to be worn by the user to follow a prescribed therapeutic plan.

Another aspect of one form of the present technology is a patient interface that is moulded or otherwise constructed with a clearly defined perimeter shape which is intended to complement that of an intended wearer.

An aspect of one form of the present technology is a method of manufacturing apparatus.

An aspect of one form of the present technology is a portable RPT device that may be carried by a person, e.g. around the home of the person.

An aspect of one form of the present technology is a patient interface that may be washed in a home of a patient, e.g. in soapy water, without requiring specialised cleaning equipment. An aspect of one form of the present technology is a humidifier tank that may be washed in a home of a patient, e.g. in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:

FIGS. 16H-J are several embodiments of positioning and stabilising structures for compensating for skin changes;

FIGS. 17G-2 illustrates a truncated cone for approximating the dead space of a plenum chamber;

FIG. 17J illustrates the addition of headgear to the frame of FIGS. 17F-I;

2 DETAILED DESCRIPTION OF EXAMPLES OF THE TECHNOLOGY

Before the present technology is described in further detail, it is to be understood that the technology is not limited to the particular examples described herein, which may vary.

It is also to be understood that the terminology used in this disclosure is for the purpose of describing only the particular examples discussed herein, and is not intended to be limiting.

2.1 Treatment Systems

In one form, the present technology comprises an apparatus or device for treating a respiratory disorder. The apparatus or device may comprise a RPT device 1500 for supplying pressurised respiratory gas, such as air, to the patient 1000 via an air circuit 1600 to a patient interface 3000.

Figure 1A:
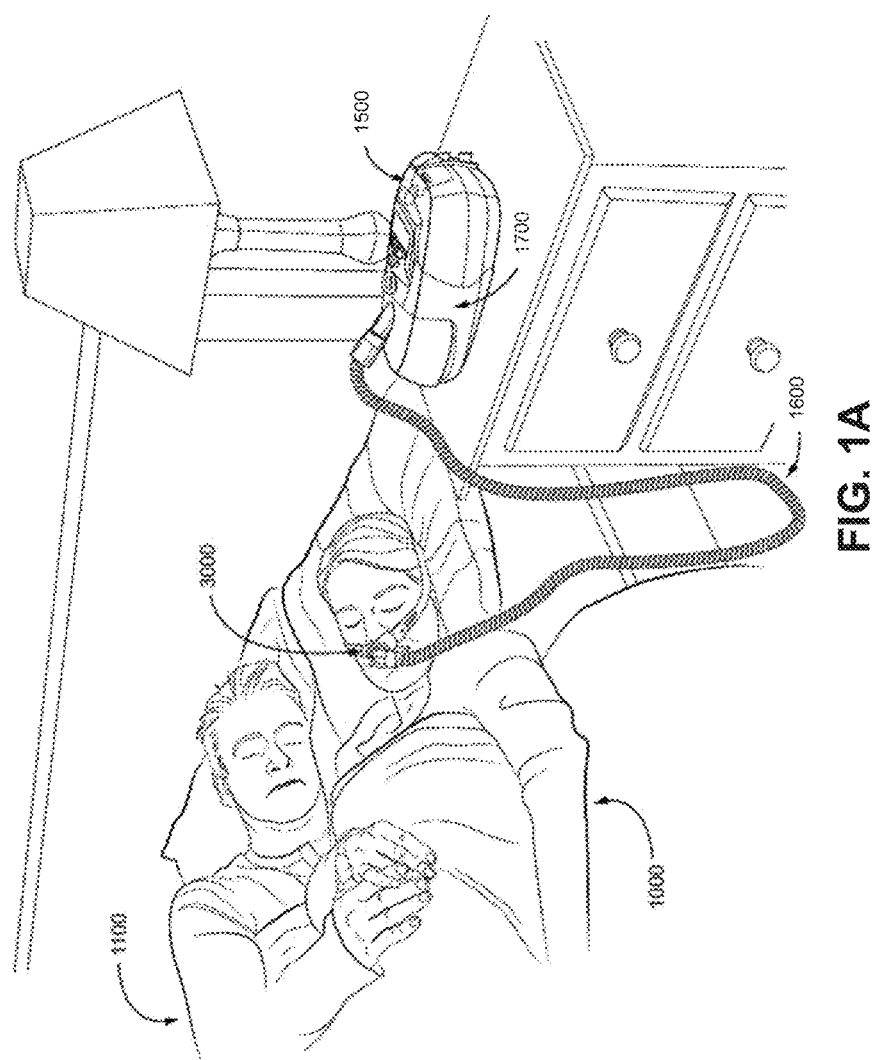
FIG. 1A shows a system including a patient wearing a patient interface in the form of a nasal pillow.

FIG. 1A shows a system including a patient 1000 wearing a patient interface 3000, in the form of a nasal pillows, receives a supply of air at positive pressure from a RPT device 1500. Air from the RPT device is humidified in a humidifier 1700, and passes along an air circuit 1600 to the patient 1000. A bed partner 1100 is also shown.

Figure 1B:
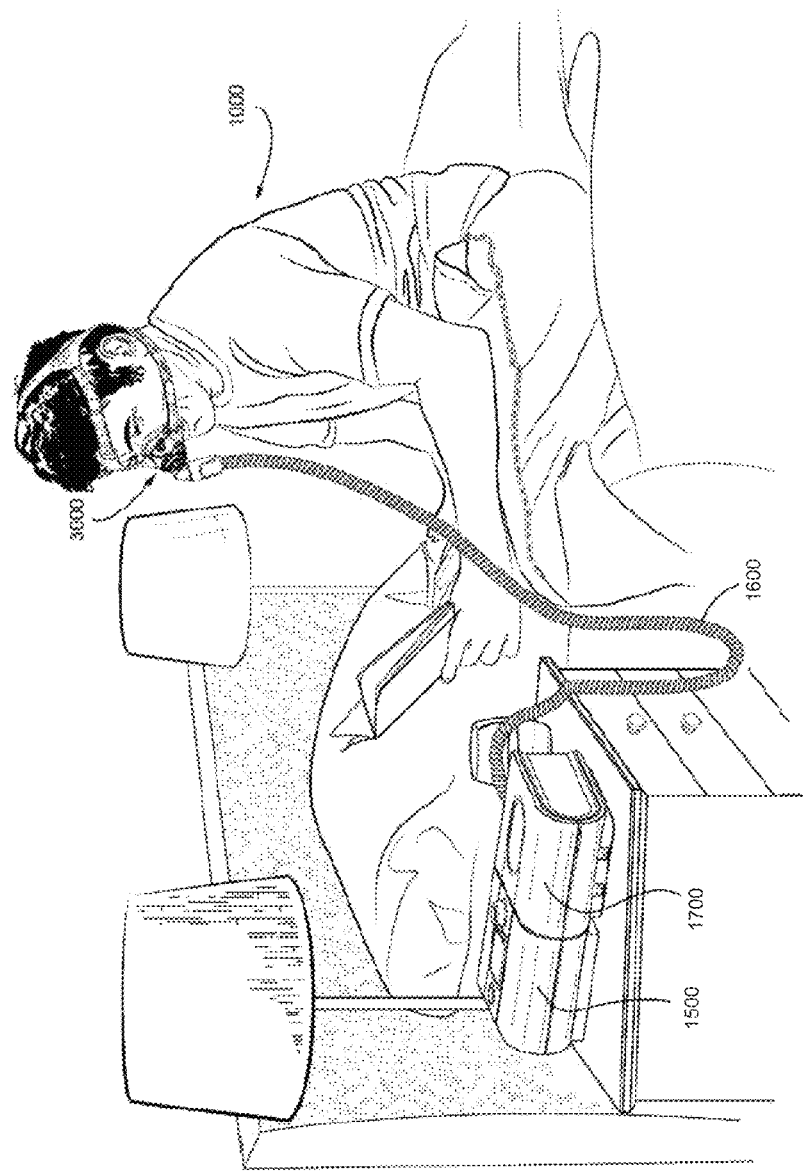
FIG. 1B shows a system including a patient wearing a patient interface in the form of a nasal mask.

FIG. 1B shows a system including a patient 1000 wearing a patient interface 3000, in the form of a nasal mask, receives a supply of air at positive pressure from a RPT device 1500. Air from the RPT device is humidified in a humidifier 1700, and passes along an air circuit 1600 to the patient 1000.

Figure 1C:
FIG. 1C shows a system including a patient wearing a patient interface in the form of a full face mask.
Figure 1D:
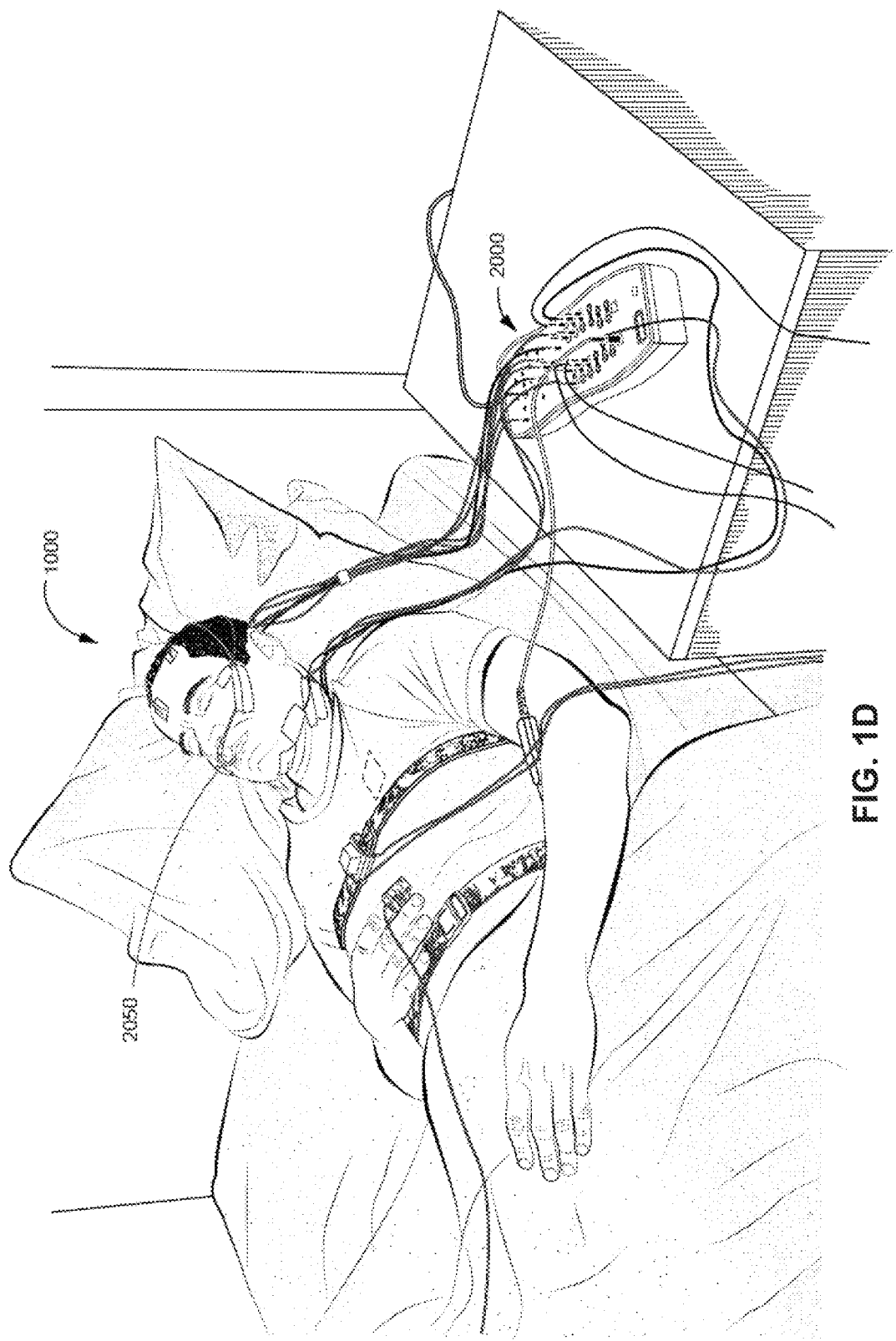
FIG. 1D shows a patient 1000 undergoing polysomnography (PSG)

FIG. 1C shows a system including a patient 1000 wearing a patient interface 3000, in the form of a full-face mask, receives a supply of air at positive pressure from a RPT device 1500. Air from the RPT device is humidified in a humidifier 1700, and passes along an air circuit 1600 to the patient 1000.

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

2.2 Respiratory System and Facial Anatomy

Figure 2A:
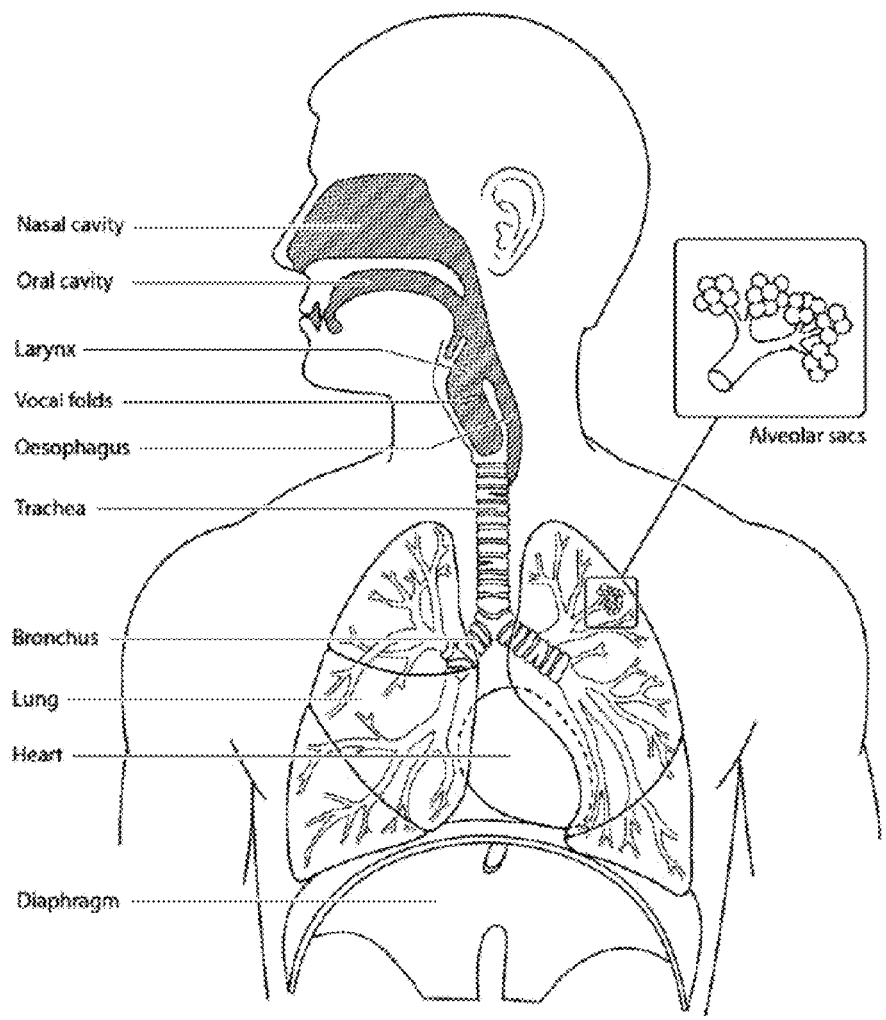
FIG. 2A shows an overview of a human respiratory system.

FIG. 2A shows an overview of a human respiratory system including the nasal and oral cavities, the larynx, vocal folds, oesophagus, trachea, bronchus, lung, alveolar sacs, heart and diaphragm.

Figure 2B:
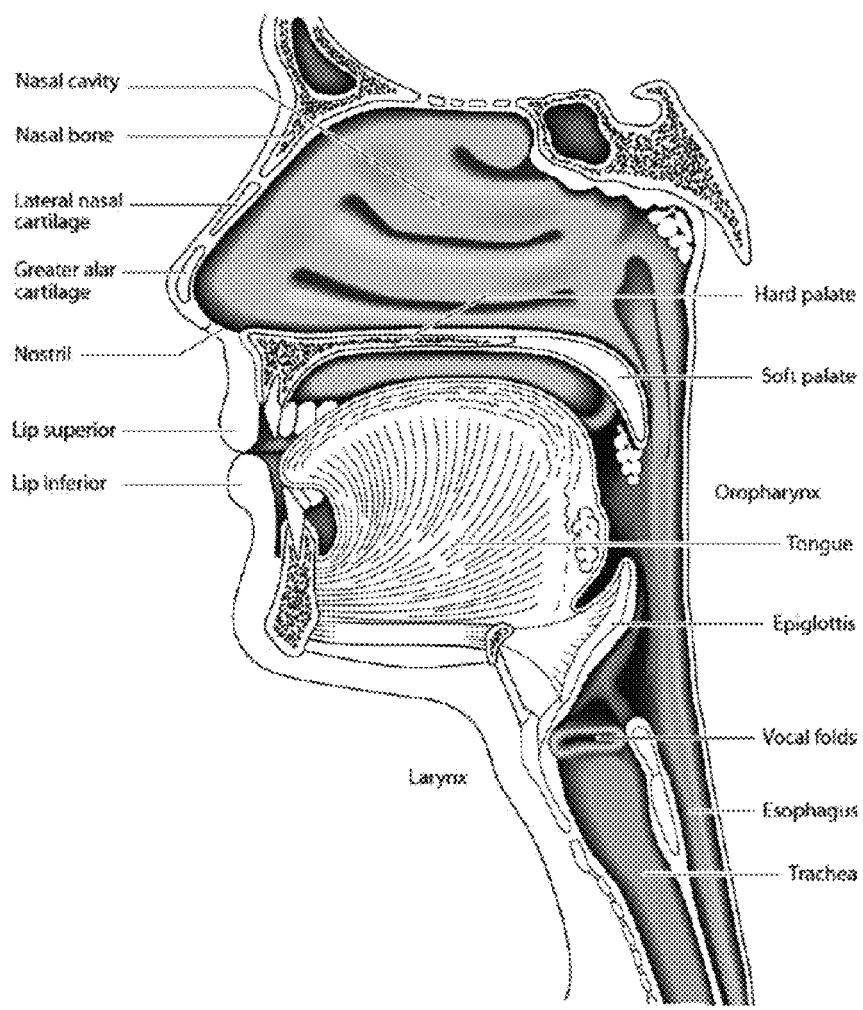
FIG. 2B is a schematic diagram of a human upper airway.

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
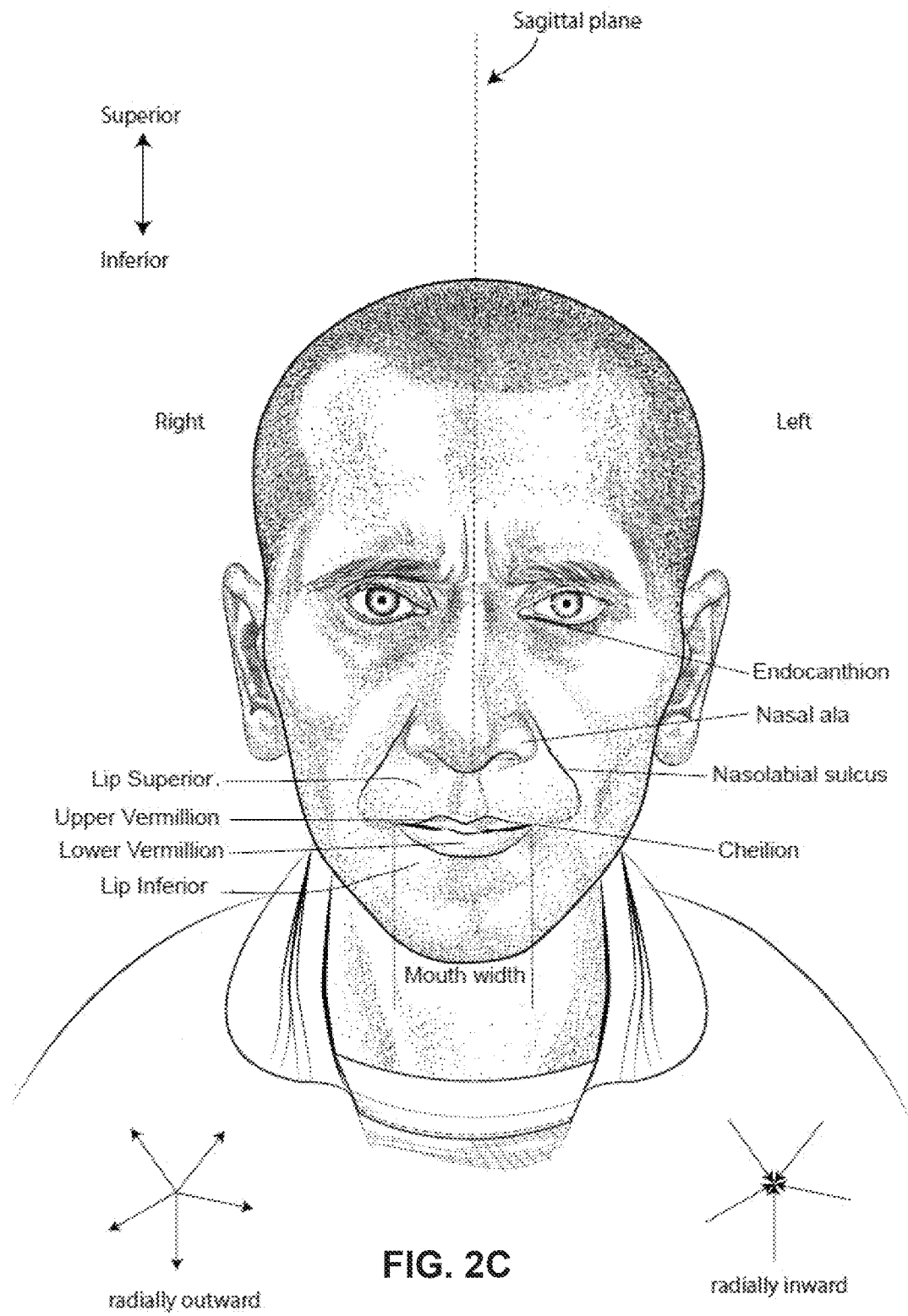
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
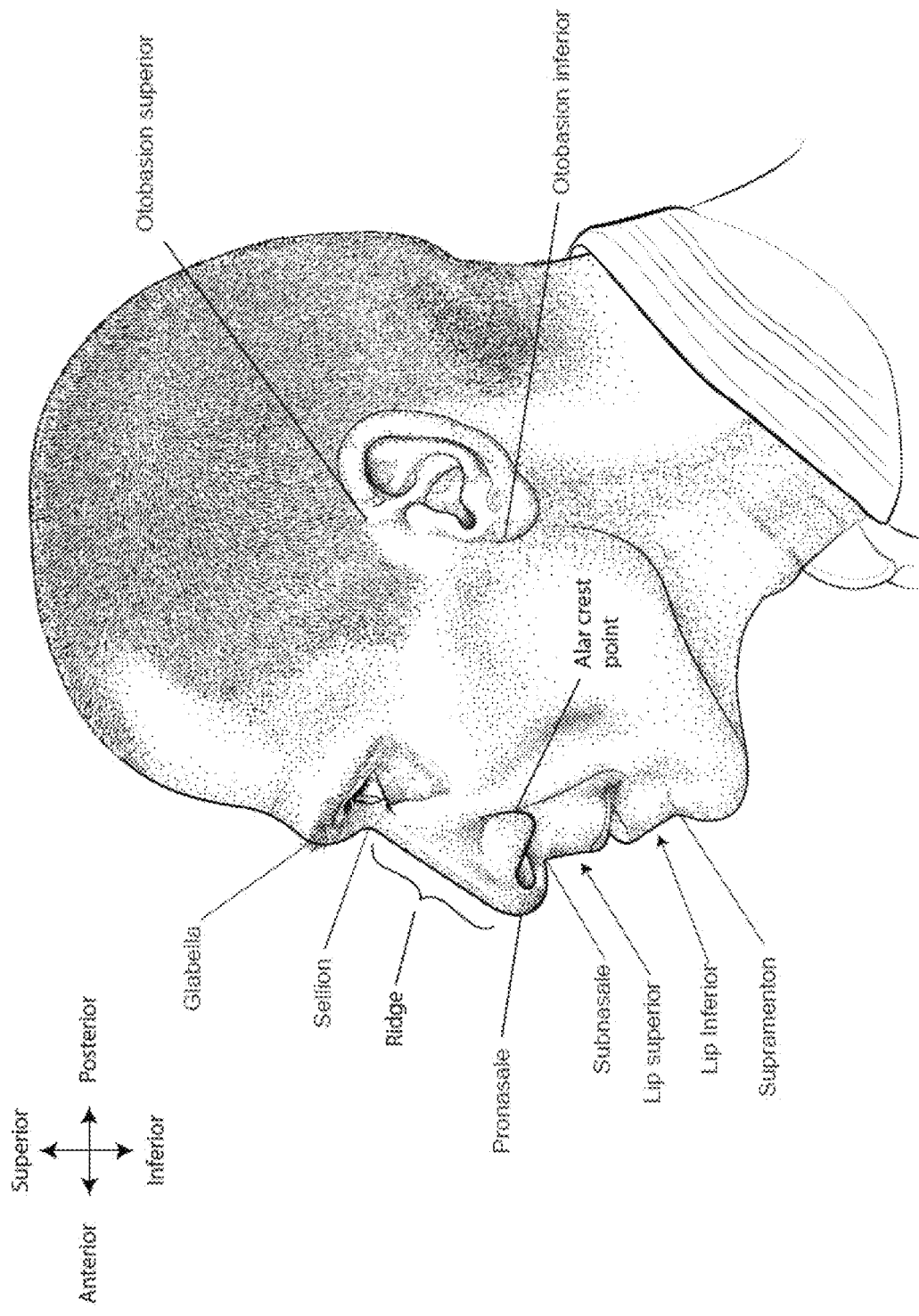
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
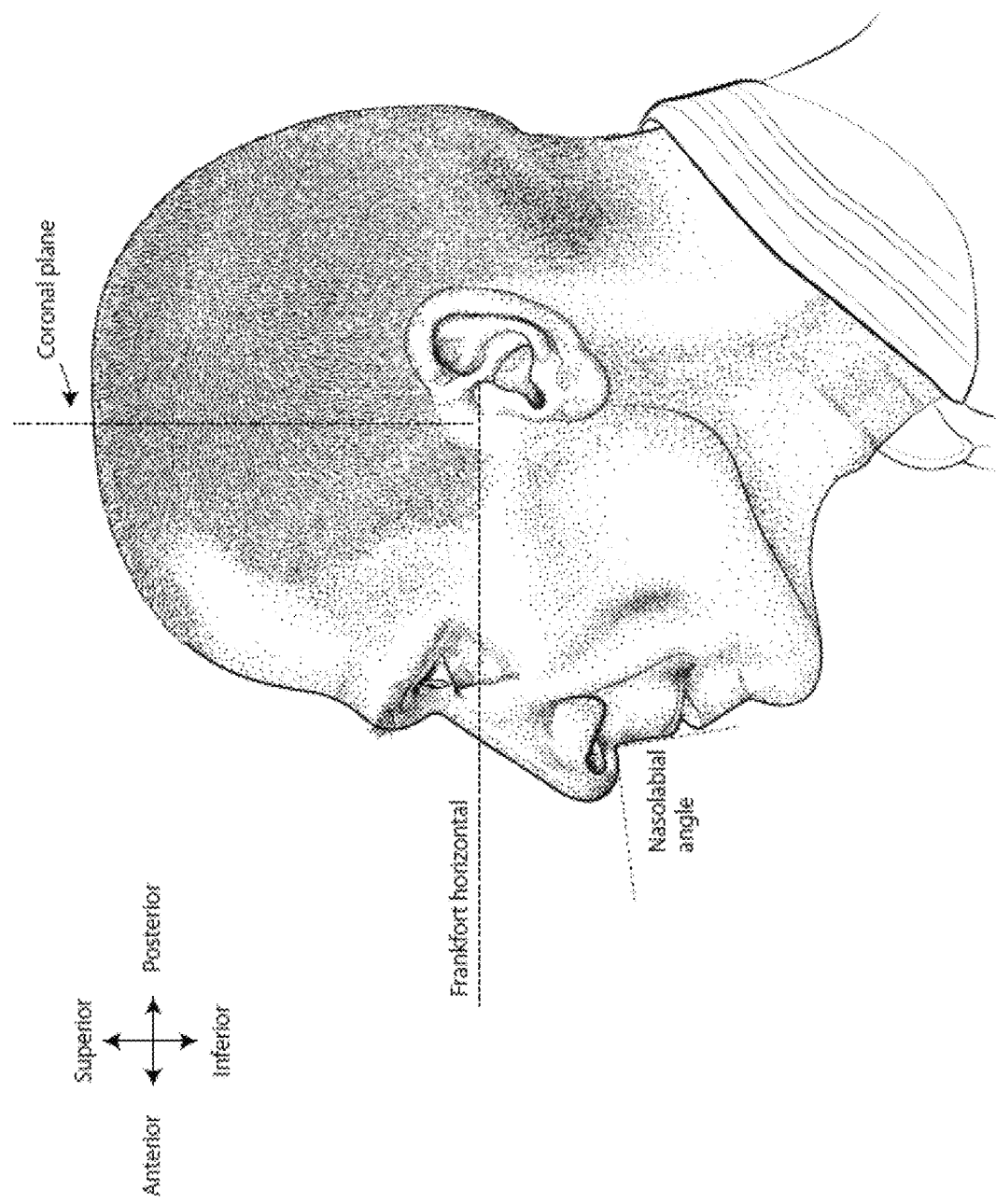
FIG. 2E is a further side view of a head. The approximate locations of the Frankfort horizontal and nasolabial angle are indicated. The coronal plane is also indicated.

FIG. 2E is a further side view of a head. The approximate locations of the Frankfort horizontal and nasolabial angle are indicated. The coronal plane is also indicated.

Figure 2F:
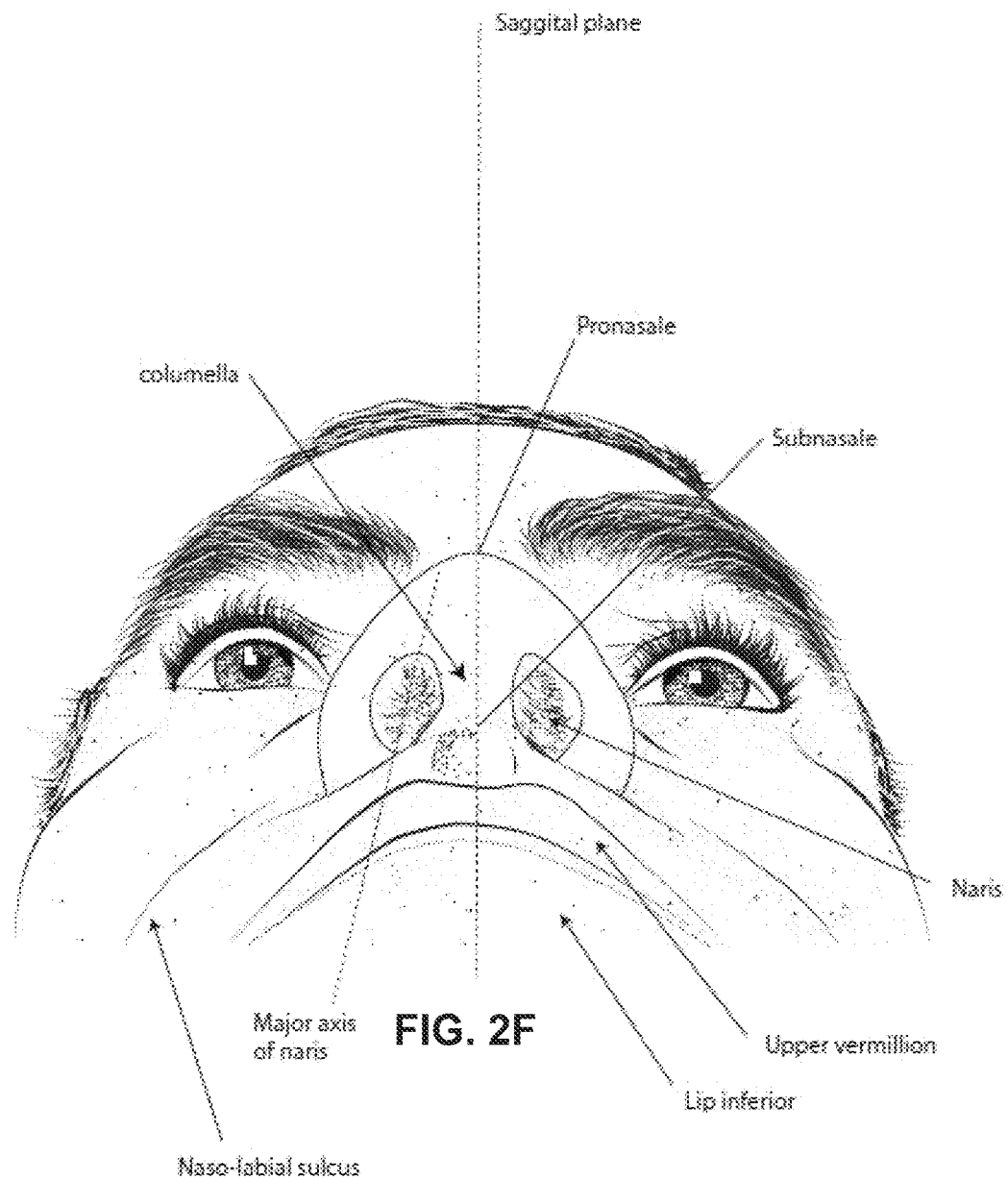
FIG. 2F shows a base view of a nose with several features identified including naso-labial sulcus, lip inferior, upper Vermilion, naris, subnasale, columella, pronasale, the major axis of a naris and the sagittal plane.

FIG. 2F shows a base view of a nose with several features identified including naso-labial sulcus, lip inferior, upper Vermilion, naris, subnasale, columella, pronasale, the major axis of a naris and the sagittal plane.

Figure 2I:
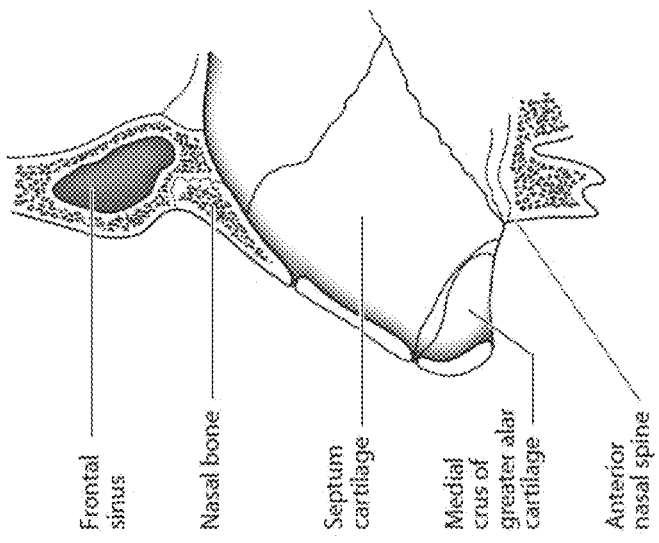
FIG. 2I shows a medial dissection of a nose, approximately several millimeters from a sagittal plane, amongst other things showing the septum cartilage and medial crus of greater alar cartilage.
Figure 2H:
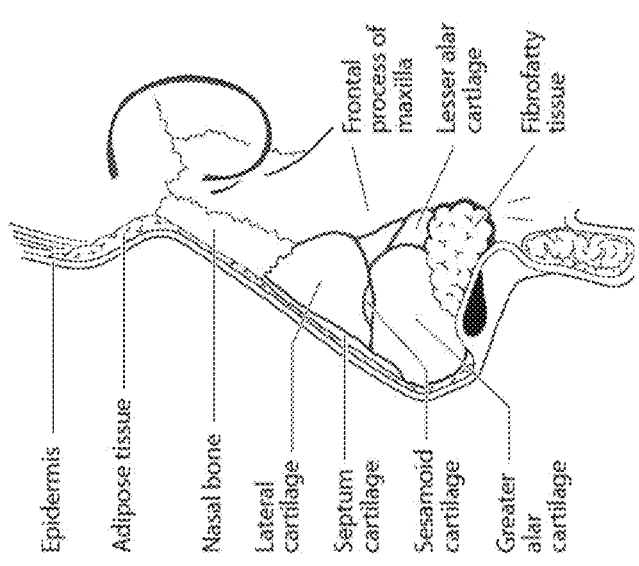
FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.
Figure 2G:
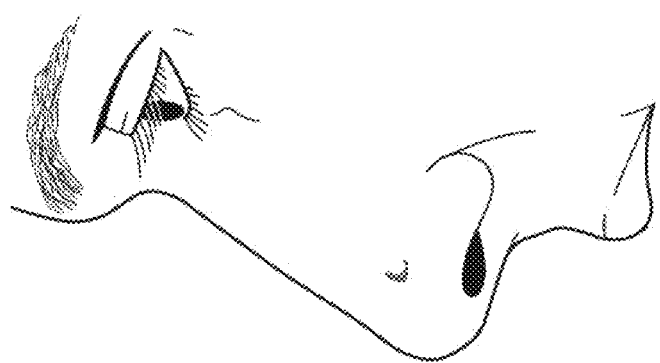
FIG. 2G shows a side view of the superficial features of a nose.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
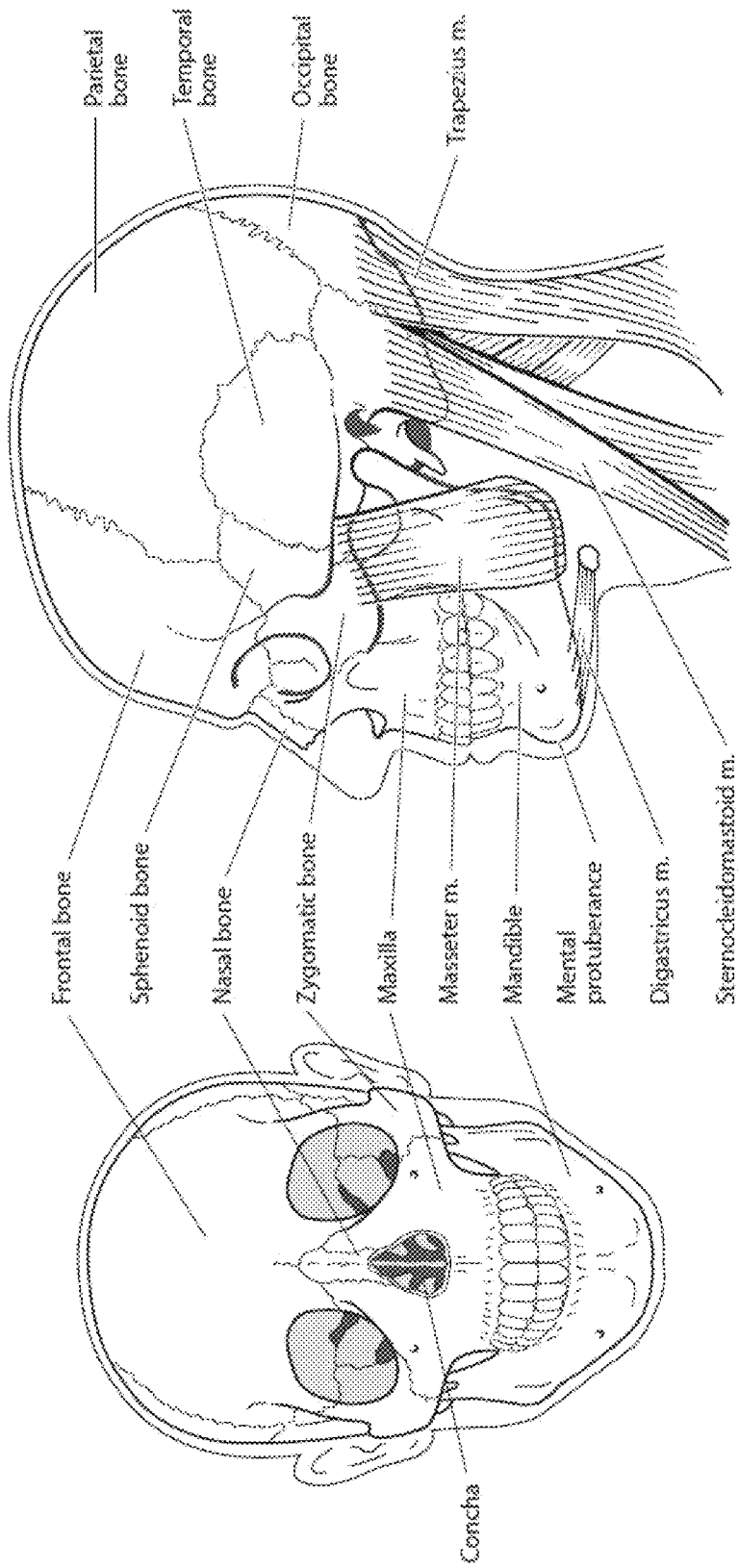
FIG. 2J shows a front view of the bones of a skull including the frontal, nasal and zygomatic bones. Nasal concha are indicated, as are the maxilla, and mandible.
FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
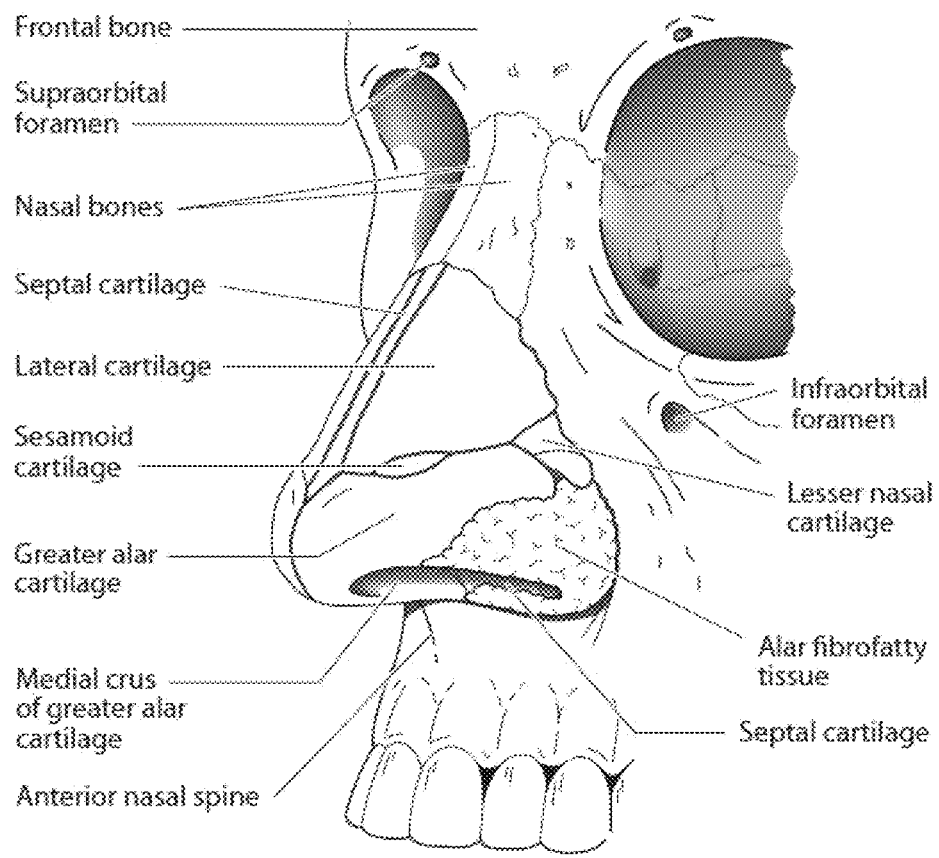
FIG. 2L shows an anterolateral view of a nose.

FIG. 2L shows an anterolateral view of a nose.

2.3 Patient Interface

Figure 3A:
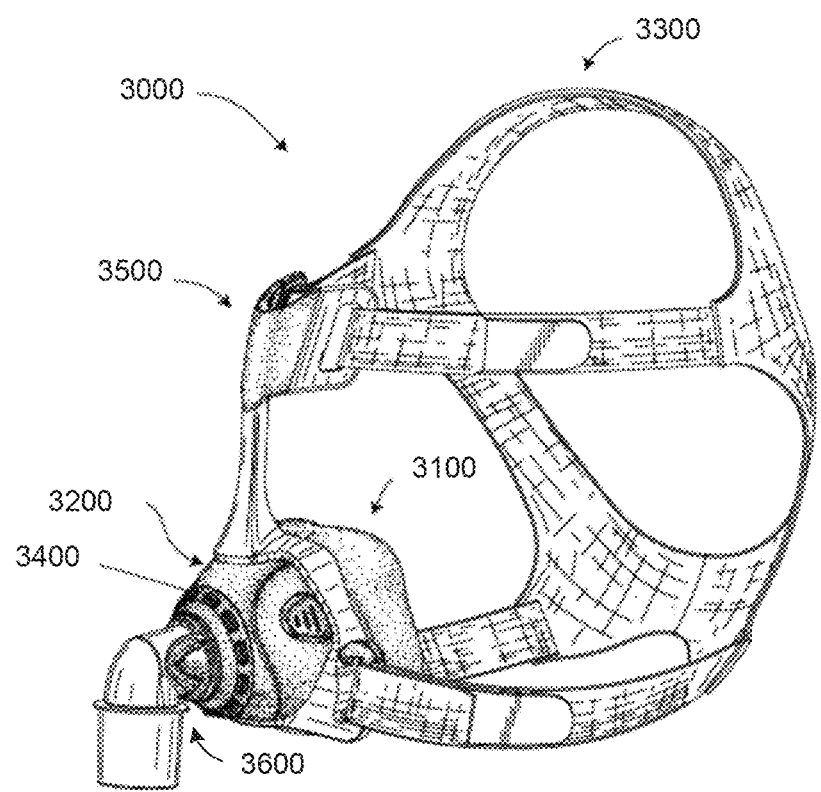
FIG. 3A shows a patient interface in the form of a nasal mask in accordance with one form of the present technology.
Figure 3B:
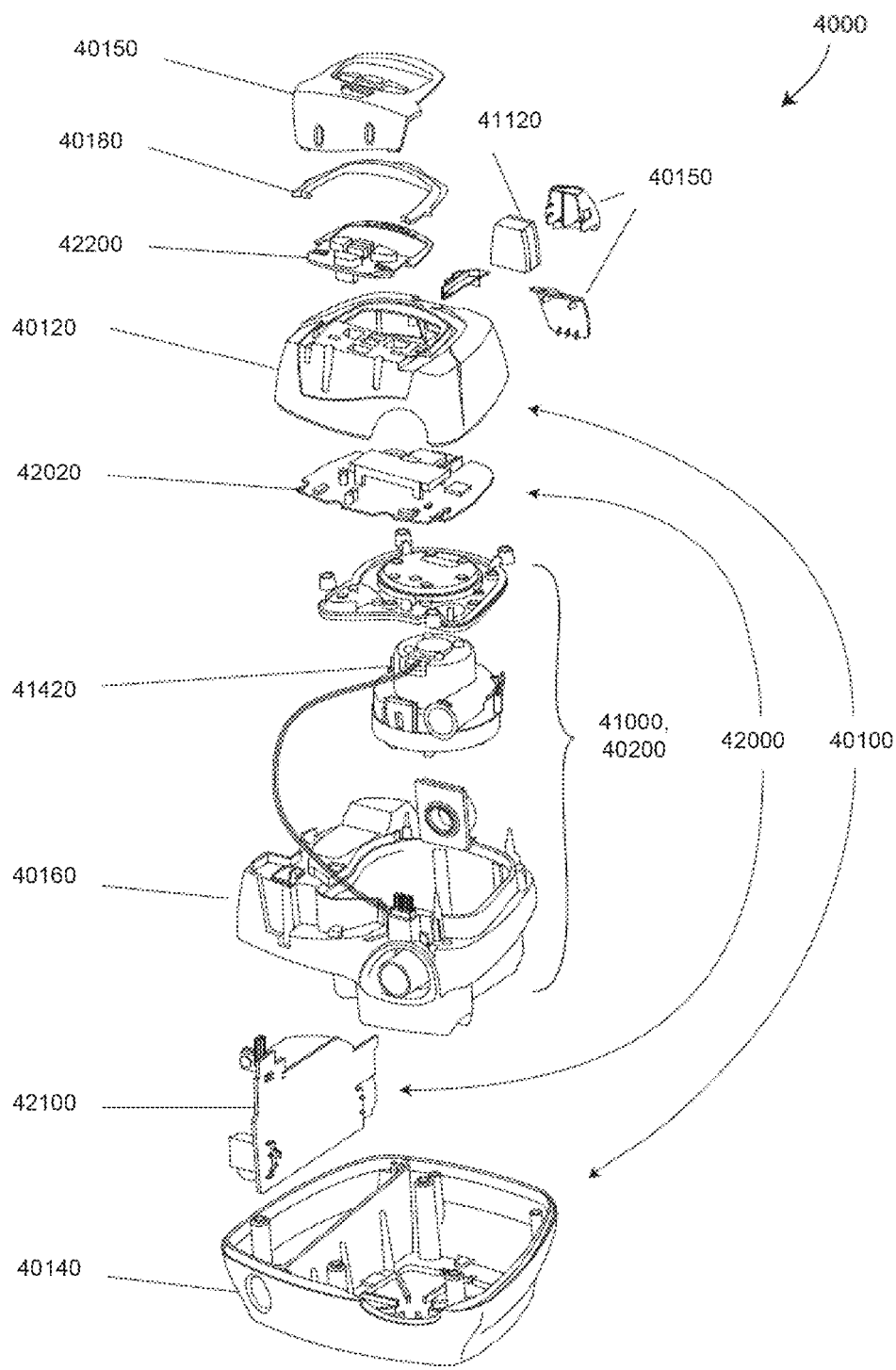
FIG. 3B shows an RPT device in accordance with one form of the present technology.

FIG. 3A shows a patient interface in the form of a nasal mask in accordance with one form of the present technology. A non-invasive patient interface 3000 in accordance with one aspect of the present technology comprises the following functional aspects: a seal-forming structure 3100 (also referred to as a sealing element), a plenum chamber 3200, a positioning and stabilising structure 3300 and one form of connection port 3600 for connection to air circuit 1600. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

2.3.1 Seal-Forming Structure 3100

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

2.3.2 Plenum Chamber 3200

Preferably the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter of the plenum chamber 3200.

2.3.3 Positioning and Stabilising Structure 3300

Preferably the seal-forming structure 3100 of the patient interface 3000 of the present technology is held in sealing position in use by the positioning and stabilising structure 3300, commonly referred to as headgear.

2.3.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes. In some examples, the vent 3400 is located in the plenum chamber 3200.

2.3.5 Forehead Support 3500

In one form, the patient interface 3000 includes a forehead support 3500.

2.3.6 Decoupling Structure(s)

In one form the patient interface 3000 includes at least one decoupling structure, for example, a swivel 3510 or a ball and socket 3520.

2.3.7 Connection Port 3600

Connection port 3600 allows for connection to the air circuit 1600.

2.3.8 Anti-Asphyxia Valve

In one form, the patient interface 3000 includes an anti-asphyxia valve 3800.

2.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

2.4 RPT Device

An RPT device 40000 in accordance with one aspect of the present technology comprises mechanical and pneumatic components 41000, electrical components 42000 and is configured to execute one or more algorithms 43000. The RPT device may have an external housing 40100, formed in two parts, an upper portion 40120 and a lower portion 40140. Furthermore, the external housing 40100 may include one or more panel(s) 40150. The RPT device 40000 comprises a chassis 40160 that supports one or more internal components of the RPT device 40000. The RPT device 40000 may include a handle 40180.

The pneumatic path of the RPT device 40000 may comprise one or more air path items, e.g., an inlet air filter 41120, an inlet muffler 41220, a pressure generator 41400 capable of supplying air at positive pressure (e.g., a blower 41420), an outlet muffler 41240 and one or more transducers 42700, such as pressure sensors 42720 and flow rate sensors 42740.

One or more of the air path items may be located within a removable unitary structure which will be referred to as a pneumatic block 40200. The pneumatic block 40200 may be located within the external housing 40100. In one form a pneumatic block 40200 is supported by, or formed as part of the chassis 40160.

The RPT device 40000 may have an electrical power supply 42100, one or more input devices 42200, a central controller 42300, a therapy device controller 42400, a pressure generator 41400, one or more protection circuits 42500, memory 42600, transducers 42700, data communication interface 42800 and one or more output devices 42900. Electrical components 42000 may be mounted on a single Printed Circuit Board Assembly (PCBA) 42020. In an alternative form, the RPT device 40000 may include more than one PCBA 42020.

2.4.1 RPT Device Mechanical & Pneumatic Components

An RPT device may comprise one or more of the following components in an integral unit. In an alternative form, one or more of the following components may be located as respective separate units.

2.4.1.1 Air Filter(s)

An RPT device in accordance with one form of the present technology may include an air filter 41100, or a plurality of air filters 41100.

Figure 3C:
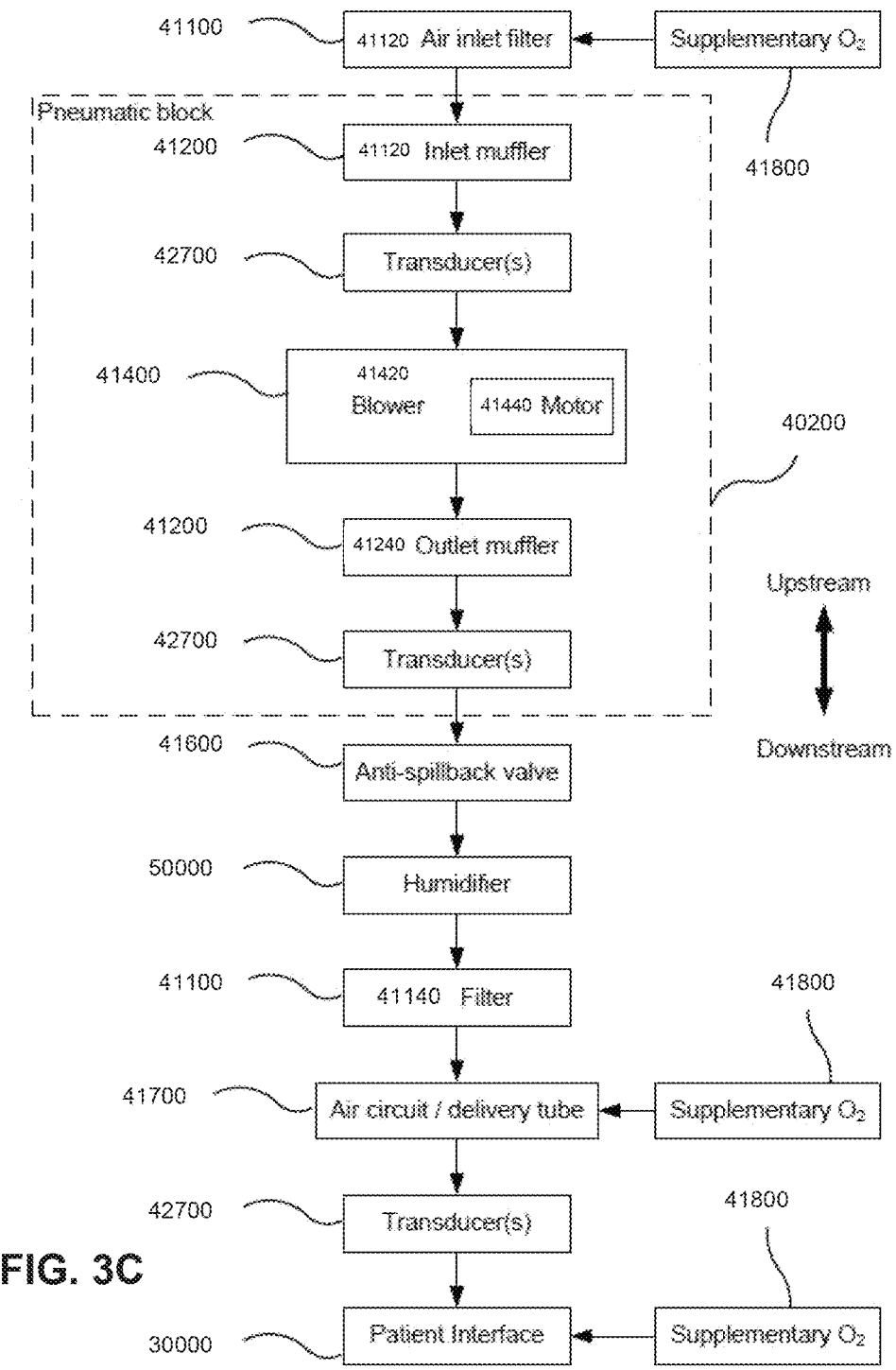
FIG. 3C is a schematic diagram of the pneumatic path of an RPT device in accordance with one form of the present technology. The directions of upstream and downstream are indicated.
Figure 3D:
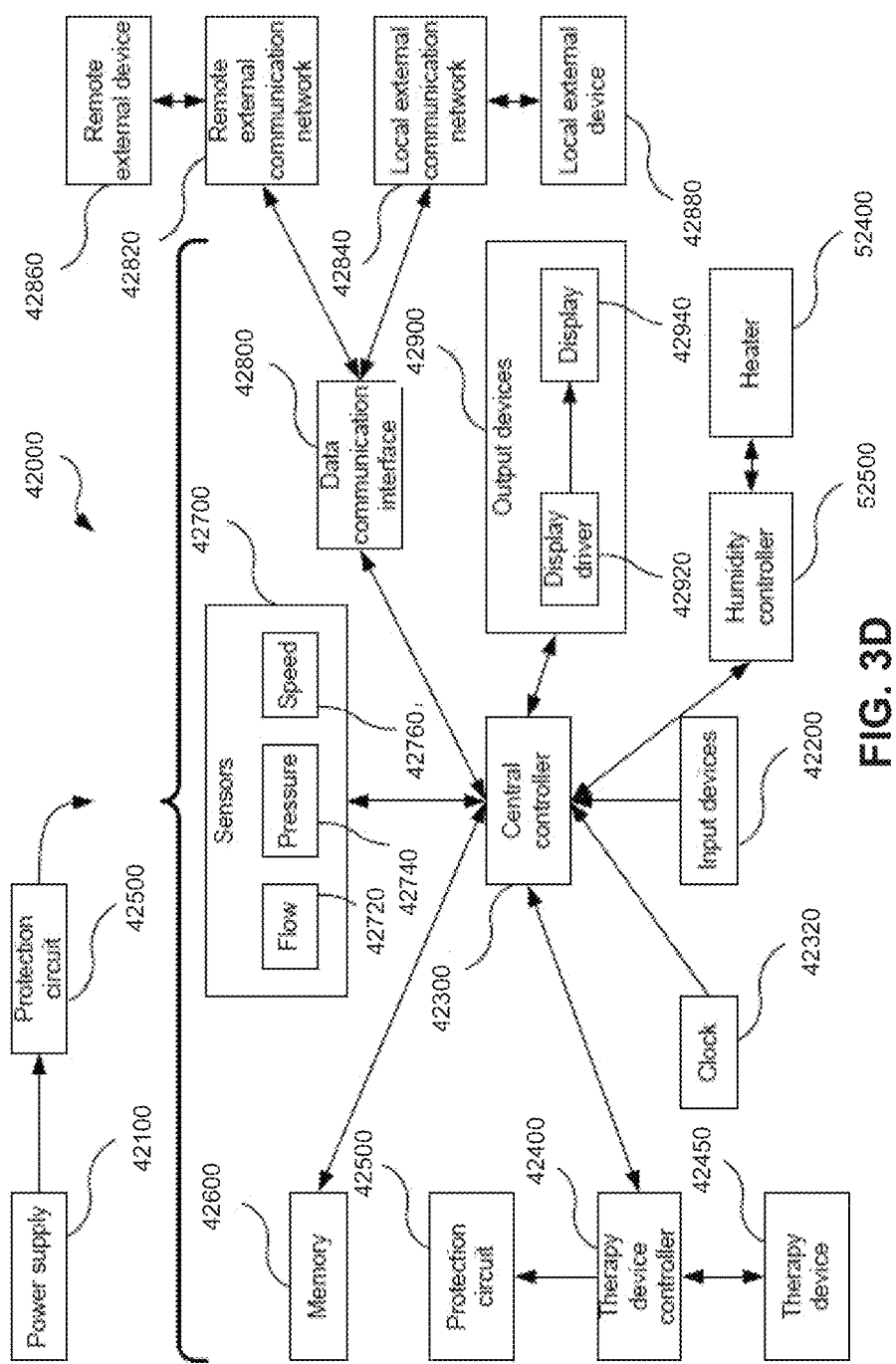
FIG. 3D is a schematic diagram of the electrical components of an RPT device in accordance with one form of the present technology.
Figure 3E:
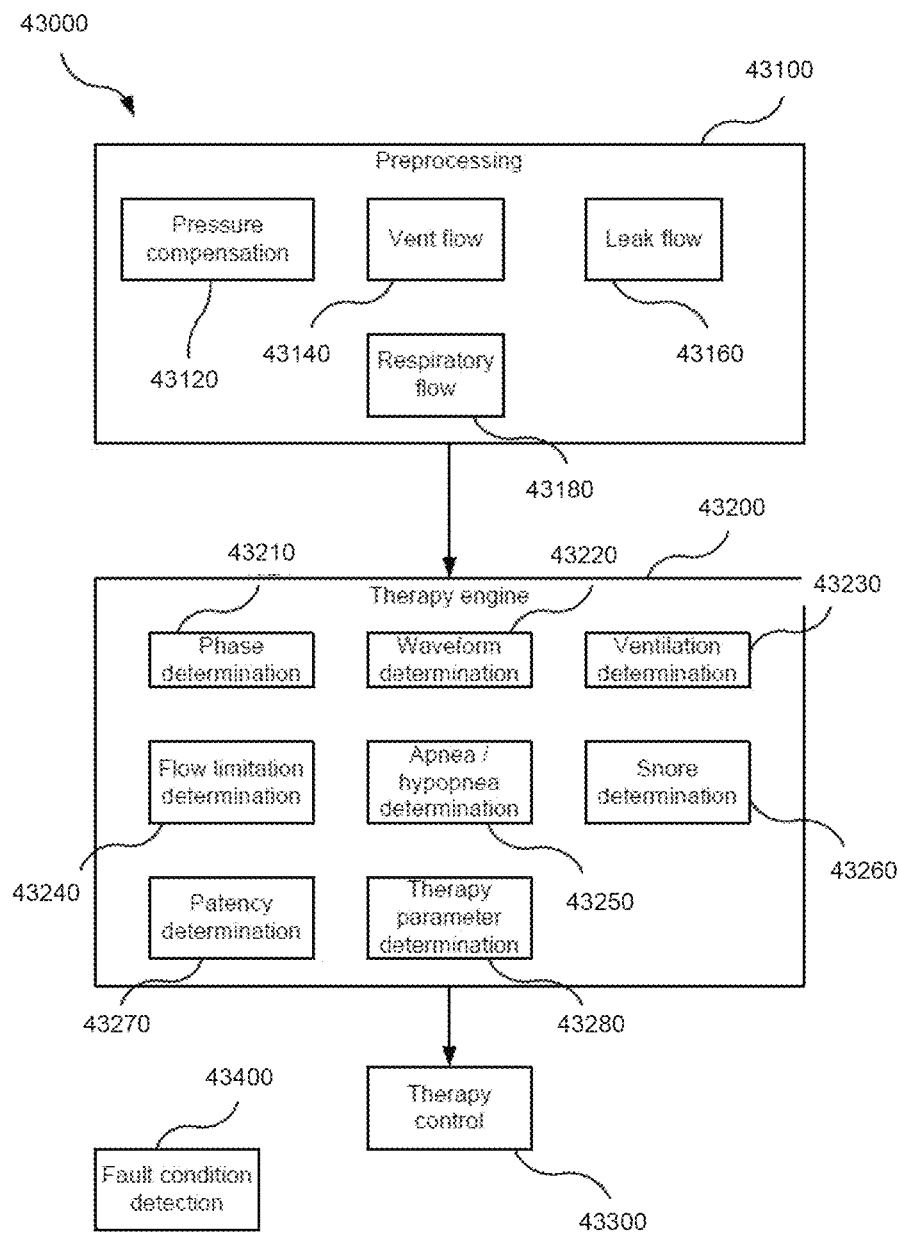
FIG. 3E is a schematic diagram of the algorithms implemented in an RPT device in accordance with one form of the present technology.

In one form, an inlet air filter 41120 is located at the beginning of the pneumatic path upstream of a pressure generator 41400. See FIG. 3C.

In one form, an outlet air filter 41140, for example an antibacterial filter, is located between an outlet of the pneumatic block 40200 and a patient interface 3000. See FIG. 3C.

2.4.1.2 Muffler(s)

In one form of the present technology, an inlet muffler 41220 is located in the pneumatic path upstream of a pressure generator 41400. See FIG. 3C.

In one form of the present technology, an outlet muffler 41240 is located in the pneumatic path between the pressure generator 41400 and a patient interface 3000. See FIG. 3C.

2.4.1.3 Pressure Generator 41400

In one form of the present technology, a pressure generator 41400 for producing a flow, or a supply, of air at positive pressure is a controllable blower 41420. For example the blower 41420 may include a brushless DC motor 41440 with one or more impellers housed in a volute. The blower may be capable of delivering a supply of air, for example at a rate of up to about 120 litres/minute, at a positive pressure in a range from about 4 cmH2O to about 20 cmH2O, or in other forms up to about 30 cmH2O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 41400 is under the control of the therapy device controller 42400.

In other forms, a pressure generator 41400 may be a piston-driven pump, a pressure regulator connected to a high pressure source (e.g. compressed air reservoir), or a bellows.

2.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 42700 are located upstream and/or downstream of the pressure generator 41400. The one or more transducers 42700 may be constructed and arranged to measure properties such as a flow rate, a pressure or a temperature at that point in the pneumatic path.

In one form of the present technology, one or more transducers 42700 may be located proximate to the patient interface 3000.

In one form, a signal from a transducer 42700 may be filtered, such as by low-pass, high-pass or band-pass filtering.

2.4.1.4.1 Flow Rate Transducer

A flow rate transducer 42740 in accordance with the present technology may be based on a differential pressure transducer, for example, an SDP600 Series differential pressure transducer from SENSIRION.

In one form, a signal representing a flow rate such as a total flow rate Qt from the flow rate transducer 42740 is received by the central controller 42300.

2.4.1.4.2 Pressure Transducer 42720

A pressure transducer 42720 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 42720 is received by the central controller 42300.

2.4.1.4.3 Motor Speed Transducer

In one form of the present technology a motor speed transducer 42760 is used to determine a rotational velocity of the motor 41440 and/or the blower 41420. A motor speed signal from the motor speed transducer 42760 may be provided to the therapy device controller 42400. The motor speed transducer 42760 may, for example, be a speed sensor, such as a Hall effect sensor.

2.4.1.5 Anti-Spill Back Valve

In one form of the present technology, an anti-spill back valve is located between the humidifier 50000 and the pneumatic block 40200. The anti-spill back valve is constructed and arranged to reduce the risk that water will flow upstream from the humidifier 50000, for example to the motor 41440.

2.4.1.6 Air Circuit

An air circuit 41700 in accordance with an aspect of the present technology is a conduit or a tube constructed and arranged in use to allow a flow of air to travel between two components such as the pneumatic block 40200 and the patient interface 3000.

In particular, the air circuit 41700 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 41700 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 41700. The heating element may be in communication with a controller such as a central controller 42300 or a humidifier controller. One example of an air circuit 41700 comprising a heated wire circuit is described in United States Patent Application No. US/2011/0023874, which is incorporated herewithin in its entirety by reference.

2.4.1.7 Oxygen Delivery

In one form of the present technology, supplemental oxygen 41800 is delivered to one or more points in the pneumatic path, such as upstream of the pneumatic block 40200, to the air circuit 41700 and/or to the patient interface 3000.

2.4.2 RPT Device Electrical Components 2.4.2.1 Power Supply

A power supply 42100 may be located internal or external of the external housing 40100 of the RPT device 40000.

In one form of the present technology power supply 42100 provides electrical power to the RPT device 40000 only. In another form of the present technology, power supply 42100 provides electrical power to both RPT device 40000 and humidifier 50000.

2.4.2.2 Input Devices

In one form of the present technology, an RPT device 40000 includes one or more input devices 42200 in the form of buttons, switches or dials to allow a person to interact with the device. The buttons, switches or dials may be physical devices, or software devices accessible via a touch screen. The buttons, switches or dials may, in one form, be physically connected to the external housing 40100, or may, in another form, be in wireless communication with a receiver that is in electrical connection to the central controller 42300.

In one form, the input device 42200 may be constructed and arranged to allow a person to select a value and/or a menu option.

2.4.2.3 Central Controller

In one form of the present technology, the central controller 42300 is one or a plurality of processors suitable to control an RPT device 40000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 42300 is a dedicated electronic circuit.

In one form, the central controller 42300 is an application-specific integrated circuit. In another form, the central controller 42300 comprises discrete electronic components.

The central controller 42300 may be configured to receive input signal(s) from one or more transducers 42700, and one or more input devices 42200.

The central controller 42300 may be configured to provide output signal(s) to one or more of an output device 42900, a therapy device controller 42400, a data communication interface 42800 and humidifier controller.

In some forms of the present technology, the central controller 42300 is configured to implement the one or more methodologies described herein, such as the one or more algorithms 43000 expressed as computer programs stored in a non-transitory computer readable storage medium, such as memory 42600. In some forms of the present technology, the central controller 42300 may be integrated with an RPT device 40000. However, in some forms of the present technology, some methodologies may be performed by a remotely located device. For example, the remotely located device may determine control settings for a ventilator or detect respiratory related events by analysis of stored data such as from any of the sensors described herein.

2.4.2.4 Clock

The RPT device 40000 may include a clock 42320 that is connected to the central controller 42300.

2.4.2.5 Therapy Device Controller

In one form of the present technology, therapy device controller 42400 is a control module 43300 that forms part of the algorithms 43000 executed by the central controller 42300.

In one form of the present technology, therapy device controller 42400 is a dedicated motor control integrated circuit. For example, in one form a MC33035 brushless DC motor controller, manufactured by ONSEMI is used.

2.4.2.6 Protection Circuits

The one or more protection circuits 42500 in accordance with the present technology may comprise an electrical protection circuit, a temperature and/or pressure safety circuit.

2.4.2.7 Memory

In accordance with one form of the present technology the RPT device 40000 includes memory 42600, e.g., non-volatile memory. In some forms, memory 42600 may include battery powered static RAM. In some forms, memory 42600 may include volatile RAM.

Memory 42600 may be located on the PCBA 42020. Memory 42600 may be in the form of EEPROM, or NAND flash.

Additionally or alternatively, RPT device 40000 includes a removable form of memory 42600, for example a memory card made in accordance with the Secure Digital (SD) standard.

In one form of the present technology, the memory 42600 acts as a non-transitory computer readable storage medium on which is stored computer program instructions expressing the one or more methodologies described herein, such as the one or more algorithms 43000.

2.4.2.8 Data Communication Systems

In one form of the present technology, a data communication interface 42800 is provided, and is connected to the central controller 42300. Data communication interface 42800 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 42800 is part of the central controller 42300. In another form, data communication interface 42800 is separate from the central controller 42300, and may comprise an integrated circuit or a processor.

In one form, remote external communication network 4282 is the Internet. The data communication interface 42800 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

2.4.2.9 Output Devices Including Optional Display, Alarms

An output device 42900 in accordance with the present technology may take the form of one or more of a visual, audio and haptic unit. A visual display may be a Liquid Crystal Display (LCD) or Light Emitting Diode (LED) display.

2.4.2.9.1 Display Driver

A display driver 4292 receives as an input the characters, symbols, or images intended for display on the display 4294, and converts them to commands that cause the display 4294 to display those characters, symbols, or images.

2.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

2.4.3 RPT Device Algorithms

2.4.3.1 Pre-Processing Module

A pre-processing module 4310 in accordance with one form of the present technology receives as an input a signal from a transducer 42700, for example a flow rate transducer 42740 or pressure transducer 42720, and performs one or more process steps to calculate one or more output values that will be used as an input to another module, for example a therapy engine module 43200.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate 4314, leak flow rate 4316, and respiratory flow rate 4318.

2.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 41700 and provides as an output an estimated pressure, Pm, in the patient interface 3000.

2.4.3.1.2 Vent Flow Rate Estimation

In one form of the present technology, a vent flow rate calculation algorithm 4314 receives as an input an estimated pressure, Pm, in the patient interface 3000 and estimates a vent flow rate of air, Qv, from a vent 3400 in a patient interface 3000.

2.4.3.1.3 Leak Flow Rate Estimation

In one form of the present technology, a leak flow rate algorithm 4316 receives as an input a total flow rate, Qt, and a vent flow rate Qv, and provides as an output an estimate of the leak, i.e. leak flow rate, Ql, by calculating an average of the difference between total flow rate Qt and vent flow rate Qv over a period sufficiently long to include several breathing cycles, e.g. about 10 seconds.

In one form, the leak flow rate algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be calculated as the product of leak conductance and a function of pressure, Pm.

2.4.3.1.4 Respiratory Flow Rate Estimation

In one form of the present technology, a respiratory flow rate algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

2.4.3.2 Therapy Engine Module

In one form of the present technology, a therapy engine module 43200 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of a level of pressure support, and a target ventilation.

In various forms, the therapy engine module 432000 comprises one or more of the following algorithms: phase determination 43210, waveform determination 43220, ventilation determination 43230, inspiratory flow limitation determination 43240, apnea/hypopnea determination 43250, snore determination 43260, airway patency determination 43270, target ventilation determination 43280, and therapy parameter determination 43290.

2.4.3.2.1 Phase Determination

In one form of the present technology, the RPT device 40000 does not determine phase.

In one form of the present technology, a phase determination algorithm 43210 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 40000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 40000) when the respiratory flow rate Qr has a value that exceeds a positive threshold, and a discrete value of 0.5 revolutions (thereby "cycling" the RPT device 40000) when a respiratory flow rate Qr has a value that is more negative than a negative threshold.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. The rate of change of continuously valued phase (in revolutions) with respect to time is equal to the instantaneous breathing rate in breaths per second. RPT devices 40000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination that is independent of the respiratory flow rate Qr, the phase Φ is determined as the half the proportion of the inhalation time Ti that has elapsed since the previous trigger instant, or 0.5 revolutions plus half the proportion of the exhalation time Te that has elapsed since the previous cycle instant (whichever was more recent).

2.4.3.2.2 Waveform Determination

In one form of the present technology, the therapy parameter determination algorithm 43290 provides an approximately constant treatment pressure throughout a respiratory cycle of a patient.

In others form of the present technology, the therapy parameter determination algorithm 43290 controls the pressure generator 41400 to provide a treatment pressure Pt that varies throughout a respiratory cycle of a patient according to a waveform template.

In one form of the present technology, a waveform determination algorithm 43220 provides a waveform template Π(Φ) with values in the range [0, 1] on the domain of phase values Φ provided by the phase determination algorithm 43210 to be used by the therapy parameter determination algorithm 43290.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions.

In some forms of the present technology, the waveform determination algorithm 43220 selects a waveform template $\Pi(\Phi)$ from a library of waveform templates, dependent on a setting of the RPT device. In other forms, the waveform determination algorithm 43220 instantiates a waveform template $\Pi(\Phi)$ from a generic waveform template using one or more parameters (e.g. time constant of an exponentially curved portion) that are dependent on a current state of the patient 1000.

The predetermined waveform template $\Pi(\Phi)$ may be provided as a lookup table of values H as a function of phase values $\Phi$. This approach is particularly suitable when the phase determination algorithm 43210 returns discrete values of phase such as 0 for inhalation and 0.5 for exhalation. This approach may also be used when the phase determination algorithm 43210 returns a continuously-valued phase $\Phi$.

2.4.3.2.3 Ventilation Determination

In one form of the present technology, a ventilation determination algorithm 43230 receives as an input a respiratory flow rate Qr, and determines a measure indicative of current patient ventilation, Vent.

In some implementations, the ventilation determination algorithm 43230 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 43230 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

2.4.3.2.4 Determination of Inspiratory Flow limitation

In one form of the present technology, the central controller 42300 executes one or more algorithms 43240 for the detection of inspiratory flow limitation.

In one form, the algorithm 43240 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scaler to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 3I. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 42300 for the preceding several inspiratory events. This is repeated over the same inspiratory events for the second such point, and so on. Thus, for example, sixty five scaled data points are generated by the central controller 42300, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

2.4.3.2.5 Determination of Apneas and Hypopneas

In one form of the present technology, the central controller 42300 executes one or more algorithms 43250 for the determination of the presence of apneas and/or hypopneas.

The one or more algorithms 43250 receive as an input a respiratory flow rate signal Qr and provide as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

2.4.3.2.6 Determination of Snore

In one form of the present technology, the central controller 42300 executes one or more snore algorithms 43260 for the detection of snore.

In one form the snore algorithm 43260 receives as an input a respiratory flow rate signal Qr and provides as an output a metric of the extent to which snoring is present.

The algorithm 43260 may comprise the step of determining the intensity of the flow rate signal in the range of 30-300 Hz. Further the algorithm 43260 may comprise a step of filtering the respiratory flow rate signal Qr to reduce background noise, e.g., the sound of airflow in the system from the blower.

2.4.3.2.7 Determination of Airway Patency

In one form of the present technology, the central controller 42300 executes one or more algorithms 43270 for the determination of airway patency.

In one form, airway patency algorithm 43270 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH2O.

In one form, airway patency algorithm 43270 receives as an input a respiratory flow rate signal Qr, and determines the presence or absence of a cardiogenic signal. The absence of a cardiogenic signal is taken to be an indication of a closed airway.

2.4.3.2.8 Determination of Target Ventilation

In one form of the present technology, the central controller 42300 takes as input the measure of current ventilation, Vent, and executes one or more algorithms 43280 for the determination of a target value Vtgt for the measure of ventilation.

In some forms of the present technology, there is no target ventilation determination algorithm 4328, and the target value Vtgt is predetermined, for example by hard-coding during configuration of the RPT device 40000 or by manual entry through the input device 42200.

In other forms of the present technology, such as adaptive servo-ventilation (ASV), the target ventilation determination algorithm 43280 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 43280 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

2.4.3.2.9 Determination of Therapy Parameters

In some forms of the present technology, the central controller 42300 executes one or more algorithms 43290 for the determination of one or more therapy parameters using the values returned by one or more of the other algorithms in the therapy engine module 43200.

In one form of the present technology, the therapy parameter is an instantaneous treatment pressure Pt. In one implementation of this form, the therapy parameter determination algorithm 43290 determines the treatment pressure Pt using the equation $$Pt = A\Pi(\Phi) + P_0 \qquad (1)$$

where:

A is the pressure support, $\Pi(\Phi)$ is the waveform template value (in the range 0 to 1) at the current value $\Phi$ of phase, and $P_0$ is a base pressure.

By determining the treatment pressure Pt using equation (1), the therapy parameter determination algorithm 43290 oscillates the treatment pressure Pt in synchrony with the spontaneous respiratory effort of the patient 1000. That is to say, based on the typical waveform templates $\Pi(\Phi)$ described above, the therapy parameter determination algorithm 43290 increases the treatment pressure Pt at the start of, or during, or inspiration and decreases the treatment pressure Pt at the start of, or during, expiration. The (non-negative) pressure support A is the amplitude of the oscillation.

If the waveform determination algorithm 43220 provides the waveform template $\Pi(\Phi)$ as a lookup table, the therapy parameter determination algorithm 43290 applies equation (1) by locating the nearest lookup table entry to the current value $\Phi$ of phase returned by the phase determination algorithm 4321, or by interpolation between the two entries straddling the current value $\Phi$ of phase.

The values of the pressure support A and the base pressure P0 may be set by the therapy parameter determination algorithm 43290 depending on the chosen pressure therapy mode in the manner described below.

2.4.3.3 Therapy Control Module

Therapy control module 43300 in accordance with one aspect of the present technology receives as inputs the therapy parameters from the therapy parameter determination algorithm 43290 of the therapy engine module 43200, and controls the pressure generator 41400 to deliver a flow of air in accordance with the therapy parameters.

In one form of the present technology, the therapy parameter is a treatment pressure Pt, and the therapy control module 43300 controls the pressure generator 41400 to deliver a flow of air whose mask pressure Pm at the patient interface 3000 is equal to the treatment pressure Pt.

2.4.3.4 Detection of Fault Conditions

In one form of the present technology, the central controller 42300 executes one or more methods for the detection of fault conditions. The fault conditions detected by the one or more methods may include at least one of the following:

Power failure (no power, or insufficient power)
Transducer fault detection
Failure to detect the presence of a component
Operating parameters outside recommended ranges (e.g. pressure, flow rate, temperature, PaO2)
Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm
Sending a message to an external device
Logging of the incident

2.5 Humidifier

2.5.1 Humidifier Overview

Figure 3F:
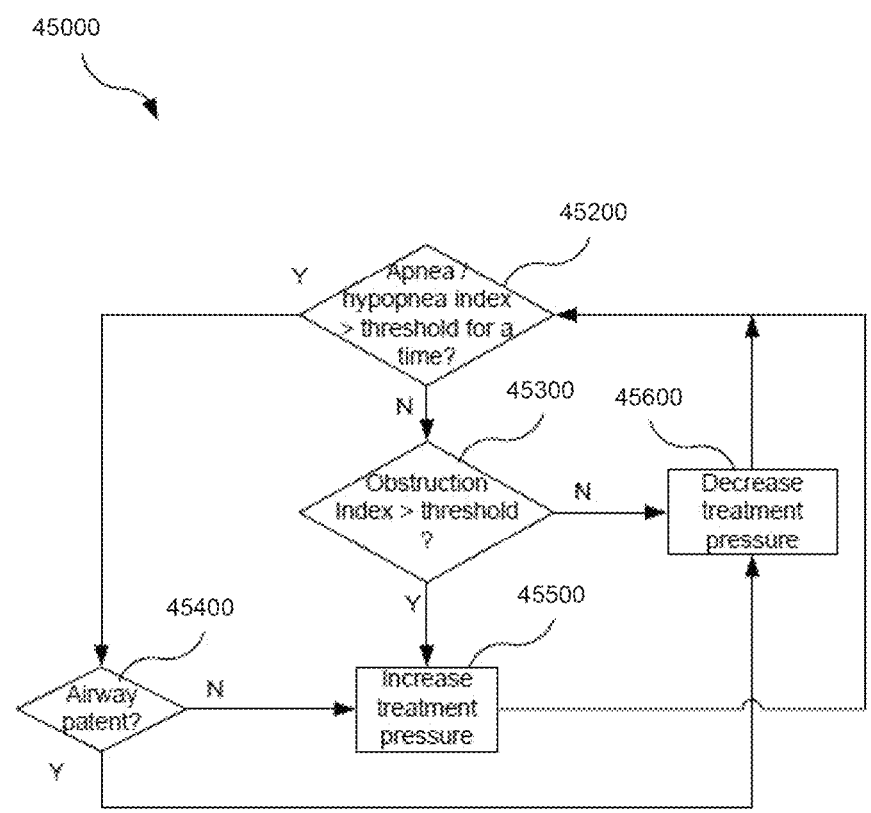
FIG. 3F is a flow chart illustrating a method carried out by the therapy engine module of FIG. 3E in accordance with one form of the present technology.
Figure 3G:
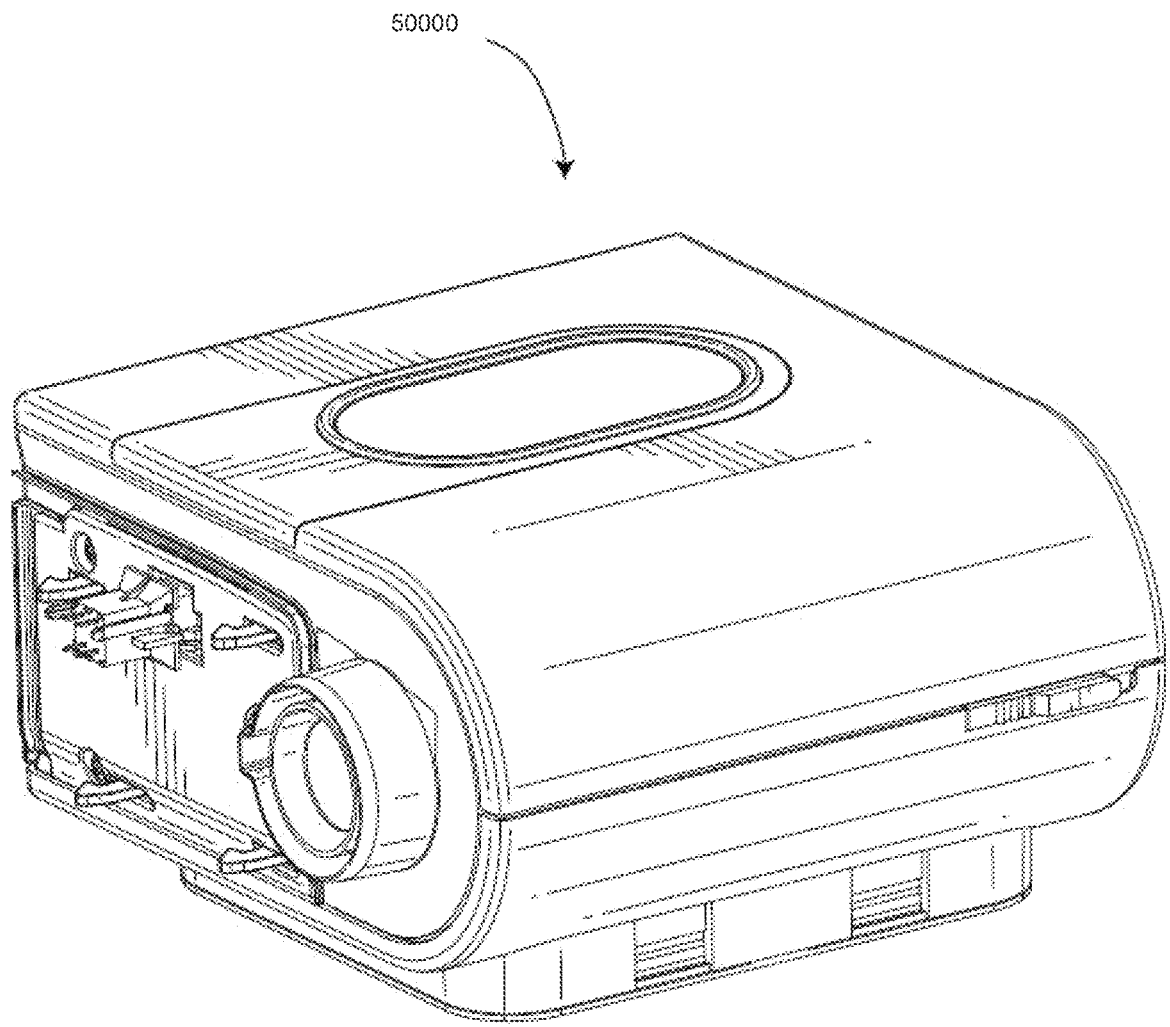
FIG. 3G shows an isometric view of a humidifier in accordance with one form of the present technology.

In one form of the present technology there is provided a humidifier 50000 (e.g. as shown in FIG. 3G) to change the absolute humidity of air or gas for delivery to a patient relative to ambient air. Typically, the humidifier 50000 is used to increase the absolute humidity and increase the temperature of the flow of air (relative to ambient air) before delivery to the patient's airways.

The humidifier 50000 may comprise a humidifier reservoir, a humidifier inlet to receive a flow of air, and a humidifier outlet to deliver a humidified flow of air. In some forms, an inlet and an outlet of the humidifier reservoir may be the humidifier inlet and the humidifier outlet respectively. The humidifier 50000 may further comprise a humidifier base, which may be adapted to receive the humidifier reservoir and comprise a heating element.

2.5.2 Humidifier Mechanical Components

2.5.2.1 Water Reservoir

According to one arrangement, the humidifier 50000 may comprise a water reservoir configured to hold, or retain, a volume of liquid (e.g. water) to be evaporated for humidification of the flow of air. The water reservoir may be configured to hold a predetermined maximum volume of water in order to provide adequate humidification for at least the duration of a respiratory therapy session, such as one evening of sleep. Typically, the reservoir is configured to hold several hundred millilitres of water, e.g. 300 millilitres (ml), 325 ml, 350 ml or 400 ml. In other forms, the humidifier 50000 may be configured to receive a supply of water from an external water source such as a building's water supply system.

According to one aspect, the water reservoir is configured to add humidity to a flow of air from the RPT device 40000 as the flow of air travels therethrough. In one form, the water reservoir may be configured to encourage the flow of air to travel in a tortuous path through the reservoir while in contact with the volume of water therein.

According to one form, the reservoir may be removable from the humidifier 50000, for example in a lateral direction.

The reservoir may also be configured to discourage egress of liquid therefrom, such as when the reservoir is displaced and/or rotated from its normal, working orientation, such as through any apertures and/or in between its sub-components. As the flow of air to be humidified by the humidifier 50000 is typically pressurised, the reservoir may also be configured to prevent losses in pneumatic pressure through leak and/or flow impedance.

2.5.2.2 Conductive Portion

According to one arrangement, the reservoir comprises a conductive portion 51200 configured to allow efficient transfer of heat from the heating element 52400 to the volume of liquid in the reservoir 51100. In one form, the conductive portion 51200 may be arranged as a plate, although other shapes may also be suitable. All or a part of the conductive portion 51200 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

2.5.2.3 Humidifier Reservoir Dock

Figure 3H:
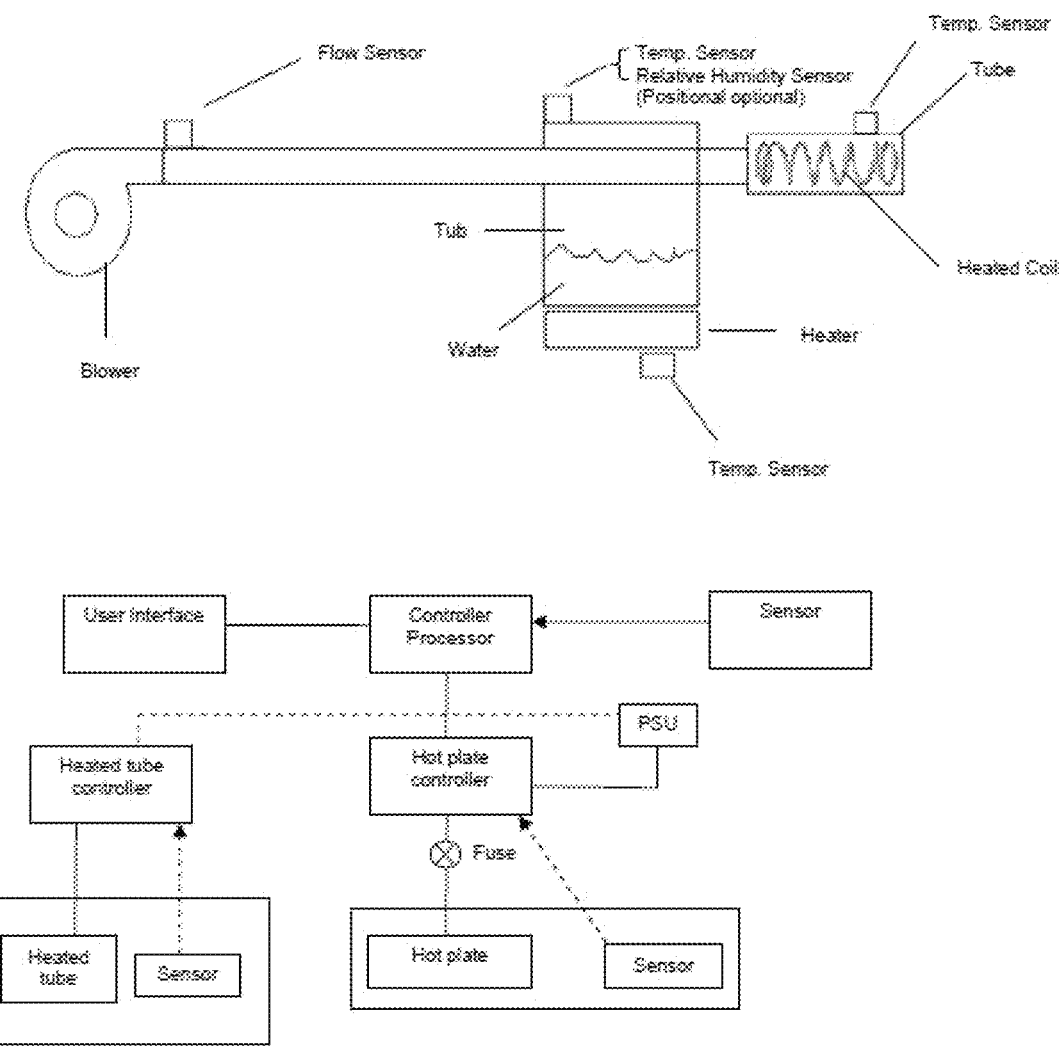
FIG. 3H shows an isometric view of a humidifier in accordance with one form of the present technology, showing a humidifier reservoir 5110 removed from the humidifier reservoir dock 5130.

In one form, the humidifier 50000 may comprise a humidifier reservoir dock 51300 (as shown in FIG. 3H) configured to receive the humidifier reservoir 51100. In some arrangements, the humidifier reservoir dock 51300 may comprise a locking feature such as a locking lever 51350 configured to retain the reservoir 51100 in the reservoir dock 51300.

2.5.2.4 Water Level Indicator

The humidifier reservoir 51100 may comprise a water level indicator 51500 as shown in FIG. 3G-3H. In some forms, the water level indicator 51500 may provide one or more indications to a user such as the patient 1000 or a care giver regarding a quantity of the volume of water in the humidifier reservoir 51100. The one or more indications provided by the water level indicator 51500 may include an indication of a maximum, predetermined volume of water, any portions thereof, such as 25%, 50% or 75% or volumes such as 200 ml, 300 ml or 400 ml.

2.5.3 Humidifier Electrical & Thermal Components

The humidifier 50000 may comprise a number of electrical and/or thermal components such as those listed below.

2.5.3.1 Humidifier Transducer(s)

The humidifier 50000 may comprise one or more humidifier transducers (sensors) 52100 instead of, or in addition to, transducers 42700 described above. Humidifier transducers 52100 may include one or more of an air pressure sensor 52120, an air flow rate transducer 52140, a temperature sensor 52160, or a humidity sensor 52180 as shown in FIG. 5c. A humidifier transducer 52100 may produce one or more output signals which may be communicated to a controller such as the central controller 42300 and/or the humidifier controller 52500. In some forms, a humidifier transducer may be located externally to the humidifier 50000 (such as in the air circuit 41700) while communicating the output signal to the controller.

2.5.3.1.1 Pressure Transducer

One or more pressure transducers 52120 may be provided to the humidifier 50000 in addition to, or instead of, a pressure transducer 42720 provided in the RPT device 40000.

2.5.3.1.2 Flow Rate Transducer

One or more flow rate transducers 52140 may be provided to the humidifier 50000 in addition to, or instead of, a flow rate transducer 42740 provided in the RPT device 40000.

2.5.3.1.3 Temperature Transducer

The humidifier 50000 may comprise one or more temperature transducers 52160. The one or more temperature transducers 52160 may be configured to measure one or more temperatures such as of the heating element 52400 and/or of the flow of air downstream of the humidifier outlet 50040. In some forms, the humidifier 50000 may further comprise a temperature sensor 5216 to detect the temperature of the ambient air.

2.5.3.1.4 Humidity Transducer

In one form, the humidifier 50000 may comprise one or more humidity sensors 52180 to detect a humidity of a gas, such as the ambient air. The humidity sensor 52180 may be placed towards the humidifier outlet 50040 in some forms to measure a humidity of the gas delivered from the humidifier 50000. The humidity sensor may be an absolute humidity sensor or a relative humidity sensor.

2.5.3.2 Heating Element

A heating element 52400 may be provided to the humidifier 50000 in some cases to provide a heat input to one or more of the volume of water in the humidifier reservoir 51100 and/or to the flow of air. The heating element 52400 may comprise a heat generating component such as an electrically resistive heating track. One suitable example of a heating element 52400 is a layered heating element such as one described in the PCT Patent Application Publication No. WO 2012/171072, which is incorporated herewith by reference in its entirety.

In some forms, the heating element 52400 may be provided in the humidifier base 50060 where heat may be provided to the humidifier reservoir 51100 primarily by conduction as shown in FIG. 3H.

2.5.3.3 Humidifier Controller

According to one arrangement of the present technology, a humidifier 50000 may comprise a humidifier controller 52500. In one form, the humidifier controller 52500 may be a part of the central controller 42300. In another form, the humidifier controller 52500 may be a separate controller, which may be in communication with the central controller 42300.

In one form, the humidifier controller 52500 may receive as inputs measures of characteristics (such as temperature, humidity, pressure and/or flow rate), for example of the flow of air, the water in the reservoir 51100 and/or the humidifier 50000. The humidifier controller 52500 may also be configured to execute or implement humidifier algorithms and/or deliver one or more output signals.

Humidifier controller may comprise one or more controllers, such as a central humidifier controller 52510, a heated air circuit controller 52540 configured to control the temperature of a heated air circuit 41710 and/or a heating element controller 52520 configured to control the temperature of a heating element 52400.

2.6 Breathing Waveforms

Figure 3I:
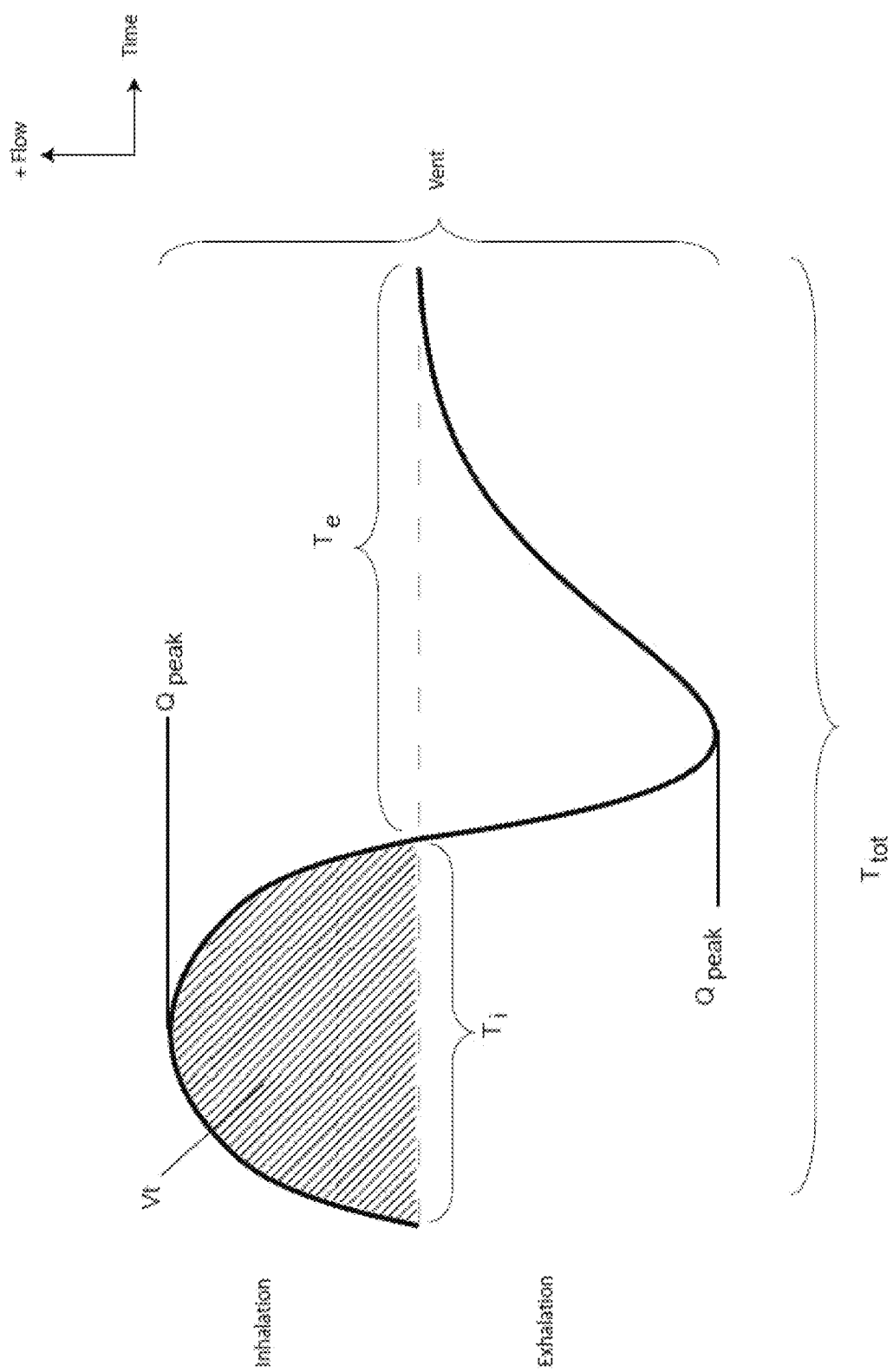
FIG. 3I shows a model typical breath waveform of a person while sleeping.

FIG. 3I shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 3J:
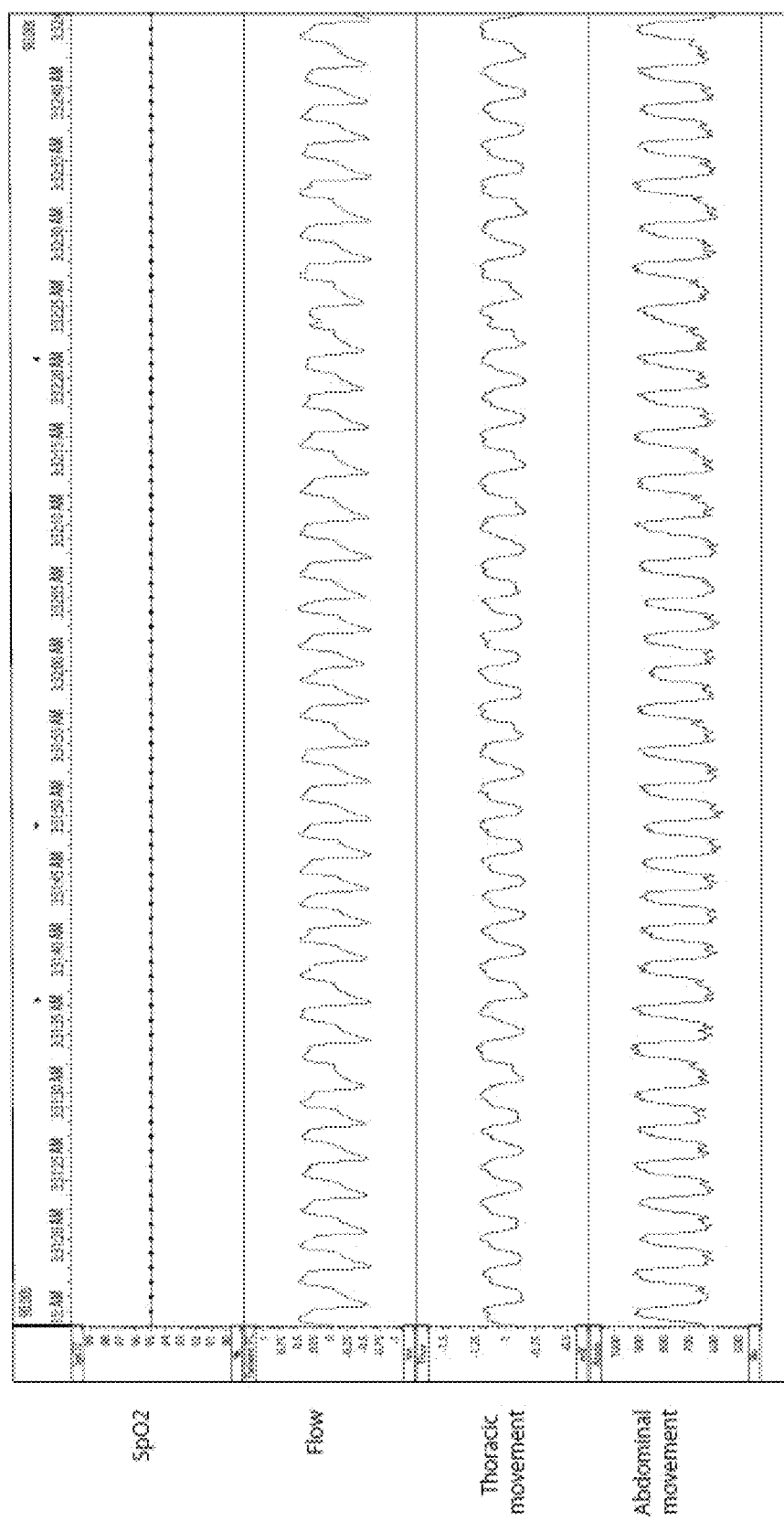
FIG. 3J shows a patient during Non-REM sleep breathing normally over a period of about ninety seconds.

FIG. 3J shows a patient during Non-REM sleep breathing normally over a period of about ninety seconds, with about 34 breaths, being treated with Automatic PAP, and the mask pressure being about 11 cmH2O. The top channel shows oximetry (SpO2), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 3K:
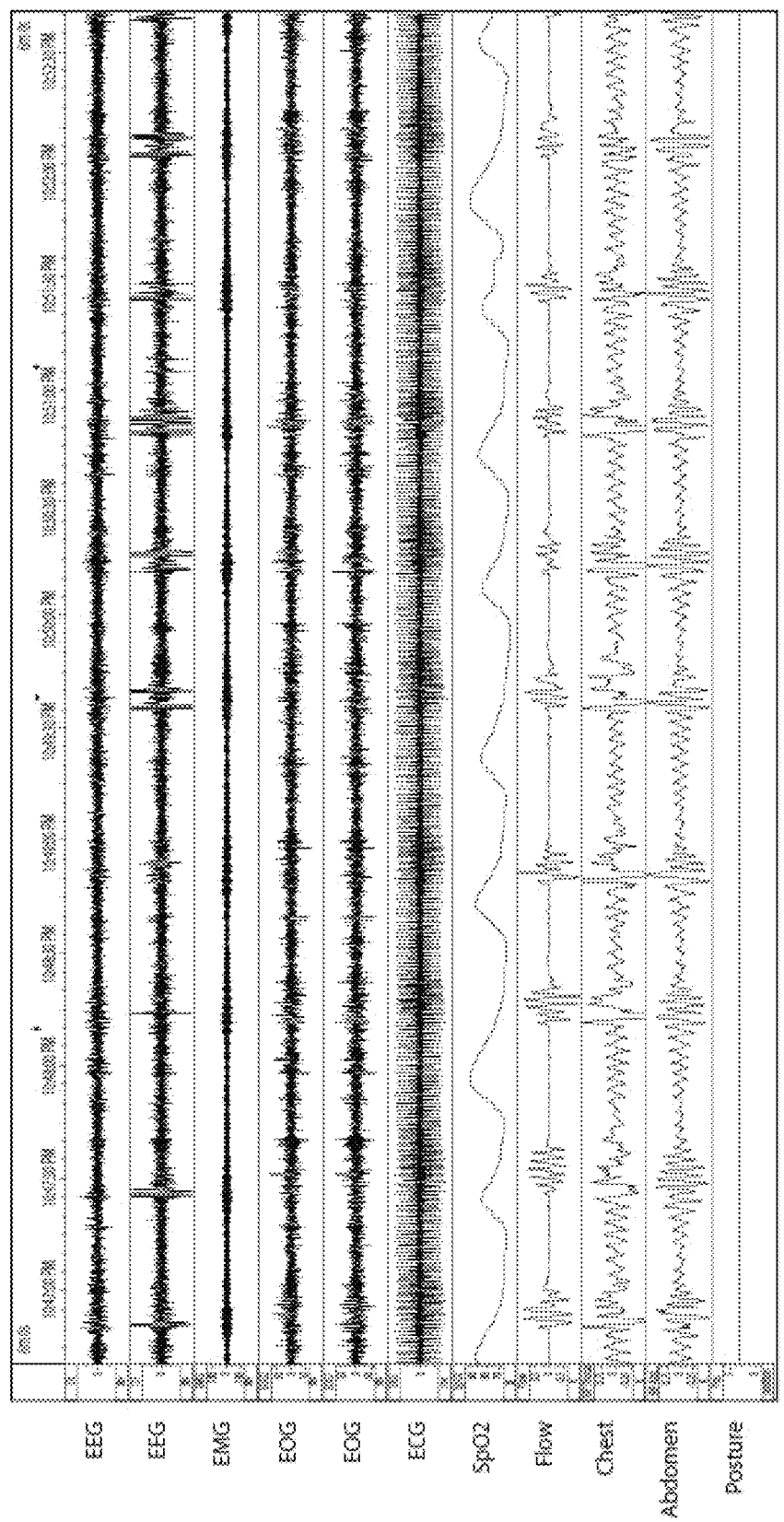
FIG. 3K shows polysomnography of a patient before treatment.

FIG. 3K shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electrocardiogram. The seventh channel shows pulse oximetry (SpO2) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 3L:
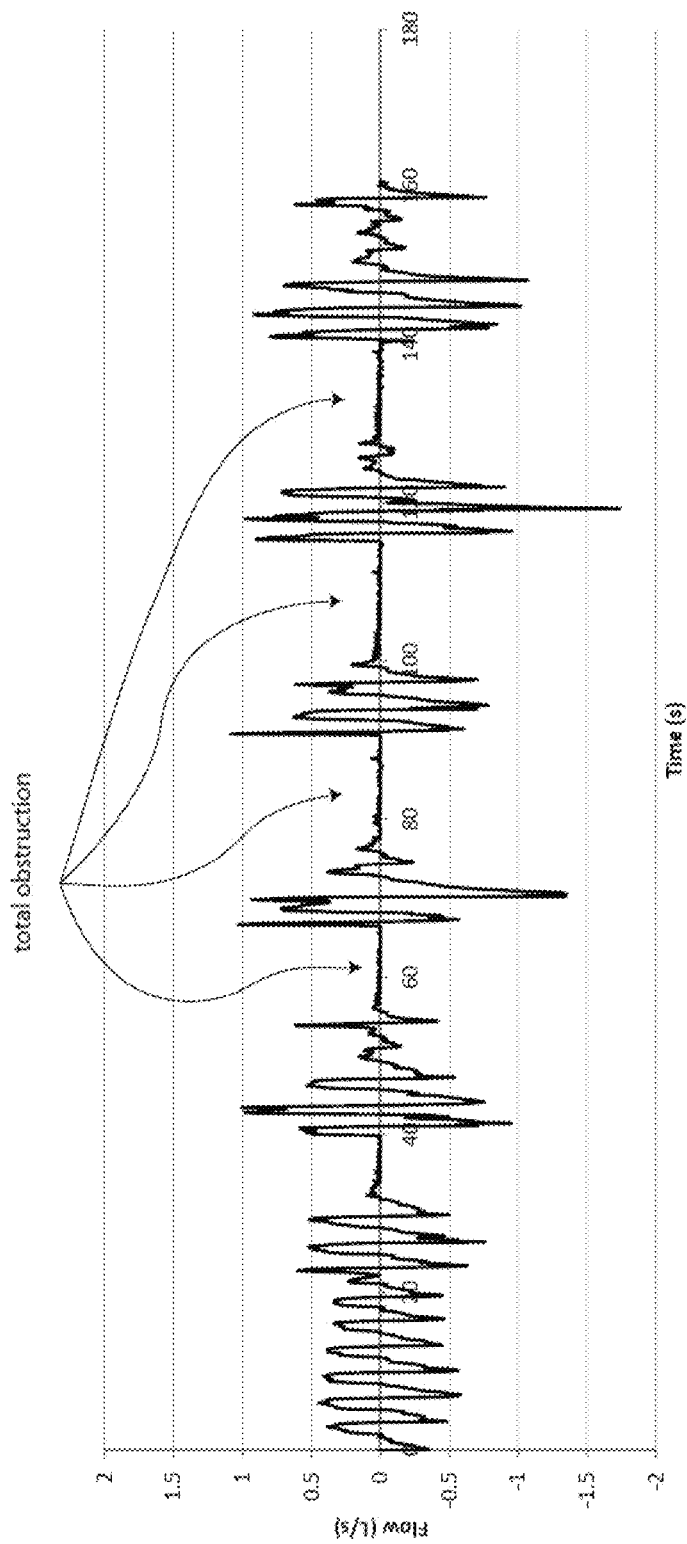
FIG. 3L shows patient flow data where the patient is experiencing a series of total obstructive apneas.

FIG. 3L shows patient flow rate data where the patient is experiencing a series of total obstructive apneas. The duration of the recording is approximately 160 seconds. Flow rates range from about +1 L/s to about −1.5 L/s. Each apnea lasts approximately 10-15 s.

Figure 3M:
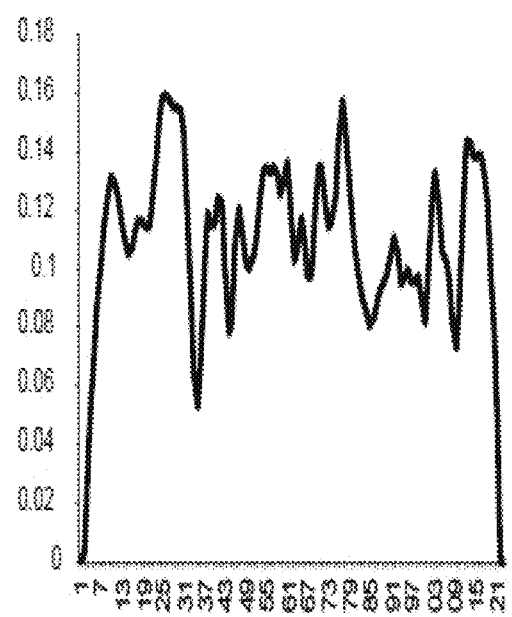
FIG. 3M shows a scaled inspiratory portion of a breath where the patient is experiencing low frequency inspiratory snore.

FIG. 3M shows a scaled inspiratory portion of a breath where the patient is experiencing low frequency inspiratory snore.

Figure 3N:
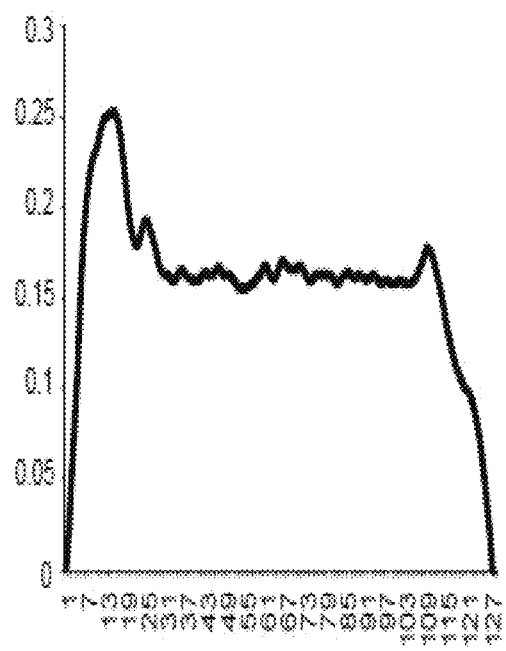
FIG. 3N shows a scaled inspiratory portion of a breath where the patient is experiencing an example of flattened inspiratory flow limitation.

FIG. 3N shows a scaled inspiratory portion of a breath where the patient is experiencing an example of flattened inspiratory flow limitation.

Figure 3O:
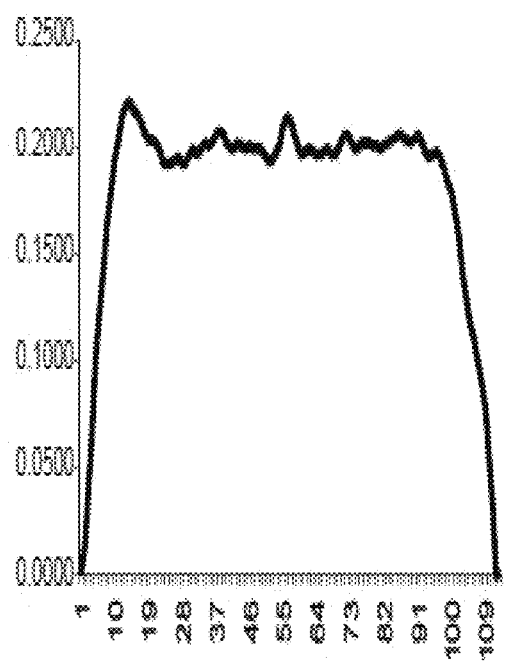
FIG. 3O shows a scaled inspiratory portion of a breath where the patient is experiencing an example of "mesa" flattened inspiratory flow limitation.

FIG. 3O shows a scaled inspiratory portion of a breath where the patient is experiencing an example of "mesa" flattened inspiratory flow limitation.

Figure 3P:
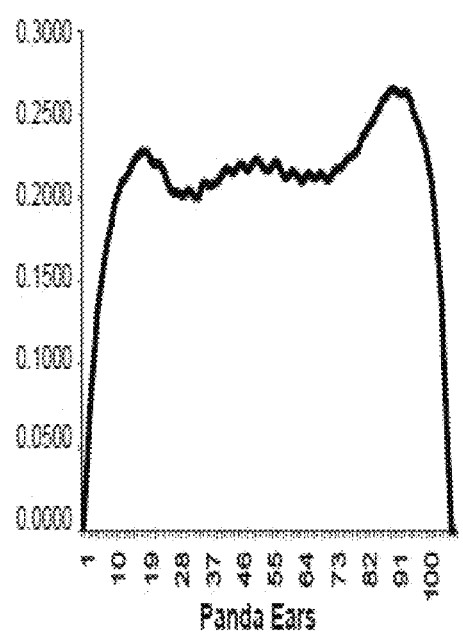
FIG. 3P shows a scaled inspiratory portion of a breath where the patient is experiencing an example of "panda ears" inspiratory flow limitation.

FIG. 3P shows a scaled inspiratory portion of a breath where the patient is experiencing an example of "panda ears" inspiratory flow limitation.

Figure 3Q:
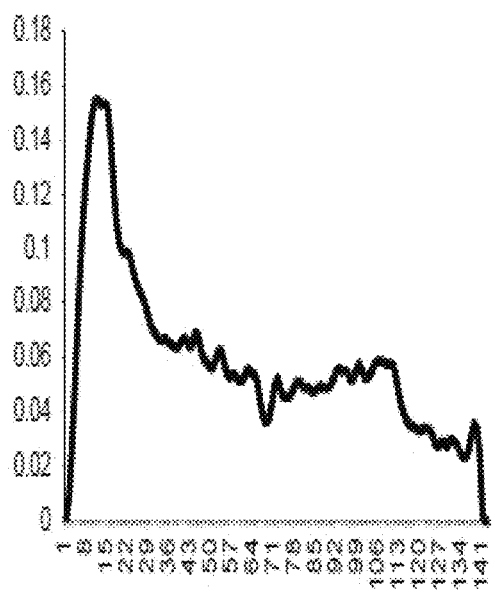
FIG. 3Q shows a scaled inspiratory portion of a breath where the patient is experiencing an example of "chair" inspiratory flow limitation.

FIG. 3Q shows a scaled inspiratory portion of a breath where the patient is experiencing an example of "chair" inspiratory flow limitation.

Figure 3R:
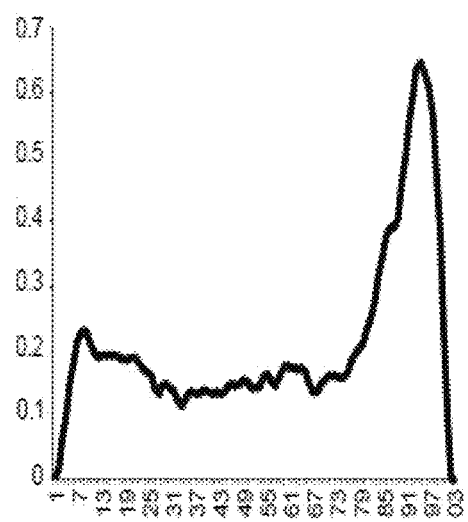
FIG. 3R shows a scaled inspiratory portion of a breath where the patient is experiencing an example of "reverse chair" inspiratory flow limitation.

FIG. 3R shows a scaled inspiratory portion of a breath where the patient is experiencing an example of "reverse chair" inspiratory flow limitation.

Figure 3S:
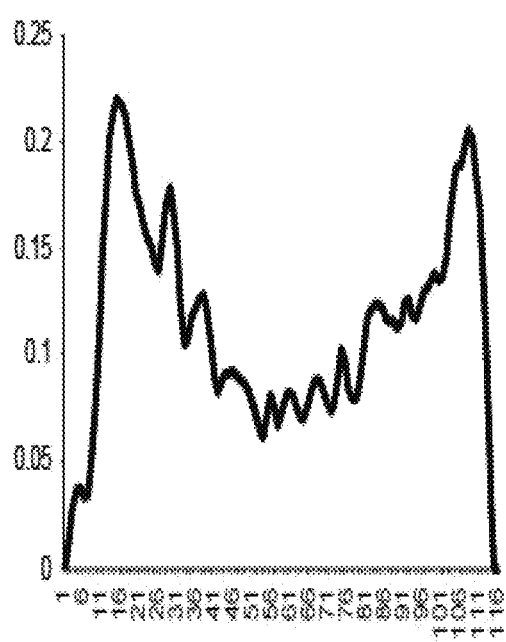
FIG. 3S shows a scaled inspiratory portion of a breath where the patient is experiencing an example of "M-shaped" inspiratory flow limitation.

FIG. 3S shows a scaled inspiratory portion of a breath where the patient is experiencing an example of "M-shaped" inspiratory flow limitation.

Figure 3T:
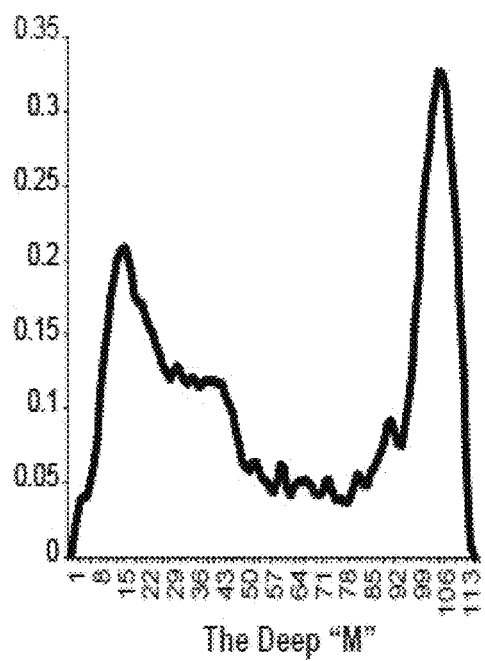
FIG. 3T shows a scaled inspiratory portion of a breath where the patient is experiencing an example of severely "M-shaped" inspiratory flow limitation.

FIG. 3T shows a scaled inspiratory portion of a breath where the patient is experiencing an example of severely "M-shaped" inspiratory flow limitation.

Figure 3U:
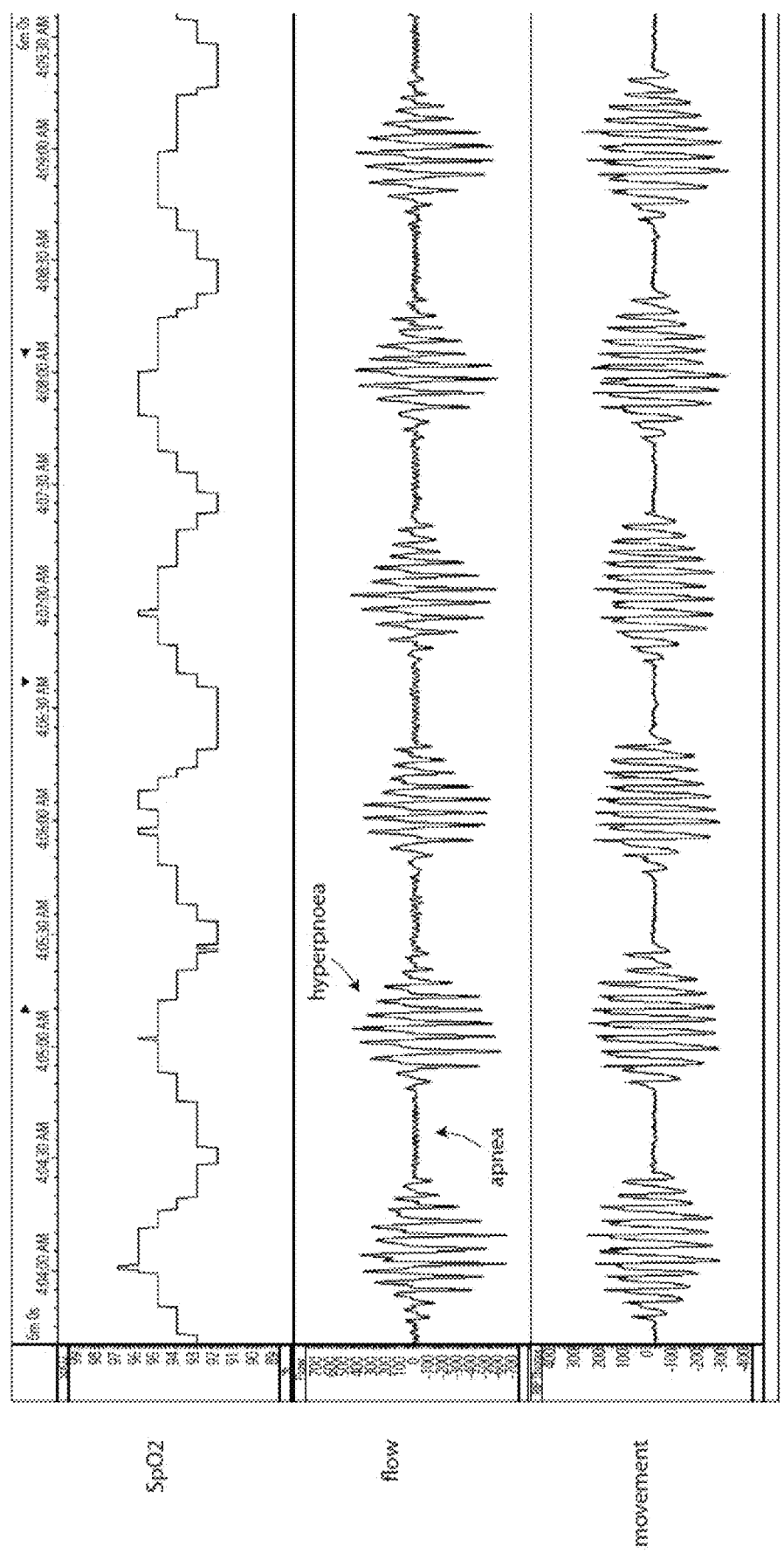
FIG. 3U shows patient data from a patient with Cheyne-Stokes respiration.

FIG. 3U shows patient data from a patient with Cheyne-Stokes respiration. There are three channels: oxygen saturation (SpO2); a signal indicative of flow rate; and thoracic movement. The data span six minutes. The signal representative of flow rate was measured using a pressure sensor connected to nasal cannula. The patient exhibits apneas of about 22 seconds and hyperpneas of about 38 seconds. The higher frequency low amplitude oscillation during apnea is cardiogenic.

Figure 3V:
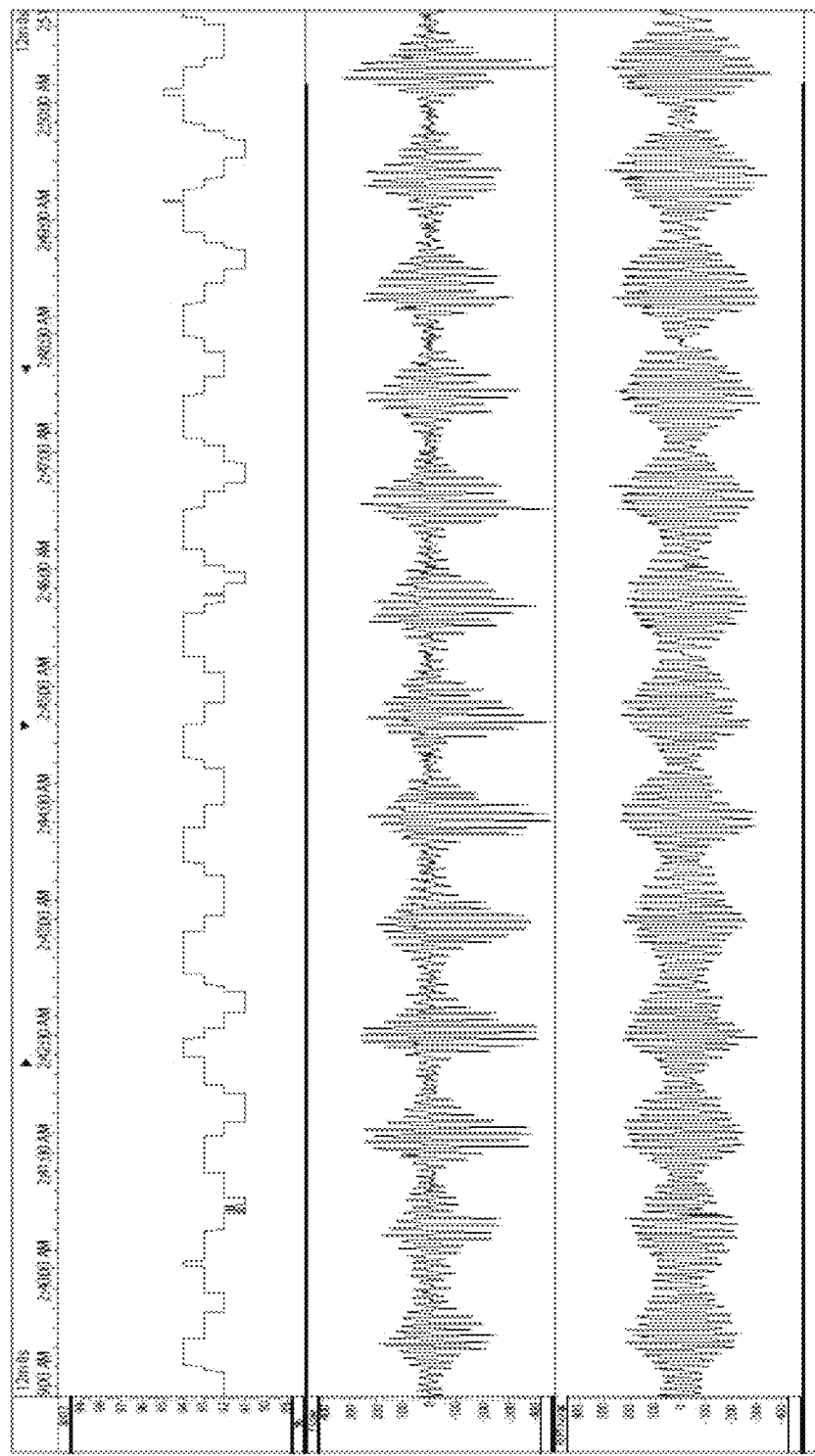
FIG. 3V shows patient data from a patient with another example of Cheyne-Stokes respiration, using the same three channels as in FIG. 3U.

FIG. 3V shows patient data from a patient with another example of Cheyne-Stokes respiration, using the same three channels as in FIG. 3U. The data span ten minutes. The patient exhibits hyperpneas of about 30 seconds and hypopneas of about 30 seconds.

2.7 Pressure Therapy Modes

Various respiratory pressure therapy modes may be implemented by the RPT device 40000 depending on the values of the parameters A and P0 in the treatment pressure equation (1) used by the therapy parameter determination algorithm 43290 in one form of the present technology.

2.7.1 CPAP Therapy

In some implementations of this form of the present technology, the pressure support A is identically zero, so the treatment pressure Pt is identically equal to the base pressure P0 throughout the respiratory cycle. Such implementations are generally grouped under the heading of CPAP therapy. In such implementations, there is no need for the therapy engine module 43200 to determine phase $\Phi$ or the waveform template $\Pi(\Phi)$.

In CPAP therapy modes, the base pressure P0 may be a constant value that is prescribed or determined during titration and hard-coded or manually entered to the RPT device 40000. This alternative is sometimes referred to as constant CPAP therapy. Alternatively, the therapy parameter determination algorithm 43290 may continuously compute the base pressure P0 as a function of indices or measures of sleep disordered breathing returned by the respective algorithms in the therapy engine module 43200, such as one or more of flow limitation, apnea, hypopnea, patency, and snore. This alternative is sometimes referred to as APAP therapy.

FIG. 3F is a flow chart illustrating a method 45000 carried out by the central controller 42300 to continuously compute the base pressure P0 as part of an APAP therapy implementation of the therapy parameter determination algorithm 43290, when the pressure support A is identically zero.

The method 45000 starts at step 45200, at which the central controller 42300 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 45000 proceeds to step 45400; otherwise, the method 45000 proceeds to step 45300. At step 45400, the central controller 423000 compares the measure of airway patency with a second threshold. If the measure of airway patency exceeds the second threshold, indicating the airway is patent, the detected apnea/hypopnea is deemed central, and the method 45000 proceeds to step 45600; otherwise, the apnea/hypopnea is deemed obstructive, and the method 45000 proceeds to step 45500.

At step 45300, the central controller 423000 compares the measure of flow limitation with a third threshold. If the measure of flow limitation exceeds the third threshold, indicating inspiratory flow is limited, the method 45000 proceeds to step 45500; otherwise, the method 45000 proceeds to step 45600.

At step 45500, the central controller 423000 increases the base pressure P0 by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 cmH2O and 25 cmH2O respectively. In other implementations, the pressure increment $\Delta P$ can be as low as 0.1 cmH2O and as high as 3 cmH2O, or as low as 0.5 cmH2O and as high as 2 cmH2O. In other implementations, the maximum treatment pressure Pmax can be as low as 15 cmH2O and as high as 35 cmH2O, or as low as 20 cmH2O and as high as 30 cmH2O. The method 45000 then returns to step 45200.

At step 45600, the central controller 423000 decreases the base pressure P0 by a decrement, provided the decreased base pressure P0 would not fall below a minimum treatment pressure Pmin. The method 45000 then returns to step 45200. In one implementation, the decrement is proportional to the value of P0-Pmin, so that the decrease in P0 to the minimum treatment pressure Pmin in the absence of any detected events is exponential. In one implementation, the constant of proportionality is set such that the time constant $\tau$ of the exponential decrease of P0 is 60 minutes, and the minimum treatment pressure Pmin is 4 cmH2O. In other implementations, the time constant $\tau$ could be as low as 1 minute and as high as 300 minutes, or as low as 5 minutes and as high as 180 minutes. In other implementations, the minimum treatment pressure Pmin can be as low as 0 cmH2O and as high as 8 cmH2O, or as low as 2 cmH2O and as high as 6 cmH2O. Alternatively, the decrement in P0 could be predetermined, so the decrease in P0 to the minimum treatment pressure Pmin in the absence of any detected events is linear.

2.7.2 Pressure Support Ventilation Therapy

In other implementations of this form of the present technology, the value of pressure support A in equation (1) may be positive. Such implementations are known as pressure support ventilation therapy, and may be used to treat CSR. In some implementations of pressure support ventilation therapy, known as servo-ventilation, the therapy parameter determination algorithm 43290 takes as input the current measure Vent of ventilation and the target value Vtgt of ventilation provided by the target ventilation determination algorithm 43280 and continuously adjusts the parameters of equation (1) to bring the current measure Vent of ventilation towards the target value Vtgt of ventilation. In adaptive servo-ventilation (ASV), the target ventilation Vtgt is computed from the typical recent ventilation Vtyp, as described above.

In some forms of servo-ventilation, the therapy parameter determination algorithm 43290 applies a control methodology to continuously compute the pressure support A so as to bring the current measure Vent of ventilation towards the target ventilation Vtgt. One such control methodology is Proportional-Integral (PI) control. In one implementation of PI control, suitable for ASV modes in which a target ventilation Vtgt is set to slightly less than the typical recent ventilation Vtyp, the pressure support is computed as:

$$A = G\int(\text{Vent} - Vtgt)dt \qquad (2)$$

where G is the gain of the PI control. Larger values of gain G can result in positive feedback in the therapy engine module 43200. Smaller values of gain G may permit some residual untreated CSR or central sleep apnea. In some implementations, the gain G is fixed at a predetermined value, such as 0.4 cmH2O/(L/min)/sec. Alternatively, the gain G may be varied between therapy sessions, starting small and increasing from session to session until a value that all but eliminates CSR is reached. Conventional means for retrospectively analysing the parameters of a therapy session to assess the severity of CSR during the therapy session may be employed in such implementations The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

A minimum pressure support Amin of 3 cmH2O is of the order of 50% of the pressure support required to perform all the work of breathing of a typical patient in the steady state. A maximum pressure support Amax of 12 cmH2O is approximately double the pressure support required to perform all the work of breathing of a typical patient, and therefore sufficient to support the patient's breathing if they cease making any efforts, but less than a value that would be uncomfortable or dangerous.

Other servo-ventilation control methodologies that may be applied by the therapy parameter determination algorithm 43290 include proportional (P), proportional-differential (PD), and proportional-integral-differential (PID).

In pressure support ventilation therapy modes, the base pressure P0 is sometimes referred to as EPAP. EPAP may be a constant value that is prescribed or determined during titration and hard-coded or manually entered to the RPT device 40000. This alternative is sometimes referred to as fixed-EPAP pressure support ventilation therapy. Alternatively, the therapy parameter determination algorithm 43290 may continuously compute the base pressure P0 as a function of indices or measures of sleep disordered breathing returned by the respective algorithms in the therapy engine module 43200, such as one or more of flow limitation, apnea, hypopnea, patency, and snore. This alternative is sometimes referred to as auto-EPAP pressure support ventilation therapy.

2.8 Glossary

For the purposes of the present technology disclosure, in certain forms of the present technology, one or more of the following definitions may apply. In other forms of the present technology, alternative definitions may apply.

2.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

2.8.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

2.8.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including cmH2O, g-f/cm2, hectopascal. 1 cmH2O is equal to 1 g-f/cm2 and is approximately 0.98 hectopascal. In this specification, unless otherwise stated, pressure is given in units of cmH2O. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as 10-12 watt.

Sound Pressure: The local deviation from ambient pressure at a given time instant as a result of a sound wave traveling through a medium. Sound pressure is usually given in decibels SPL, that is, decibels relative to a reference pressure, normally taken as 20×10−6 Pascal (Pa), considered the threshold of human hearing.

2.8.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP: a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

Ventilator: A mechanical device that provides pressure support to a patient to perform some or all of the work of breathing.

2.9 Relevant Human Anatomy
2.9.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 2.9.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

2.9.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

2.10 General Terms

2.10.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

2.10.2 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved two-dimensional structure preferably having bending, tensile and compressive stiffness, for example, a portion of a mask that forms a curved structural wall of the mask. Preferably, compared to its overall dimensions, it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

2.10.3 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

2.11 Patient Interface Customisation

2.11.1 Customisation Overview

Customised patient interfaces may be manufactured using rapid prototyping manufacturing techniques (e.g. 3D printing). In the following embodiments, customisation may be of the entire patient interface system or may be of at least one patient interface component (e.g., a seal-forming structure 3100, frame 11001, positioning and stabilising structure 3300, etc.).

Such customisation may provide a personalised experience by forming a patient interface that specifically fits the patient. Better fit may include superior sealing, more comfort during wear, and/or optimised performance, for example, by avoiding seal disruptions, as compared to conventional mass produced injection-moulded patient interfaces.

Figure 4:
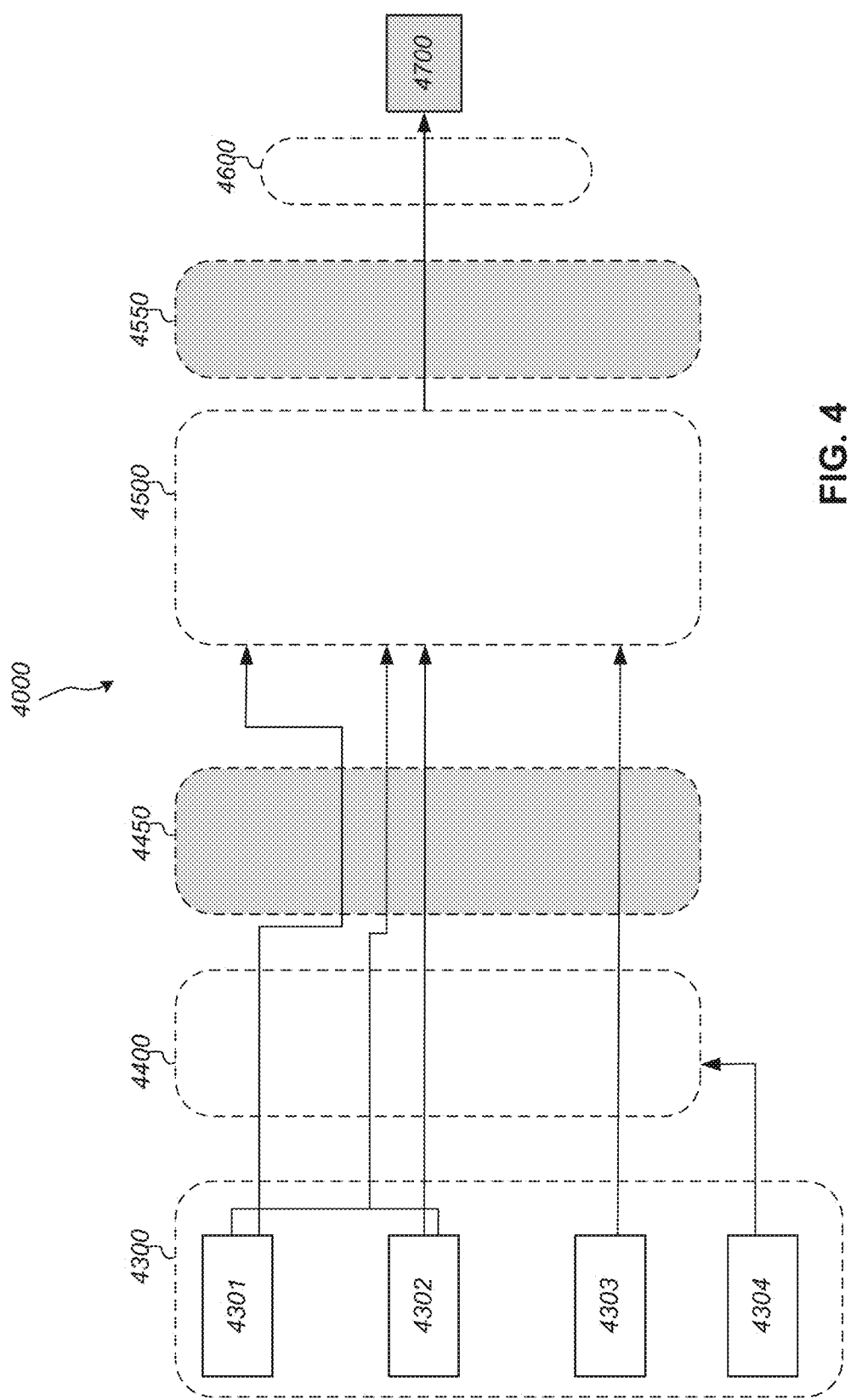
FIG. 4 is a flowchart summarising the steps of creating a customised patient interface.

FIG. 4 is a flowchart summarising the general steps of creating a customised patient interface. Each of these steps will be discussed in greater detail below. It will be understood that not every step in the flowchart is necessary and that steps may be eliminated or repeated as desired. Additionally, certain steps indicate alternatives to one another.

Patient interface customisation method 4000 generally includes the steps of data collection 4300, data processing 4400, patient interface design 4500, and patient interface manufacturing 4600. As shown, data collection may include several data collection techniques 4301, 4302, 4303, 4304, which may be utilized in concert or as alternatives. Several outputs are generated after various steps including: output data packages 4450, complete patient interface design package 4550, and final product 4700.

2.11.2 Data Collection 4300

A customised patient interface is one that has been optimised either visually, as per the patient's preferences, or geometrically optimised to suit the patient's unique facial construct or a combination of both. In order to create a custom patient interface for each unique individual patient, collections of data may be collected as shown in FIG. 4. Relaxed state data collection 4301 refers to data, such as three-dimensional data of the patient's face obtained in a relaxed, undeformed state. Deformed state data collection 4302 refers to data collected from the patient's face to indicate areas that deflect when under the load of a patient interface or other deflections due to different patient sleeping positions (e.g., lying on back, side, front, etc.). In addition to patient data relating to geometry, pressure data may also be gathered via a pressure mapping techniques 4303 to ensure proper sealing of the patient interface during use. User inputs 4304, such as varying user preferences for aesthetic, comfort or functionality may also be collected. Each of these data collection techniques are independently discussed in greater detail below.

2.11.2.1 Relaxed State Data Collection 4301

Figure 5:
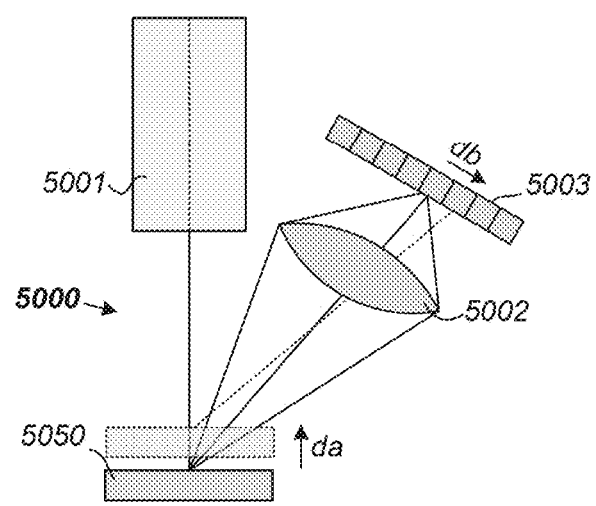
FIGS. 5, 6 and 7A-B illustrate various methods of acquiring patient data.
Figure 6:
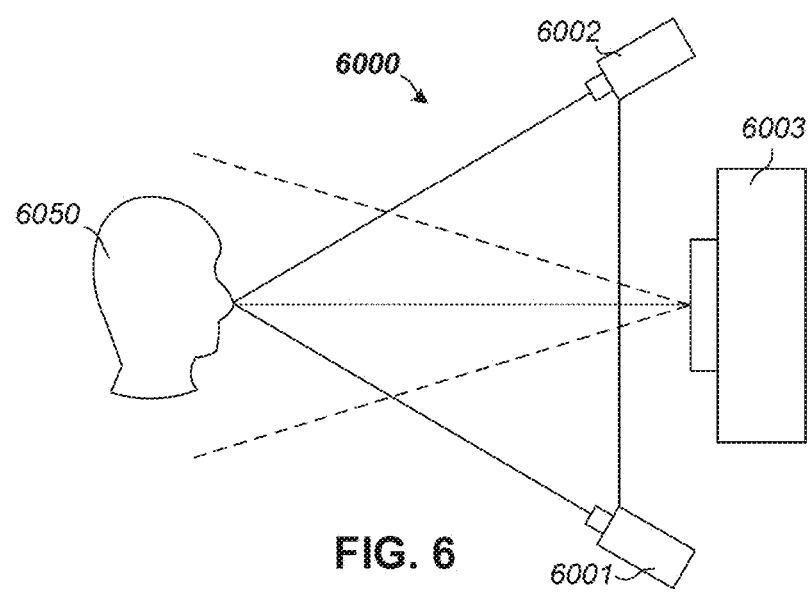

FIGS. 5-7 illustrate various methods of acquiring patient data. Collected data may include facial data, head data, and/or facial bone data of a patient and may be collected by a 3D scanner or any type of scanning device (contactless methods), or by contact methods (memory material, mechanical rods, etc.).

FIG. 5 illustrates one method of data collection that includes laser scanning. Generally, in this method, time-of-flight and triangulation methods are used to scan 3D surfaces of objects. As shown, a laser scanning system 5000 may include a laser 5001, which directs a laser or light wave onto an object 5050 (e.g., a patient's head). The reflected light then passes through lens 5002 and is collected by sensor 5003, which may include a position sensing detector or a charge coupled device. As shown in FIG. 5, a change in distance da corresponds to a distance db at sensor 5003. Thus, after proper calibration, laser scanning system 5000 may be used to capture the 3D surfaces of the face (nose, cheeks, mouth, eyes, teeth, ears, etc.) as well as the general head shape. A point cloud of samples on the surfaces from the subject's face and head may then be created, the point cloud being capable of reconstruction to regenerate the relevant 3D surfaces (e.g., a surface representing the patient's forehead). In some examples, a patient may use laser scanning system 5000 at a sleep clinic, pharmacy or other locations with access to a laser scanner, and the collected data may be transferred to a patient interface designer or patient interface manufacturer.

FIG. 6 illustrates another method of data collection that includes passive stereo photogrammetry. In this method, multiple linked cameras 6001, 6002 capture multiple still images of the subject 6050 and estimate the three-dimensional coordinates of points on an object. Estimated coordinates may be determined by measurements made in two or more photographic images taken from different positions from cameras 6001, 6002. Common points may then be identified on each image and a line of sight (or ray) may be constructed from the camera location to the point on the object. The intersection of these rays (triangulation) may help determine the three-dimensional location of the point. Thus, key features on the images are determined and the 3D point cloud may be generated on display 6003. In use, patients 6050 may take multiple photos or videos of their head and face (nose, cheeks, mouth, eyes, teeth, ears, etc.) from different angles. These images are then processed to generate the 3D model of the patients head and face. In some forms, one or more 'targets' of predetermined shapes or patterns may be used as references for the photogrammetry system, for example by temporarily placing them on the patient while measurements are taken.

Another method of data collection may include white-light interferometry, also referred to as white-light scanning. In this method, a white light is projected onto a surface of the object which is to be measured, such as a face. A measurement of the resulting interferometric pattern is obtained by a measuring system (such as a camera), and processed to obtain a three dimensional profile of the object such as the patient's head and face.

In some examples, remote data collection may be possible. For example, patient 6050 may take his own photos and send hard and/or soft copies to the designer and/or manufacturer for processing. With proper calibration, the resolution and accuracy of the method is sufficient for the application in designing custom fit patient interfaces. Thus, quick and efficient collection from patient 6050 is possible via passive stereo photogrammetry.

Additionally, existing technology may be used to provide proper calibration. For example, certain entertainment systems, such as the Xbox Kinect, include the ability to take accurate facial scans using this technique without the need of further calibration. Thus, software may be provided to enable patients to "plug and play" an Xbox Kinect into their computer or other processor, follow simple steps to have a scan taken and then sent to a designer and/or manufacturer for further analysis and design.

The previous two methods may be classified as contactless methods of measurement. Contact methods may also be used in data collection alone or in combination with contactless methods. Contact methods of data collection may involve physically placing a patient's face against a device, which plastically deforms to capture a surface. The data type collected may be a cloud point data set.

Figure 7A:
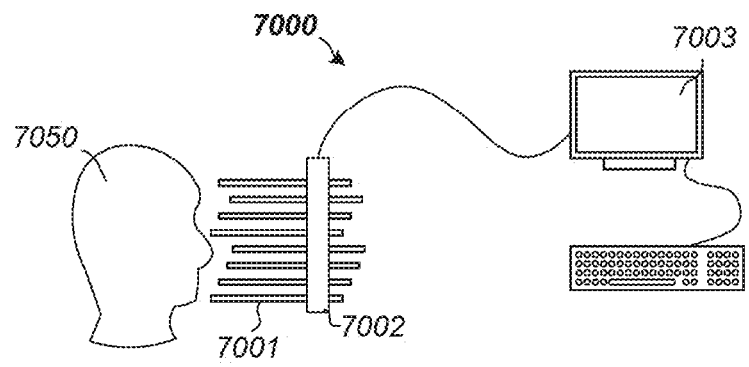

FIG. 7A illustrates one example of a contact or tactile data collection system 7000 for data collection. Data collection system 7000 may include thin rods 7001 like a mechanical pin map. Rods 7001 may be coupled to linear encoders and/or force sensors 7002 capable of measuring the distance traveled by each rod 7001 and passing the collected data to a processor 7003. Also, the encoder or force sensors 7002 may be capable of measuring the resistance force to the movement of the rods 7001. Variations are possible, including substituting a deformable or deflectable fabric for rods 7001. In further examples, a rod 7001 may be configured to measure a pressure applied between the rod 7001 and the face. Furthermore, the rod 7001 may be configured to deform according to a force or pressure between the rod 7001 and the face.

In one form, the rods 7001 may be biased, for example by springs, towards the surface of the face of the patient. The bias may assist in maintaining engagement between the face of the patient and the rods 7001, while preferably the force of the bias is sufficiently small so that it does not affect the measurement. For example, the biasing force may be set so that it is overcome typically after the face is deflected by 0.1 mm by the rod 7001. In one form, the biasing force of each rod 7001 may be approximately 0.5 N, however the biasing force may be varied to suit a particular data collection system 7000, such as a density of the rods 7001, diameter of each rod 7001 or a shape of each rod 7001.

Measuring the resistance to the movement of the rods 7001 may help determine whether the face shape is 'relaxed' or 'deformed'. That is, high resistance may indicate that the point on the face has already reached a deformed state, while a low resistance may indicate a relaxed state. The resistance information may help predict the thickness of the underlying soft tissue and/or the maximum surface deflection in that area. This gives the ability to characterise the properties of the soft tissue and therefore may be an input value for custom patient interface production. Additionally, rods 7001 may be controlled to resist plastic deformation by mechanical and electrical methods. Mechanical methods may include increasing and decreasing the friction experienced on the rods 7001 via contact or encasing the rods 7001 in viscous fluids when they move. Electrical methods may include software that controls magnetic fields or piezoelectric materials resisting the metallic rods moving. In reverse, the force of the rods 7001 may be supplied and controlled so that when the rods 7001 are placed onto the face, the rods 7001 deform the face surfaces, and therefore the deformed state data can be collected.

The rods 7001 may additionally, or alternatively, characterise a mechanical property of the face of the patient, such as an elastic modulus. For instance, a rod 7001 may measure a force (or pressure) between the rod 7001 and the face, as well as the magnitude of deflection of the face in a direction of travel of the rod 7001. Using such a method, the rod 7001 would characterise the modulus of the face along the direction of travel of the rod 7001, which may not be a constant value. For example, the elastic modulus of the face at zero deformation may be different to where the face has been depressed by 1 mm by the rod 7001, and yet again to where the face has been depressed by 2 mm by the rod 7001. In some forms, a set of relationships (e.g. a function, a table, or a curve) may be produced using the above method to characterise a potentially non-linear modulus of the face in one or more directions as desired. Such a set of relationships may be then used to model a behaviour of the face under load (e.g. using a finite element modeling software) as will be described in further detail below.

Each rod 7001 may comprise a patient end configured to accurately measure the characteristic of the patient's face as desired, while not being so uncomfortable that it may discourage the patient from using the data collection system 7000. In one form, the patient end of the rod 7001 may comprise a dome shape, or a flat disc shape. The force, or pressure, measured by each rod 7001 may vary according to the particular shape of the patient end of the rod 7001. For example, where a dome shape is used, as the rod 7001 comes in contact with the patient's face, the area in contact with the face (contact area) would be effectively a very small point at the tip of the dome. As the rod 7001 continues to travel and deform the surface of the face, the size of the contact area may increase until the entire surface of the dome is in contact with the face. Conversely, where a flat shape (e.g. disc) is used, any curvature present on the face of the patient may lead to a point contact.

Preferably, the shape of the patient end of the rod 7001 (e.g. curvature and radius in case of a dome, or a radius if a flat disc) is such that a size of the contact area is known, or able to be determined, so that any effects due to a change in the size of contact area may be taken into account.

In some cases, minimisation of a number of rods 7001 may be desired, for example to reduce costs of producing the data collection system 7000. In one example, the rods 7001 may be placed in an array with a varying density to reduce their numbers. The data collection system 7000 may comprise a higher density of rods 7001 where the resolution of measurement to be obtained is required to be higher, such as in areas where a curvature of the face is expected to be greater than in other areas. For example, rods 7001 may be placed with a higher density in areas of the data collection system 7000 to be placed on the patient's cheek, and with a lower density of rods 7001 around areas of the data collection system 7000 to be placed on the patient's upper lip.

In one form, the data collection system 7000 may be arranged to characterise the face and the head in a single direction, such as by arranging the rods 7001 in the single direction. However, in other forms, the rods 7001 may be arranged in varying directions in the data collection system 7000 to characterise the face and the head in a plurality of directions, such as an expected direction of engagement between the face and the patient interface cushion in each region. For example, the direction of the rods 7001 around the area of the data collection 7000 for the patient's lower cheek may be different to the direction of the rods 7001 for the patient's upper cheek, or the nose bridge. In some forms, the data collection system 7000 may comprise a plurality of rods 7001 configured to characterise the same region of the face in different directions. For example, one rod 7001 may characterise a modulus along the anterior/posterior direction, while another rod 7001 characterises a modulus in the same location along the left/right direction.

In one example, the supplied resistance may mimic patient interface contact pressures and CPAP pressures within the patient interface (e.g. 2-40 $cmH_2O$). Thus, the deformed state of a patient's face and head may also be captured. Furthermore, by characterising the behaviour of the face and the head as it deforms under load (i.e. pressure/force), customisation of the patient interface may be possible to allow for a change in a pressure provided in the patient interface. In some cases, measurements of a patient's face or head for may be performed prior to titration of the patient to determine an appropriate treatment pressure (or pressure range). In such cases, characterisation of the face and the head (e.g. elastic modulus) over a range of conditions (such as extent of deformation) may better allow an appropriate customised patient interface to be produced when the patient is titrated. Contactless methods may be performed at a sleep clinic or pharmacy. Alternatively, a device may be shipped to a patient to collect the data and returned to the designer after usage.

Additional medical imaging techniques may also be used to capture 3D images of the patient's facial and head structure. These may include but are not limited to CT scans, ultrasound and MRI. Thus, the same set of images that may have been generated during diagnosis may be used to compute and provide a 3D surface model of a patient's head and face (nose, cheeks, mouth, eyes, teeth, ears, etc.). Such a method may also include the added benefit of capturing not only the surfaces, but also the underlying soft tissue and bone structure, which may be used to further improve the design of the patient's patient interface.

Figure 7B:
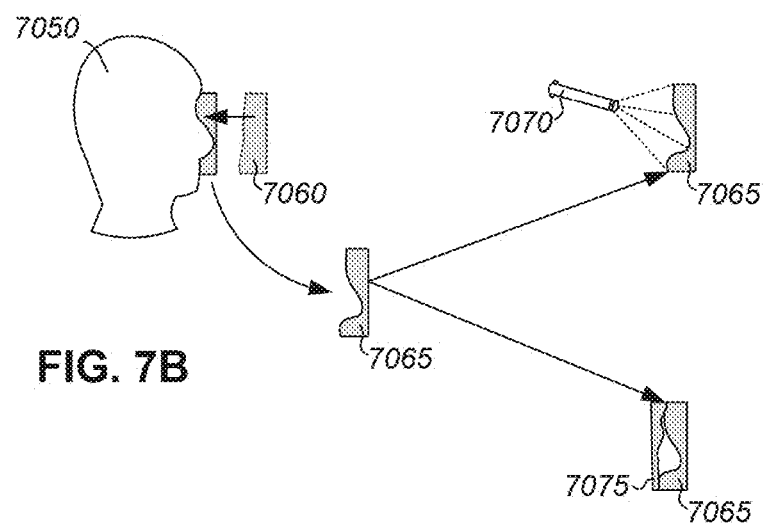

As shown in FIG. 7B, another embodiment of data collection includes taking a cast or creating a mould of the patient's face 7050, capturing their individual facial features as an imprint within a cast material. Such an embodiment could use a cast material such as a plaster, a thermoset plastic or a room temperature vulcanising silicone. Cast material 7060 may be initially malleable such that it is applied to the patient's face 7050 to form imprint then later solidifies to permanently store the individual facial geometry of the patient's face in mould 7065. The process of casting the patient's face to form mould 7065 is considered a preliminary process.

Once mould 7065 of patient's face 7050 has been created it is scanned using contactless or contact methods earlier described. If a contactless method is used, a digital image of the patient's face 7050 from mould 7065 is captured and recorded using scanner 7070. Alternatively, mould 7065 could be used directly within the patient interface manufacturing process as a means of delivering/moulding the unique facial features to aspects of the patient interface design. Mould 7065 could be assembled with other tooling 7075 used to create the common components of the patient interface to give the custom nature of new or existing patient interface designs. A part of mould 7065 may be extracted or cut from an entire facial mould, for example, the part corresponding to the patient's nose. This part is then placed in a tool for manufacture of the custom patient interface.

2.11.2.2 Deformed State Data Collection 4302

As discussed above with reference to contact or tactile imaging system, deformed state data collection 4302 may, in some cases, be performed using the same methods or techniques of the relaxed state data collection. A face deforming device 8001 may be useful in gathering data for deformed state data collection 4302. The force applied to the face may be tunable.

The method involves placing a rigid or semi-rigid deforming device 8001 onto the patient's skin 8050, which mimics the deformation of the face surfaces during CPAP therapy with a given headgear tension and CPAP pressure. Once deforming device is 8001 is worn, the surfaces are then captured with any of the methods described above for relaxed state data collection. Optionally, deforming device 8001 may be constructed from transparent materials to allow visual surface capturing methods (schematically shown by camera 8002) to capture the 'deformed' surfaces of the patient's face.

Deforming device 8001 may further include materials, which are easily identifiable or contrast with human tissue on medical images (e.g., radiopaque materials). Thus, on medical images, boundaries between the skin and device may be quickly identified and the deformed 3D surfaces on the patient's skin may be calculated. Deforming device 8001 may be made available at sleep clinics or sent out the patient to collect the data and return the device.

Deforming device 8001 may include materials ranging from rigid materials to silicone cushion softness. The hardness of the material may range from different grades to simulate a patient interface on the patient at 1-10N of headgear force and also CPAP pressures of between 5-45 cmH$_2$O (optimally 10-20 cmH$_2$O).

Figure 8A:
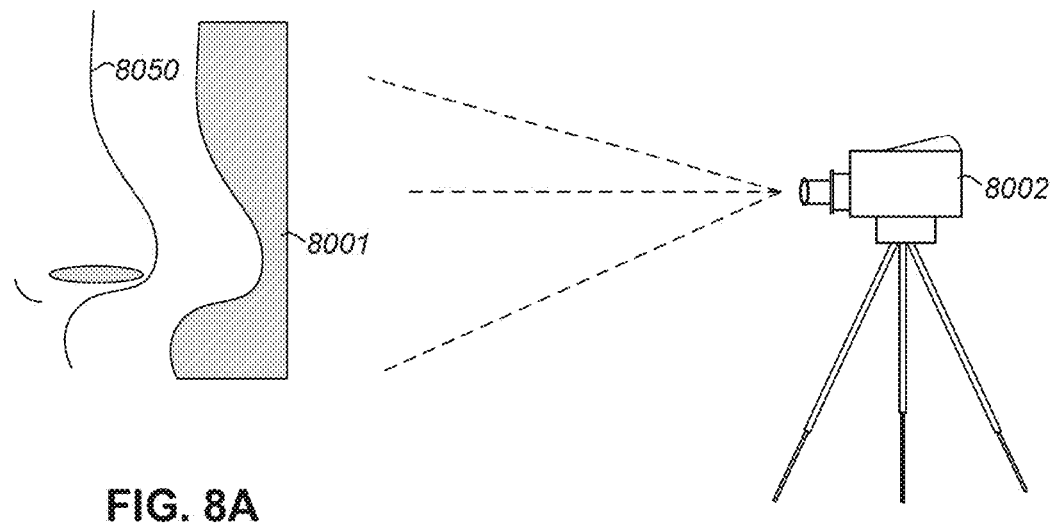
FIGS. 8A-8B illustrate additional methods of acquiring additional patient data relating to a deformed state.
Figure 8B:
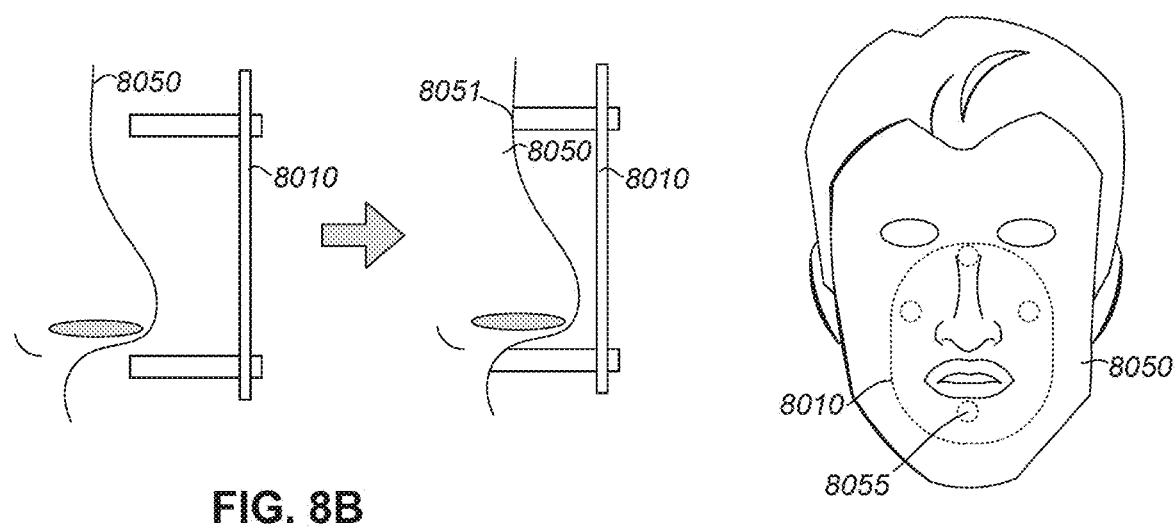
Figure 8C:
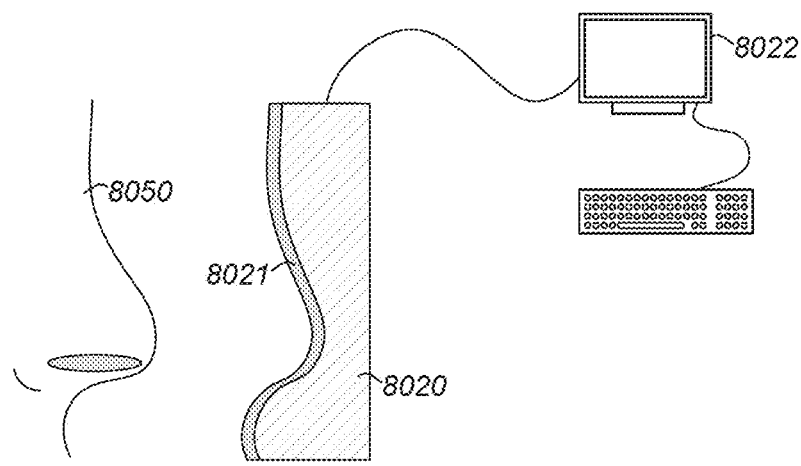
FIGS. 8C-8D illustrate methods of acquiring patient data via pressure mapping.
Figure 8D:
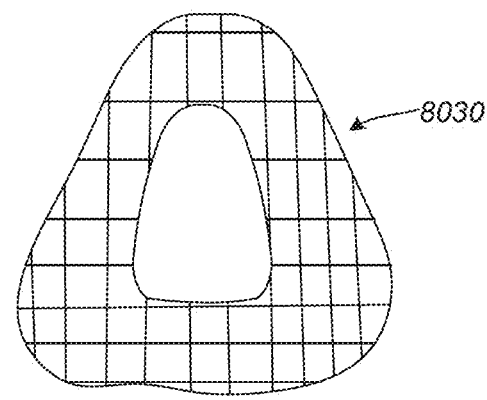

As shown in the example in FIG. 8B, deforming device 8010 may be in the form of a pusher or deflector designed to push onto the face at pre-determined locations (e.g., nasal bridge 8051) to deform the skin surface to simulate patient interface and/or air pressure. Once the deflector is onto the face, the deformed surfaces 8055 are then captured with any of the methods described above for relaxed state data collection.

The patient intending to wear the customised patient interface will most likely wear the patient interface lying down in a supine position. Given the effects gravity has on the face varies as a function of the face's alignment to the gravitational pull, it is probable that an indication of the face's surface geometry in the supine position will be desirable. This may be achieved via a scan while the patient is lying down, using any of the described techniques. Alternatively, the expected geometry of the face may be determined by applying an algorithm to the upright scan of the patient's face, the algorithm may take in to account such factors as the patient's age, sex, BMI, ethnicity and/or other factors that impact the expected magnitude of passive facial movement. This prediction algorithm may be performed using physiological modeling software such as ANSYS as will be described in greater detail below.

2.11.2.3 Pressure Mapping 4303

The pressure of a patient interface seal-forming structure 3100 on the patient may also be measured for the best fit and comfort via a pressure mapping 4303. In one example, a patient interface blank or dummy patient interface 8020 is worn and a tactile pressure film sensor 8021 is disposed between dummy patient interface 8020 and the patient's skin 8050. Pressure film 8021 may be a generic shape to fit a given patient population (e.g., adult, child, ethnicity, etc.). When dummy patient interface 8020 is worn, film 8021 may measure a grid of the pressure values experienced on the patient's face. In order to ensure an adequate seal around the perimeter of the patient interface, pressure values within a predetermined range may be targeted. Data captured in this process may include the known geometry of dummy patient interface 8020 along with a grid of pressure measurements on the patient contact surface. Such data may be sent to a computer having a processor 8022 and may be used to generate charts, tables or diagrams such as pressure map 8030 from pressure values gathered from this technique.

In some examples, dummy patient interface 8020 may include a generic nasal patient interface shape based on a population, creating a seal on the patient with relative ease. Dummy patient interface 8020 may further have a soft cushion to mimic a real patient interface on the face. In some examples, the soft cushion may include a silicone, a foam, a gel and other suitable materials.

User preferences and input may also be collected at user input 4304. This may include a variety of data relating to form, function, aesthetic, comfort or other preference and will be discussed in further detail below following the processing of data from relaxed state data collection 4301, deformed state data collection 4302, and pressure mapping 4303.

2.11.3 Data Processing 4400

The collected patient data from step 4300 may be transforming or processed in data processing step 4400 before making a patient interface for that patient. Without data processing 4400, a mirror image of a scanned face (superficial topography) may be used to create a patient interface. Such a patient interface, however, is not necessarily ideal, because certain areas of the sealing region on the face may require different levels of sealing force, or are more sensitive to tight headgear pressure, or are more likely to have a leak in that location due to complex facial geometry. These finer details relevant to performance and comfort are accounted for in data processing 4400.

Figure 9A:
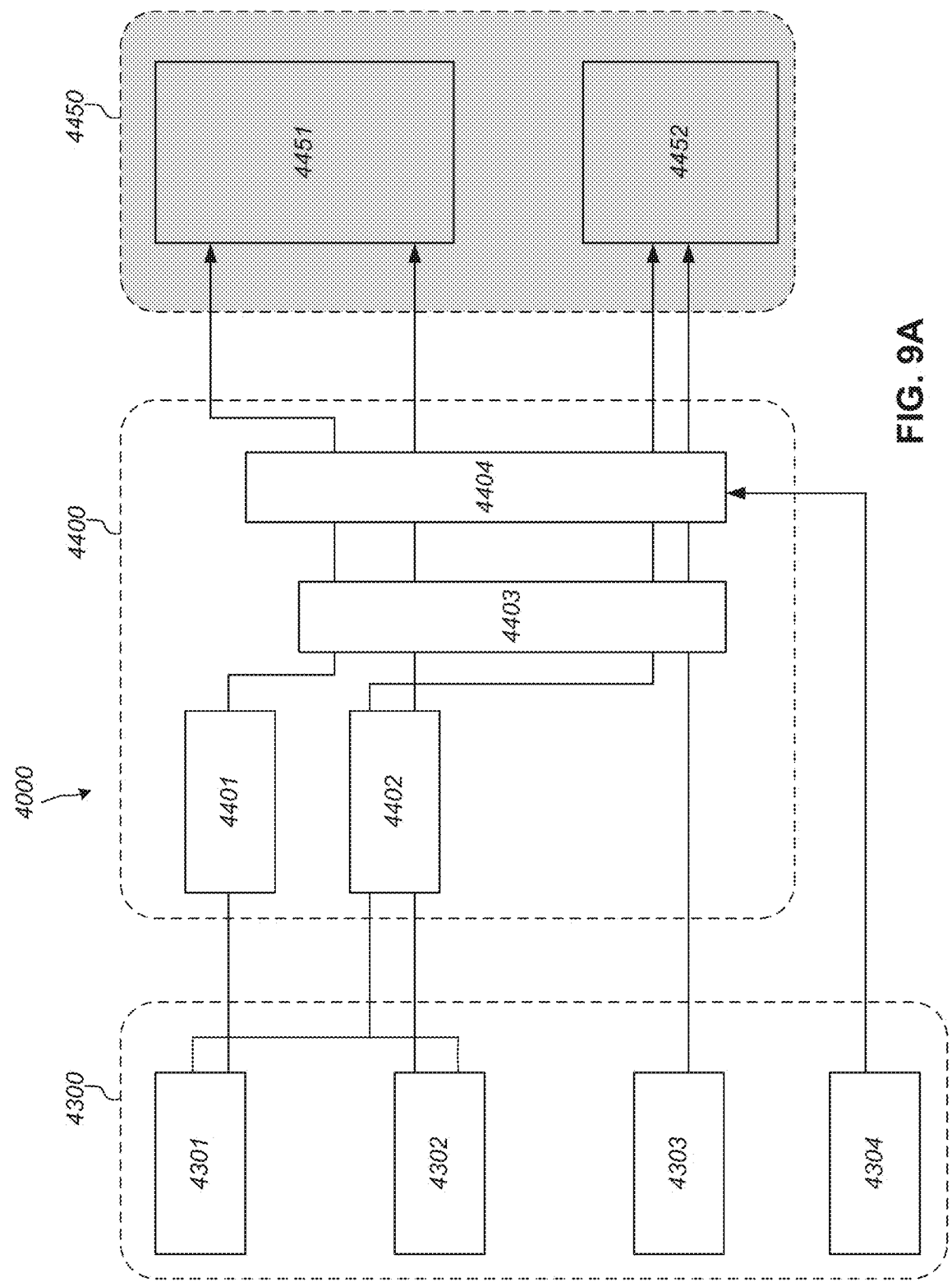
FIG. 9A is a detailed flow chart of the acquisition and data processing steps of creating a customised patient interface.

FIG. 9A is a detailed flow chart of the data collection 4300, data processing 4400, and output data packages 4450 of patient interface customisation method 4000.

In one example, the relaxed state geometry data from relaxed state data collection 4301 may be used to try and provide an indication of the deformed state geometry if it cannot be directly measured or is unavailable. Simulation software may be used in relaxed data post processing 4401 to simulate the deformed state. Examples of suitable simulation software may include but is not limited to ANSYS which performs a transformation from 'relaxed' to 'deformed' state geometry data in relaxed data post processing step 4401.

With both the 'Relaxed' and 'Deformed' states of geometry data, Finite element software (such as ANSYS) may be used to calculate approximate pressure values experienced between the patient interface contact area and the patient's face in simulating experienced pressure 4402. Alternatively, pressure data may be gathered separately via pressure mapping 4303 as discussed above. Thus, from relaxed state data collection 4301, the deformed geometry may be estimated as well as the experienced pressure, and the system is capable of providing a customised patient interface even if one or more of the data collection steps are unavailable.

With the measured data, either geometric or pressure data, areas or features on the patient's face, which require special consideration may be determined and addressed in specific feature processing 4403. Optionally, data from any combination of measurement sources may provide a comprehensive model that includes both the geometry and pressure data sets to further the goals of providing comfort, efficacy and compliance of the design.

Additionally, in order to enhance the user experience and increase patient interaction, patient interface customisation method 4000 proposes a platform through which the user has design input into the final product. This system may provide user input that ranges from minor to major design control, with or without design input from the designer and/or manufacturer, including but not limited to: aesthetics, mechanical considerations, therapy dependent variables, comfort and seal characteristics. This data is gathered in data input 4304 and processed in applying patient preferences 4404 of data processing 4400.

2.11.3.1 Relaxed Data Post Processing 4401

The face is not a static surface. Rather it adapts and changes to interactions with external conditions, such as forces from a patient interface, air pressure on the face and gravity. By accounting for these interactions, additional benefits are gained in providing the optimum seal and comfort to the patient. Three examples illustrate this processing.

First, since the patient wearing these patient interfaces will experience CPAP pressure, this knowledge may be used to enhance the comfort and sealing of the patient interface. Simulation software along with known characteristics (e.g. soft tissue properties or elastic moduli) may help predict the deformations the surfaces of the face will experience at a particular air pressure within the patient interface.

Tissue properties may be known and gathered for a population relating to any of the following facial locations: supraglabella, glabella, nasion, end of nasal, mid-philtrum, upper lip margin, lower lip margin, chin-lip fold, mental eminence, beneath chin, frontal eminence, supra orbital, lateral glabella, lateral nasal, suborbital, inferior malar, lateral nostril, naso-labial ridge, supra canina, sub canina, mental tubercle ant., mid lateral orbit, supraglenoid, zygomatic, lateral, supra-M2, mid-masseter muscle, occlusal line, sub-m2, gonion, and the mid mandibular angle.

Figure 9B:
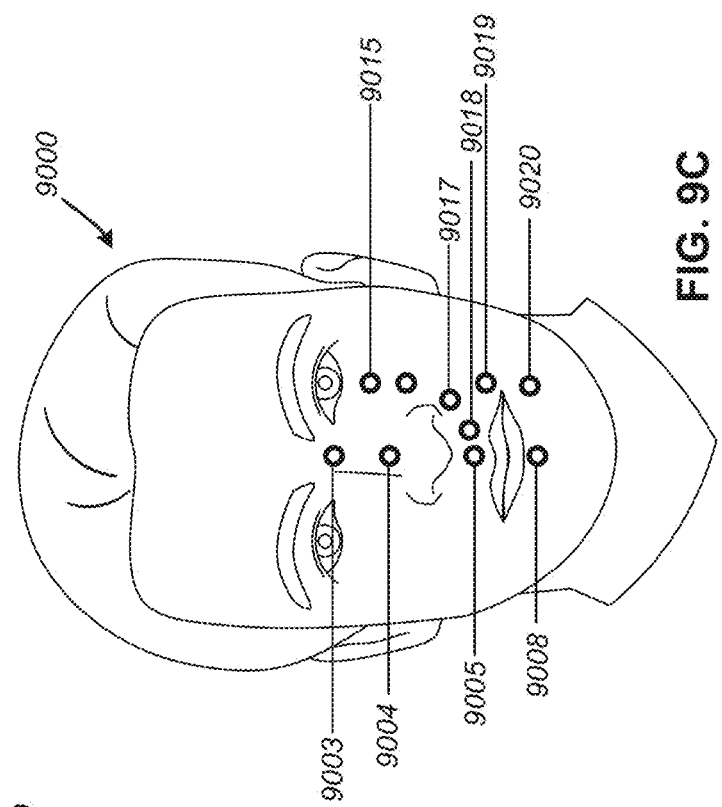
FIGS. 9B and 9C illustrate various facial areas of interest where known tissue properties may be useful.

FIG. 9B illustrates one exemplary embodiment, in which soft tissue thickness is known from anthropometric databases for at least one of the following locations of patient 9000: nasian 9003, end of nasal 9004, mid-philtrum 9005, chin-lip fold 9008, mental eminence 9009, suborbital 9015, inferior malar 9016, lateral nostril 9017, naso-labial ridge 9018, supra canina 9019, sub canina 9020. As shown in FIG. 9B, certain locations such as suborbital 9015, inferior malar 9016, lateral nostril 9017, naso-labial ridge 9018, supra canina 9019, and sub canina 9020 are disposed on both sides of the face (e.g., suborbital 9015 has a mirror-image location on the opposing side of the face, across the nose).

Known tissue properties at any one or more of these locations may include any one or more of soft tissue thickness, modulus data based on force, deflection, modulus and thickness, soft tissue thickness ratio information, and body mass index (BMI).

Second, the skin surfaces on a patient's face significantly deform when a CPAP patient interface is strapped onto a face. Using the initial 3D measurement of the geometric surfaces of the head and face in the relaxed state, the changes in the surfaces may be predicted using knowledge of the skin/soft tissue properties, discussed above, and simulation software. Such a technique may be an iterative, optimisation process coupled with the design process.

Figure 9C:
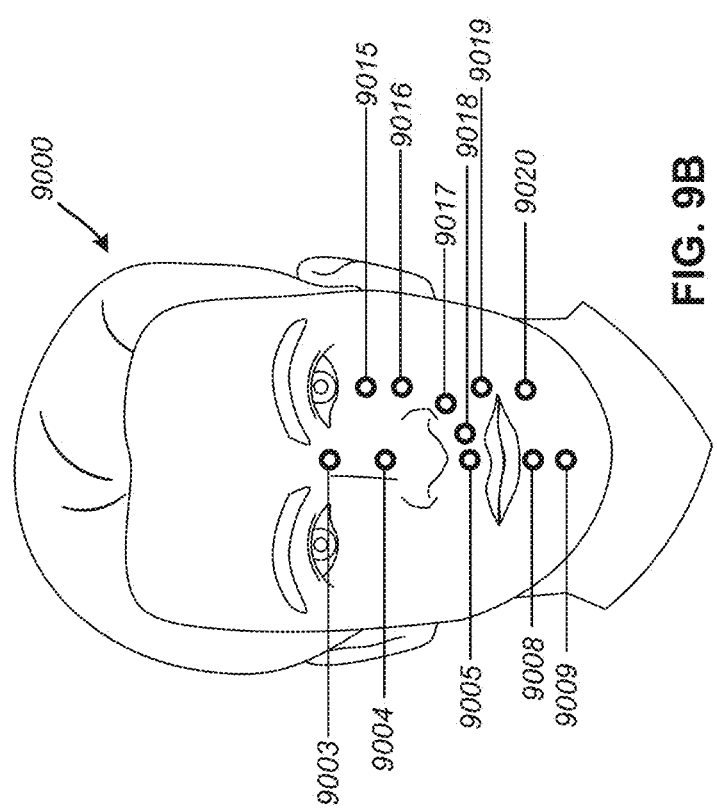

Third, given a patient's sleeping position, the skin surfaces may shift due to gravity. Predicting these changes, by utilising knowledge of skin and soft tissue properties along with simulation software, can help to design more robust comfortable and high performance patient interfaces in various sleeping positions. As shown in FIG. 9C, data relating to upright to supine change in geometry may be collected and used from one or more areas of interest such as nasian 9003, end of nasal 9004, mid-philtrum 9005, chin-lip fold 9008, suborbital 9015, lateral nostril 9017, naso-labial ridge 9018, supra canina 9019, sub canina 9020.

2.11.3.2 Simulating Experienced Pressure 4402

Finite Element Analysis (FEA) software (such as ANSYS) may be used to calculate an approximate pressure value experienced between the patient interface contact area and the patient's face. In one form, inputs may include geometry of the face in the 'Relaxed' and 'Deformed' states, characteristics (e.g. measured elastic moduli, or sub-structures with known characteristics such as stiffnesses) of the face at various locations thereof. Using such inputs, a finite element (FE) model of the face may be constructed, which could then be used to predict one or more responses of the face to an input (such as deformation or load). For example, the FE model of the face could be used to predict the deformed shape of the face for a given pressure level in the patient interface (e.g. 15 cmH$_2$O). In some forms, the FE model may further include a model of the patient interface or a portion thereof, such as a cushion, comprising a geometry of the cushion and its characteristics (e.g. mechanical properties such as elastic modulus). Such a model could predict a deformation of the cushion when an internal load is applied thereto, such as from an application of CPAP pressure, and a resulting interaction of the cushion with the face, including the loads/pressures therebetween, and a deformation of the face. Specifically, the change in distance at each point between the relaxed state and the deformed state along with the corresponding tissue properties may be used to predict the pressure experienced at a given point (e.g., at a cheekbone).

2.11.3.3 Specific Feature Processing 4403

Certain areas or features on a patient's face may require special consideration. Identifying and adjusting for these features may improve the overall comfort of the patient interface. From the data collection and estimation techniques discussed above, suitable features may be applied to a custom patient interface.

Specifically, different areas on a face may have different requirements. The table below illustrates one example of the anticipated areas of interest:

| Area on Face | Pressure Sensitivity | Pressure Compliance | Shear Sensitivity | Shear Compliance |
|---|---|---|---|---|
| Nose Bridge | HIGH | LOW | HIGH | MED |
| Sides of Nose | HIGH | LOW | N/A | MED |
| Corner of Nose (Upper Cheek) | MED | MED | N/A | HIGH |
| Sides of Mouth | LOW | HIGH | N/A | HIGH |
| Lower Corner of Nose | LOW/MED | MED | N/A | MED |
| Bottom Lip | LOW/MED | LOW | N/A | HIGH |
| Top Lip | HIGH | LOW/MED | N/A | MED |

In addition to the pressure sensitivity, pressure compliance, shear sensitivity and shear compliance indicators above, special considerations may be accorded to facial hair, hair styles, and extreme facial landmarks, such as a pronounced nose bridge, sunken cheeks or the like. As used herein, "shear sensitivity" refers to the feeling of shear by the patient, while "shear compliance" refers to how willing the patient's skin is to move along or compliant with shear.

2.11.3.4 Applying Patient Preferences 4404

In addition to the areas of interest, the synergy between a user and a designer may provide a more pleasant experience and better patient interface for the patient's needs. Such patient input may be applied in applying patient preferences 4404.

In one example, an online portal is created to allow the patient to engage in the design process. To provide the optimum comfort and performance for custom patient interfaces, creating dialogue between the patient, the designer and/or manufacturer is advantageous. One option is creating an environment where the patient can provide inputs to their patient interface design and where the designer and/or manufacturer can also provide recommendations via an online portal.

Within an online portal or smart phone application, patients may create their own personal online profile where they can perform a variety of tasks such as keeping track of therapy progress, uploading 3D data, or designing a custom patient interface through aesthetic and/or functional features. In some examples, aesthetic inputs may include choosing colours, schemes and/or patterns to appear on their patient interface system. User may also upload patterns or colours to their patient interfaces, choose material finishes (e.g., contact, frame or headgear materials) for comfort, tactility or temperature preferences, and/or choose between varieties of headgear styles. In some examples, functional inputs may include headgear elasticity (e.g., tensile strength properties), patient interface type (e.g., nasal, full face, etc.), headgear attachment points (e.g., the number of points desired, the trade-off between stability and bulkiness or the type of attachment, such as magnets), patient interface volume (bulkiness vs. breathing comfort), additional sensors in the patient interface, elbow/swivel choices, vent location and direction, whether the user wears glasses, type of skin, such as oily or dry skin. Users may also order patient interfaces or other products, and engage in social networking forums, where patients can share their CPAP experiences or patient interface designs.

Figure 10A:
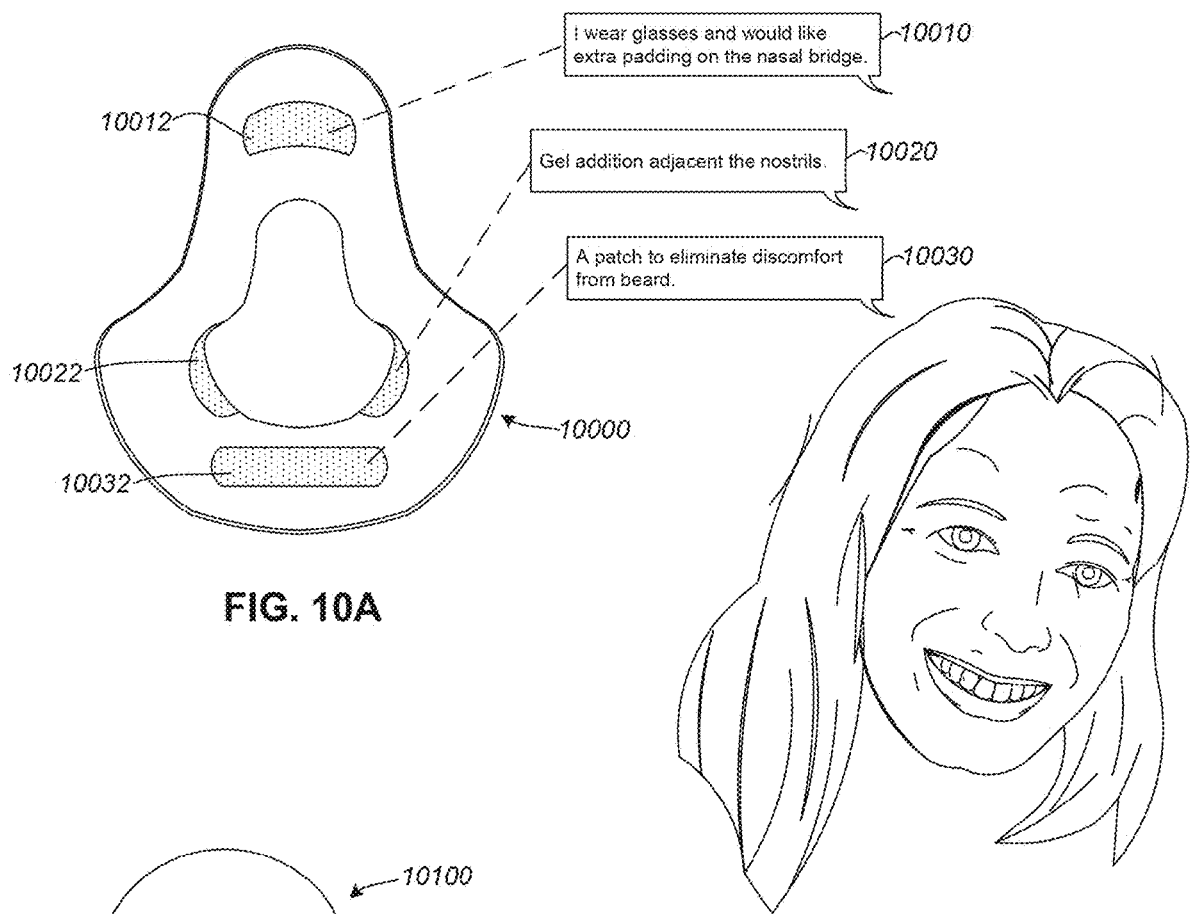
FIG. 10A illustrates one example of a nose mask that has been modified in response to patient feedback.

FIG. 10A illustrates one example of nose patient interface 10000 that has been adjusted to accommodate patient input 10010, 10020, 10030. In response to first input 10010 regarding glasses, a corresponding padding 10012 is added in the desired location. In response to second input 10020 regarding gel addition, a corresponding gel portion 10022 is added adjacent the nostrils. In response to third input 10030 regarding the beard, beard patch 10032 is added to increase comfort. Thus, these additional patient-specific criteria are considered in designing and manufacturing the patient interface.

The information may flow in both ways between the patient and the designer. That is, in addition to patient input, the designer may suggest certain features to the patient. For example, the designer may provide the range of product options as well as recommendations to the patient. Such recommendation may be based on queries to the patient, device usage data, such as data relating to leak, hours of usage, or data from the collected data (e.g., geometric surfaces or pressure maps), such as skin tone and colours to generate aesthetically pleasing patient interfaces, patient interface size and type, and/or headgear structure from the head shape. Elbow/tube type and orientation may also be considered and a recommendation relayed to the patient regarding same.

Figure 10B:
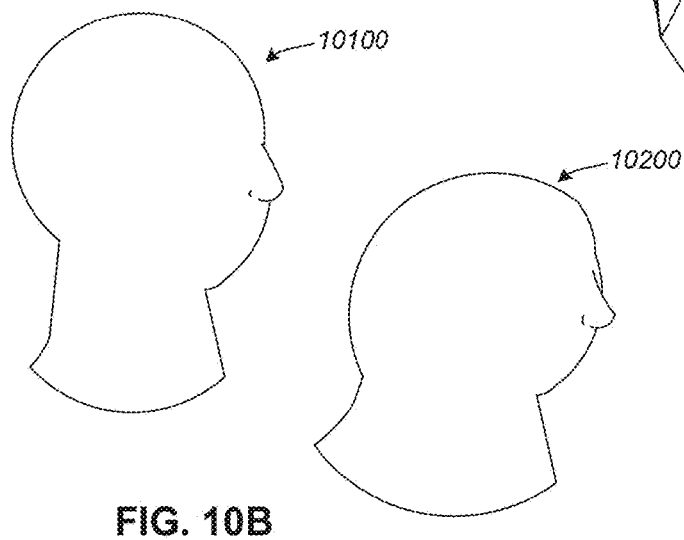
FIG. 10B illustrates differences in head shape.

Thus, the designer and/or manufacturer may recommend different headgear for patient 10100 and patient 10200 of FIG. 10B based on the differences in their head shapes to increase stability of the patient interface. Additionally, a specific headgear, which may not be suitable for patient 10200 may be indicated as a poor choice due, for example, to anticipated discomfort.

Figure 10C:
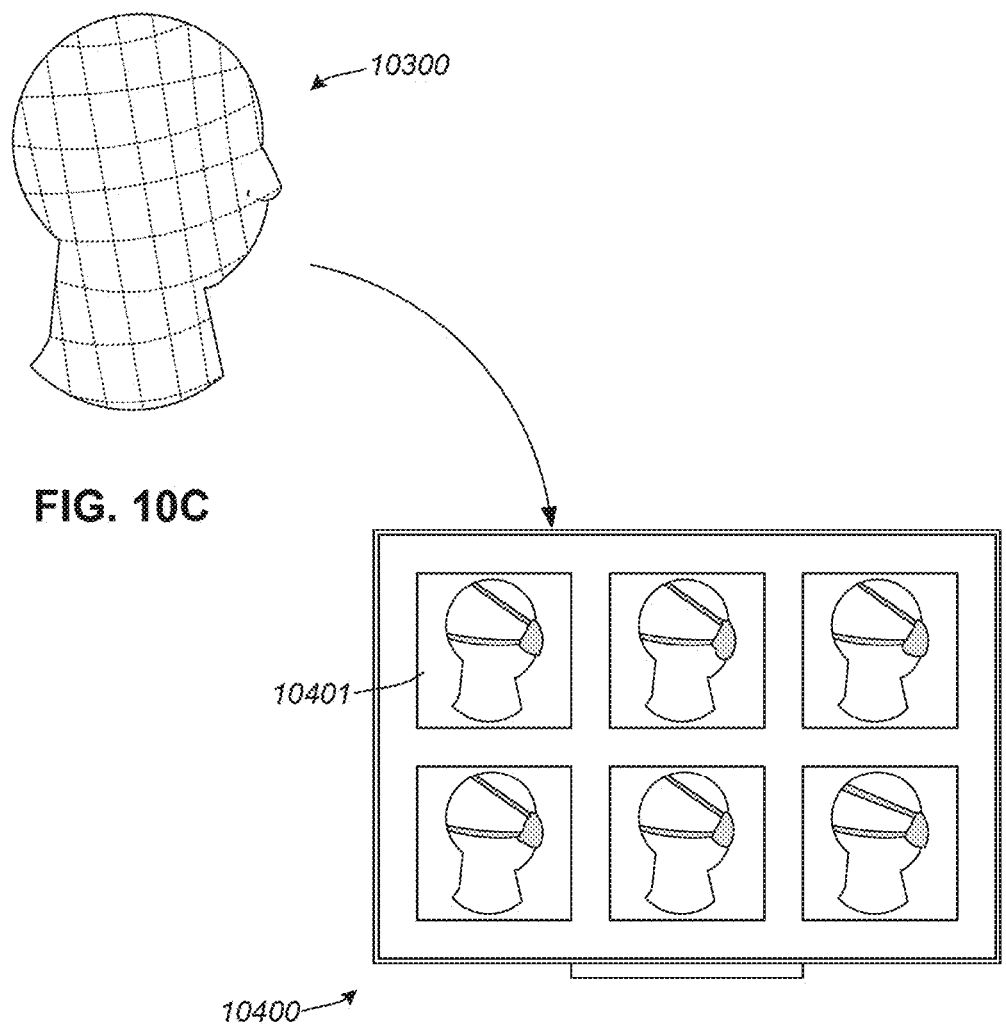
FIG. 10C illustrates a system of acquiring patient data and providing several mask options to the patient.

The proposed system may also provide a feedback tool by which the person is able see their customised design placed on to a 3D rendering of their face to create a virtual rehearsal shown in FIG. 10C. Thus, in one example a patient's head 10300 is scanned and data is sent to a virtual portal 1400 where it is rendered on a number of patient interfaces 10401. The user may choose a specific type of patient interface or a type of headgear, as well as adjust a plurality of parameters such as style, colour, etc. After completion, the patient may then print a picture of the design rendered on the face (or the design alone) and send the chosen design for further processing and/or manufacturing.

2.11.4 Output Data Packages 4450

As used herein "Data Package" refers to the data packet that is used as the input for the process of designing the patient interface. Within the Data Packages are several subsets of data including, the data that has been captured at patient data collection 4300, the enhanced version of the data after specific feature processing 4403 and the user inputs 4304.

These data packages contain all the input information required for the design of the patient interface in patient interface design 4500. Patient interface design 4500 may include algorithms that utilize the data packages as an input to create a customised patient interface design that responds directly to the information within the data package. Alternatively, the data package may be used directly by designers to create the custom patient interface design, a high labour but fully handmade method. The data packages can be stored for future use if needed. Two data packages have been briefly discussed. These include a geometric surface model design package 4451 and a pressure map design package 4452.

2.11.4.1 3D Geometric Surface Model Design Package 4451

A three-dimensional geometric surface model design package 4451 may consist of the 3D geometric surface model of the patient's face and head after the capture data has been processed in data processing 4400. Alongside this 3D model, the package may also contain the patient preferences and inputs that they have specified.

2.11.4.2 Pressure Map Design Package 4452

Pressure Map Design Package 4452 may include a pressure map of the patient's face after the capture data has been processed in data processing 4400. Alongside this pressure map, the package may also contain the patient preferences and inputs that they have specified.

2.11.5 Patient Interface Design 4500

Patient interface design 4500 may include a system of algorithms that process data packages 4451, 4452. Patient interface design 4500 acts as a smart system that responds to the inputs, which are the data packages, and calculates the output as the designed custom patient interface from that particular data package. Thus, patient interface design 4500 will take the incoming data packages and use the data (either 3D geometric surfaces and/or 2D pressure map) along with the patient preference inputs and calculate at least one custom component.

Figure 11:
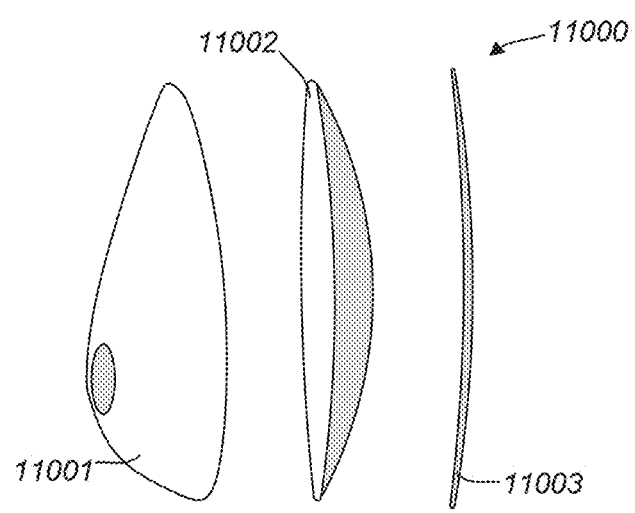
FIG. 11 is a schematic illustrating the three components of a mask.

FIG. 11 is a schematic illustrating the basic elements of patient interface 11000. The basic patient interface structure 11000 may be separated in to three main parts, each of which can be either standardised or customised individually, concurrently or in any combination as required. As shown, patient interface structure 11000 includes frame 11001, intermediate structure 11002 and sealing element 11003.

Frame 11001 is generally considered the component that provides an offset distance from the patient's face and an associated functional dead space; it is also the component to which the pneumatic connection from the flow source is most likely to be made. Intermediate structure 11002 has several functions. First, intermediate structure 11002 aids in offsetting frame 11001 from the face. It also provides an attachment method for frame 11001 and sealing element 11003. It may provide a geometric transition between a standardised frame and custom sealing element 11003 or vice versa. Intermediate structure 11002 may also be customised through either geometry or material properties to provide improved user comfort/efficacy of treatment. Sealing element 11003 consists of either a geometry designed into an elastomer to achieve a seal (e.g., a membrane, similar to that of current patient interface designs) or a material of appropriate properties that enable a seal such as a soft elastomer, foam, gel, textile and/or a sticky/tacky material.

2.11.5.1 Frame Customisation

Figure 12A:
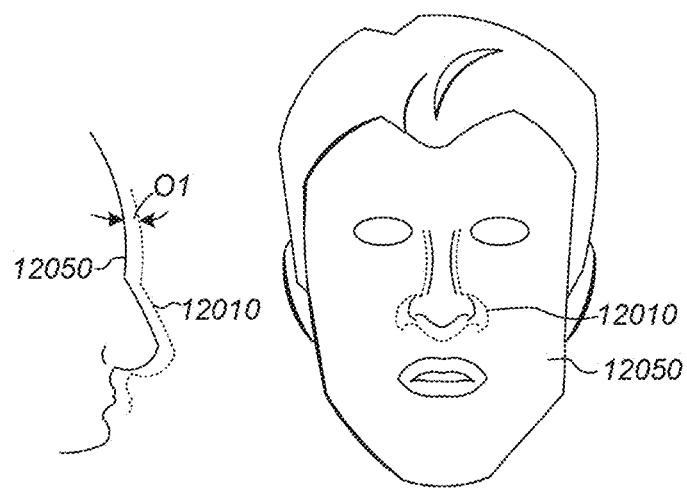
FIGS. 12A-F illustrate several examples of frames and methods for creating same.
Figure 12B:
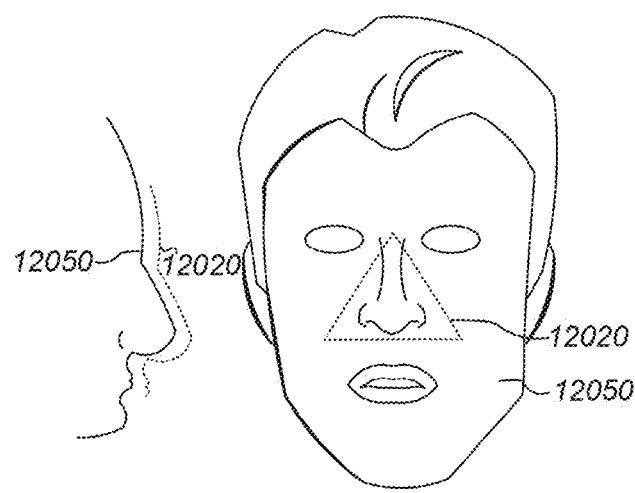
Figure 12C:
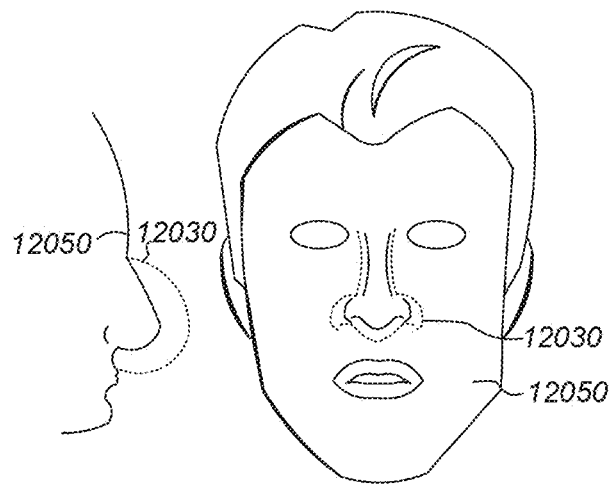

To increase functionality and comfort, frame 11001 may be customised in a variety of methods. Three such methods will be described with reference to FIGS. 12A-C. It will be understood, however, that the customisation is not limited to these three examples and that variations of each example are possible.

In a first example (FIG. 12A), a patient's face 12050 is scanned using any of the techniques discussed above in data collection 4300. An algorithm may then offset and trim surfaces such as, for example, non-sealing surfaces of the patient's face 12050, to produce a patient interface frame 12010 that is a transformed copy of the patient's face, offset by a predetermined offset value, O1. In some examples, the offset value O1 is between about 0 mm and about 20.0 mm. In at least some other examples, the offset value O1 is between about 5.0 mm and about 10.0 mm. The offset value O1 may be variable around the face or constant. Thus, in some examples, a constant offset value O1 of 5.0 mm is applied to each point of the patient interface. Alternatively, the offset value O1 may vary such that an initial offset value O1 of 5.0 mm is applied adjacent the nose, and a different offset value O1 of 6.0 mm is applied near the cheekbones. In this example, functional dead-space and vent flow requirements may be controlled (e.g., functional dead-space and vent flow requirements may be reduced or increased). The resulting patient interface may also be made compact, limiting visual obstructiveness. Contact pressure may be evenly distributed and stability may be increased. Headgear tension may also be reduced in this manner. The increased contact area may also improve sealing as will be discussed in greater detail below.

If the offset value O1 is set to 0 mm, frame 12010 of the patient interface may sit in full contact with the patient's skin. In this contact, in order to increase comfort, the patient interface may be unitarily formed from one portion. As such frame 12010 may be made from a soft or elastomeric material, unlike 'traditional' frames. In this example, the nares or nostrils may act as fixture points.

In a second example (FIG. 12B), a patient's face 12050 is scanned and an algorithm copies and offsets relevant surfaces to create a custom frame assembly 12020 having a shape in the sagittal plane that blends these surfaces into a standardised cushion interfacing surface. This technique may reduce the functional dead space as well as the vent flow requirements. The resulting patient interface may also be made compact, limiting visual obstructiveness. This example may also provide a more standardised lock/key interface between frame 12020 and a corresponding intermediate structure or sealing element 11003 resulting in improved manufacturing economy because only certain inserts may need to be customised as opposed to customising the entire apparatus.

In a third example (FIG. 12C), a patient's face 12050 is scanned and an algorithm copies and offsets relevant surfaces to create a custom frame assembly 12030 having a shape in the coronal plane that blends these surfaces into a standardised tube/elbow attachment point. This technique may evenly distribute contact pressure, increase stability, reduce headgear tension and allow for standardisation similar to frame 12020. Thus, frame 12030 may provide a lock/key interface with various elbows/short tubes, or use an existing array of elbows (e.g., choose one of three or more elbows). Custom elbows may also be created, if desired.

Existing frames/headgear combinations may also be used without being customised. In these examples, intermediate structures and/or sealing elements 11003 may be customised and coupled to a standardised frame, or an array of standardised frames. In the following examples, one less component is customised resulting in a decreased price and improved manufacturability.

Figures 12D, 12E, 12F:
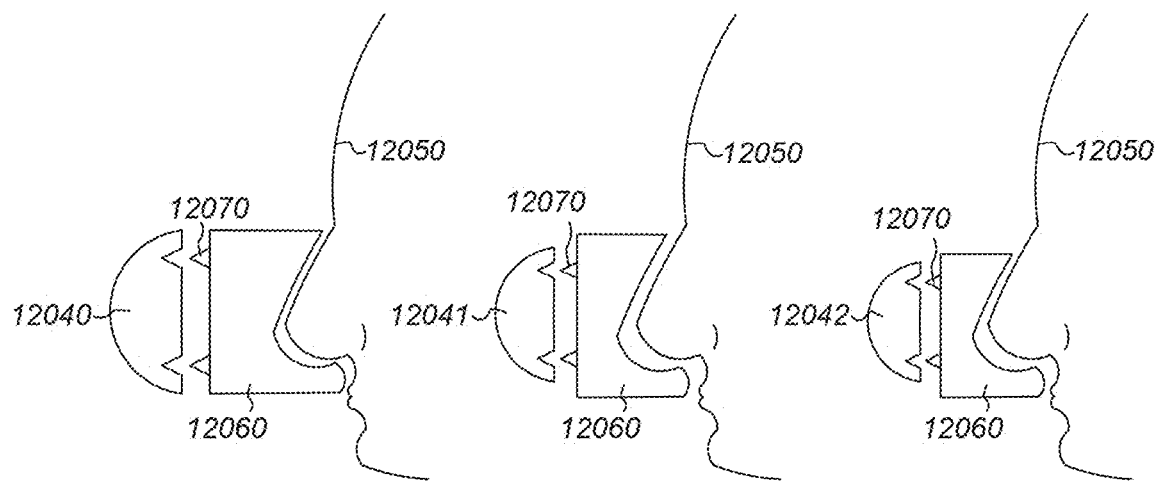

In FIGS. 12D-F, three standardised frames 12040, 12041, 12042 are presented to users. Based on data collection 4300, an algorithm may decide which of standardised frames 12040, 12041, 12042 best suits the patient. Customised intermediate structures and/or sealing elements 11003 may then be separately formed and configured to interlock with the standardised frames. The appropriate frame may be chosen based on face size and may include keyed interlock systems 12060 for mating with other customised components 12070 of a patient interface.

2.11.5.2 Intermediate Structure Customisation

Figure 13A:
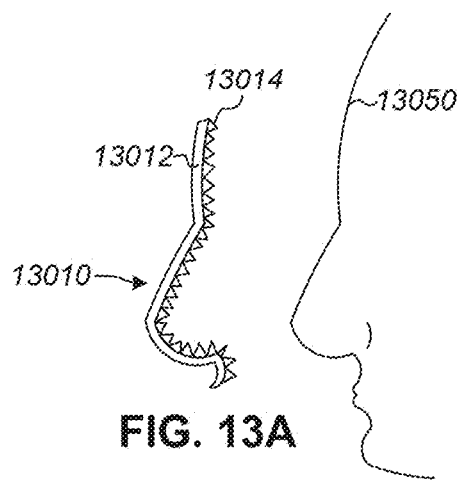
FIGS. 13A-D illustrate examples of intermediate layers that are capable of attaching to a frame, and sealing layers that are capable of attaching to the intermediate layer.

As with the frame, intermediate structure 11002 may also be either standardised or customised. To achieve optimum comfort and seal, the intermediate structure can be customised from the patient data to provide macro and/or microfit to the patient. As used herein, a microfit is a relatively small adjustment by the sealing surface or material to accommodate deformations by less than or equal to 2 mm. An example for the intermediate structure 11002 capable of performing this function is one made of foam or soft durometer silicone. Moreover, a macrofit is a relatively larger adjustment by the sealing surface or other patient interface components to accommodate deformations greater than 2 mm. An example for the intermediate structure 11002 capable of performing this function is higher durometer silicone (or thicker) or foam displacement. Thus, in one example (FIG. 13A), intermediate structure 13010 may include two components adjustable for macrofit and/or microfit. A first component 13012 may be formed of a rigid or semi-rigid material to provide the proper macrofit. In some examples, the material of first component 13012 may include plastics, thermoset or thermoplastic elastomers or any other suitable polymer or combinations thereof. For finer adjustments (e.g., a microfit), a second component 13014 may be fabricated and coupled to first component 13012 to form a soft and compliant surface. Materials for second component 13014 may include silicone, foam, soft thermoplastic elastomers, tacky silicone, fabric or suitable combinations thereof. When patient 13050 wears a patient interface having intermediate structure 13010 with two components 13012,13014 adjusted for the proper macrofit and microfit, superior comfort and sealing are possible.

Customised intermediate structures 13010 may provide optimum sealing around the patient interface, increased comfort for the patient and an even distribution of contact pressure. Additionally, materials may be selected for different portions of the intermediate structure as desired. For example, the nose bridge area may include a softer grade of silicone, foam or thermoplastic elastomer than other areas, which include a single grade of silicone or other harder materials. Patient preferences may also be included in material selection. Thus, materials may be selected for relieving pressure points, providing better sealing and increase comfort and/or stability.

Intermediate structure 13010 may also act as a customised component for securing together the frame and sealing elements. Additional benefits include the ability to provide a method of smoothly transitioning from a custom frame assembly to standard sealing elements and vice versa, enhance aesthetics, and allow the decoupling of components for replacement of at least one component. Predetermined lock/geometry may further be used to prevent accidental coupling of the components to improper components of other devices or competitor products with incompatible functionality.

Figure 13B:
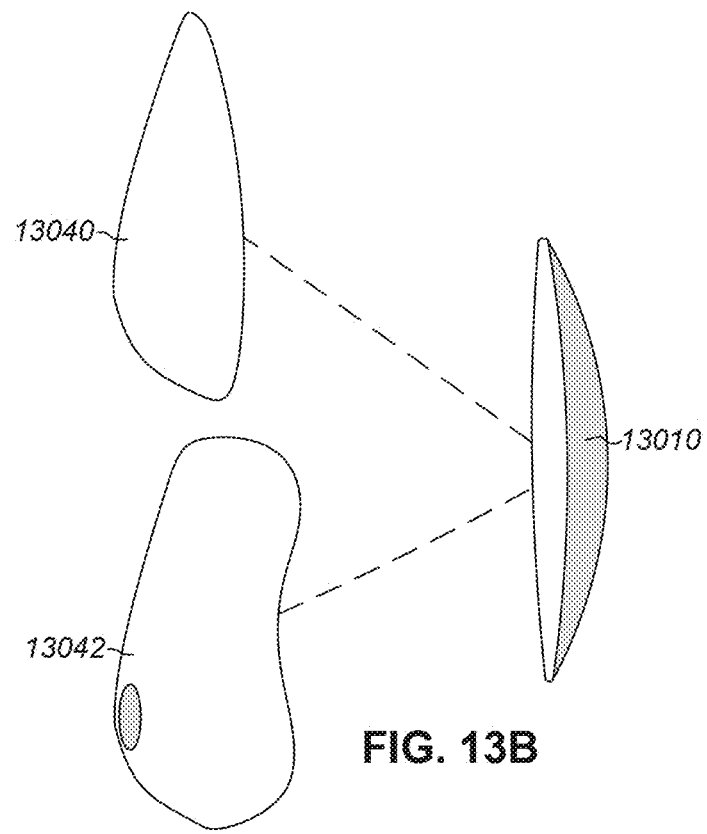

As seen in FIG. 13B, a given intermediate structure 13010 may be coupleable to more than one size and/or shape of frames 13040, 13042. In at least some examples, a single intermediate structure may be coupleable to a line of frames in various sizes, shapes and/or varieties. Thus, intermediate structure 13010 may act as an adapter for customised sealing components. With this ability, patient's may retain a patient interface, while improving sealing and/or comfort accordingly.

2.11.5.3 Sealing Element Customisation

The third component that may be customised is the sealing element 13510, which may provide superior sealing and comfort through customisation. One example of such customisation was briefly discussed with reference to FIG. 11 and the user input. Optimum comfort and seal may be achieved through the selection and placement of suitable materials at predetermined locations. For example, for the nose bridge area, a softer grade of silicone, foam or soft thermoplastic elastomer may be used. The choice of materials may also be based on patient preference and may include silicone cushion, foam, fabric, textiles, tacky silicone, thermoplastic elastomers, gel, polyurethanes, and other suitable polymers, and combinations of any of these materials. With the proper choice of material, relief from pressure points may be realized. Moreover, pressure and shear sensitive areas on the patient's skin (e.g., facial hair, scars, etc.) may also be adequately addressed. In some examples, the proper material may be flexible to help improve the patient interface-to-face interaction on a micro level.

Figure 13C:
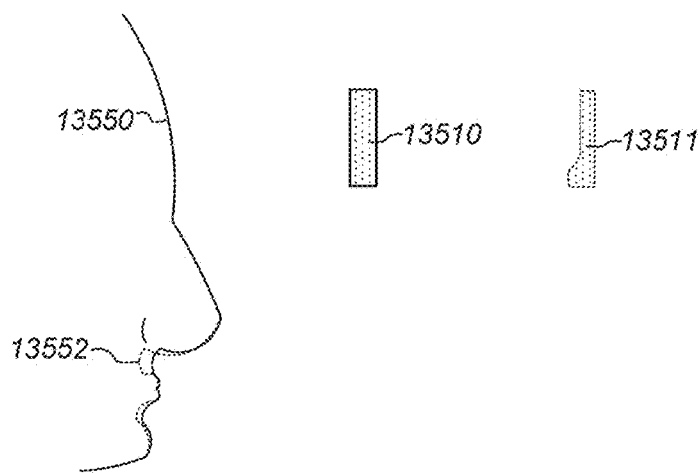

The geometry of a sealing element 13510 may be customised to match the collected patient data for comfort and seal. Such geometric modifications may influence both the macrofit and the microfit of the device. To provide adequate sealing, the three-dimensional geometric and two-dimensional pressure data of a patient's face 13550 may determine the geometric shape of a sealing element 13510 (FIG. 13C). For example, the thickness of the sealing element 13510 may be partially based on the two-dimensional pressure map or the deformed three-dimensional surface data. By analysing both the relaxed surface date (shown, by way of example, in solid lines) and deformed three-dimensional surface data (shown, by way of example, in dashed lines) and the pressure map, an improved sealing element 13510 may be custom-tailored to patient 13550. Thus, sealing element 13510 may be modified to the shape of sealing element 13511 in view of the deformed three-dimensional surface data or the pressure map.

Figure 13D:
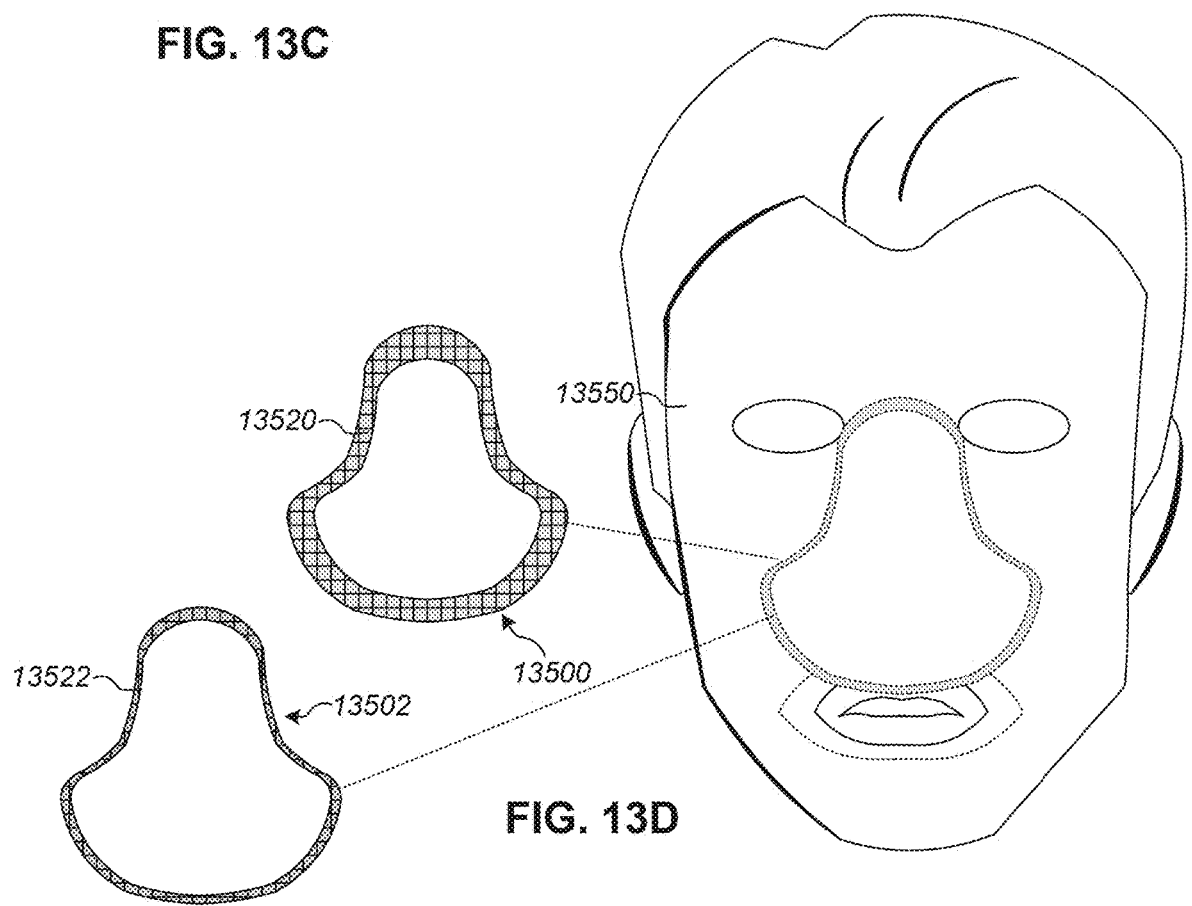

Additionally, the sealing surface area (the total area of patient interface contact on the patient's skin) may be selected from a range of 1 $cm^2$ to 30 $cm^2$ to improve the patient interface seal or distribute the contact pressure for better comfort. FIG. 13D illustrates two possible patient interfaces 13500, 13502 for patient 13550, each having a sealing element 13520, 13522. Sealing element 13520 may provide a sealing area of approximately 15 $cm^2$, while sealing element 13522 may provide a sealing area of approximately 7 $cm^2$. For proper sealing of a patient interface is that there be a continuous line within the region of contact where the sealing force in grams per square centimetre exceeds the air pressure in the patient interface. This condition may be met in many parts of the region of contact but there must be a contiguous line where it is met. By analysing pressure data and both relaxed/deformed states, a proper sealing area may be selected to provide adequate sealing while reducing unnecessary bulk of the patient interface 3000.

The thickness and material of the sealing element 13510 may contribute to patient interface comfort. In some examples, the thickness of the sealing element 13510 may range from 0 mm-50 mm to match a patient's comfort preferences. Thus, the optimal sealing element 13510 would distribute contact pressure effectively, provide optimal sealing based on sealing surface area, improve stability of the patient interface 3000 with regards to differences in facial structure and/or sleeping positions and enhance comfort and sealing based on any of the techniques discussed herein.

2.11.5.3.1 Cushion Fillers

Figure 14A:
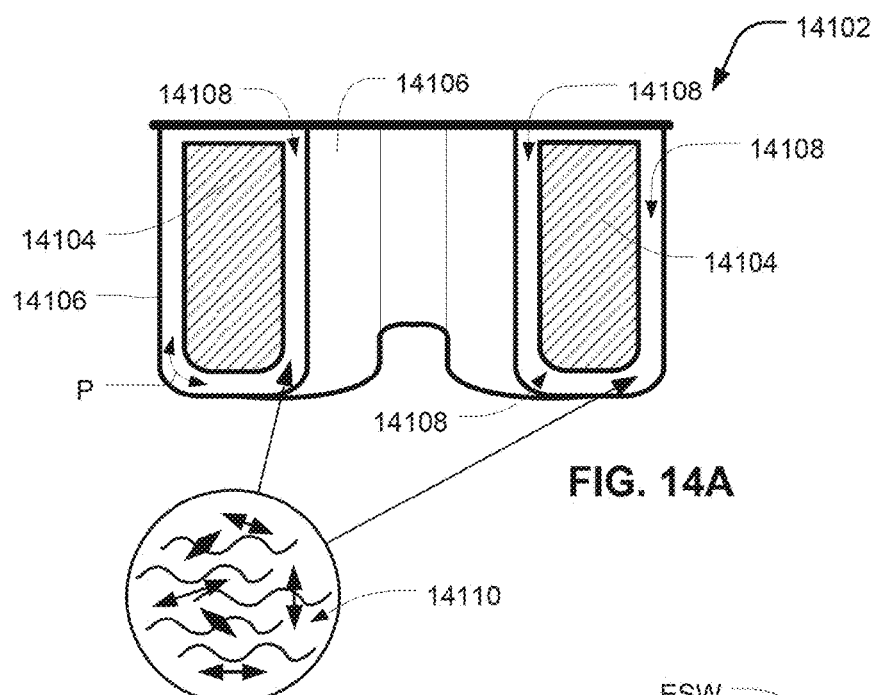
FIG. 14A shows a cross-sectional view of an example of a mask cushion of the present technology taken along line 2-2 of the mask cushion embodiment of FIG. 14B.
Figure 14B:
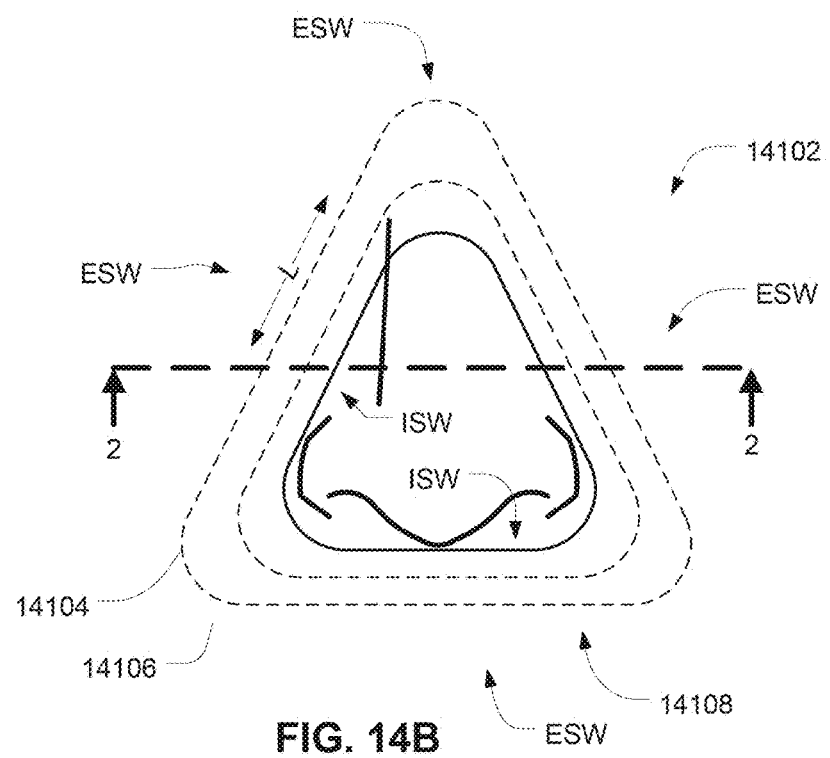
FIG. 14B shows an example embodiment of a mask cushion for a nasal mask.

In embodiments having cushions, the cushions may include fillers to provide a patient mask with a comfortable fit and effective seal for treatment with a respiratory treatment apparatus. In a typical embodiment (e.g. shown in FIGS. 14A-14B), a mask cushion 14102 may employ an inner cushion component 14104. An outer barrier 14106, which may optionally be a membrane, may be applied to the inner cushion to form a chamber 14108 or cell with respect to the inner cushion component 14104. The chamber may optionally be flexible. The outer barrier 14106 and chamber 14108 can serve as a patient contact side of the mask cushion 14102 relative to the inner cushion component. Thus, in some embodiments the inner nature of the cushion component may be more distal with respect to a mask-to-face point-of-contact with the patient when compared with the more proximal outer nature of the barrier or barrier membrane that may be at least in partial contact with a facial feature of a patient. Moreover, the inner cushion component may be wholly or partially encapsulated by the outer barrier. In such a case, the chamber may be a cavity formed by an outer barrier and inner cushion component. Additionally, it will be understood that one or more of the components may be omitted. For example, chamber 14108 and/or outer barrier 14106 may be omitted, resulting in an inner cushion component 14104 that is in direct contact with the skin.

Typically, the inner cushion component may be soft and/or elastic and the outer barrier may be a pliable and/or elastic layer of natural or synthetic material. However, in some embodiments it may be formed at least in part with a rigid or semi-rigid material. Optionally, the inner cushion component may serve as at least a partial filler of the outer barrier.

In some embodiments, each barrier or membrane may be formed from silicone, polyurethane and/or polyethylene. The barrier may even be formed of a viscoelastic material. A pliable and/or elastic nature of either or both of the components and/or membranes of the mask cushion may serve to provide the chamber with a flexible property. In some embodiments, the barrier may be thin, such as on the order of the range of about 0.2 to 5 millimeters. Preferably, the barrier may be about 0.2 to 0.6 millimeters. However, in some embodiments it may even exceed this range and may also be sufficiently pliable to permit sealing with the particular areas or contours of the patient's face to permit a comfortable and effective seal while also maintaining the inner substance of the chamber.

Moreover, the outer barrier can serve to retain a chamber material 14110 within the chamber, such as a gas or liquid, between the inner cushion component and the outer barrier or outer barrier membrane or within an area substantially confined by the barrier. The chamber material may fill or only partially fill the chamber depending on the desired response characteristics of the mask cushion. Preferably, the chamber material may move, flow, permeate within the chamber or otherwise deform in response to applied patient contact pressure on the flexible or elastic components of the cushion such as the outer barrier or outer barrier membrane. For example, an outer layer of liquid may reside and flow within the chamber formed between the outer barrier and the inner cushion component. Thus, in some embodiments, the structure and flexibility provided by the inner cushion component can enable a mask utilizing such a cushion component to conform with a patient's macro facial features (e.g., nose and/or mouth) while the outer layer of the chamber may accommodate for micro facial topography. Similarly, depending on the chosen viscosity or deformability of the chamber material of the chamber, the outer barrier may respond more rapidly than the inner cushion with respect to changes in facial contour resulting from movement during use (e.g., facial expressions) so as to maintain a more effective seal against respiratory treatment leaks.

Figure 14C:
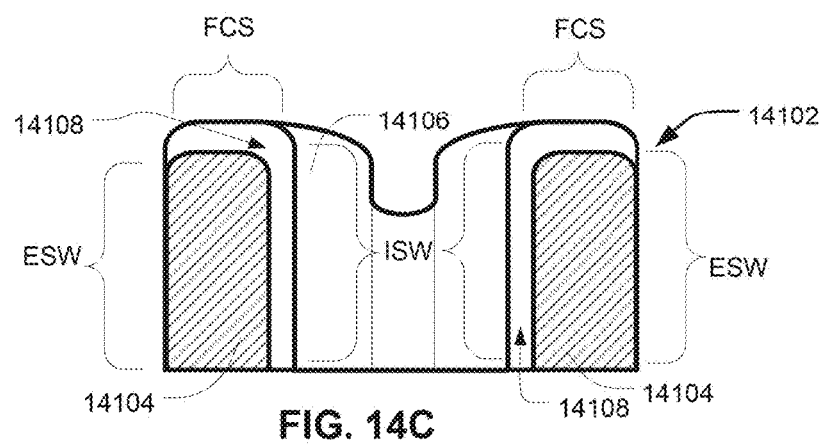
FIGS. 14C-E are cross-sectional views of several embodiments of a removable mask cushion for a frame assembly with a partial chamber.
Figure 14D:
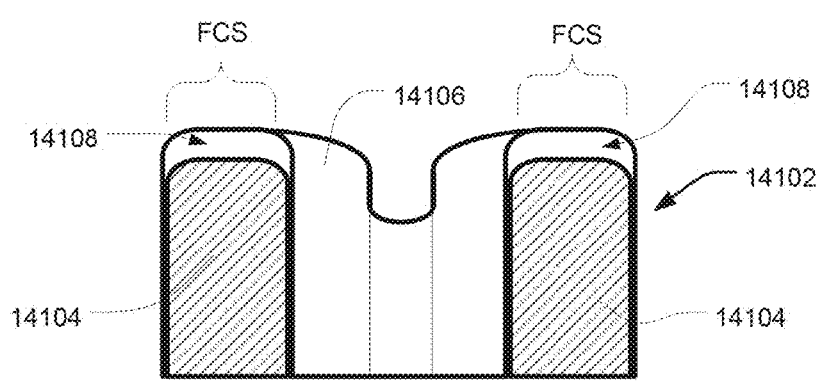

As illustrated in the embodiment of FIGS. 14C and 14D, the outer barrier 14106 may form a chamber that may surround a perimeter of the inner cushion component 14104 (shown as line P) in addition to extending along a length (shown as line L) of the inner cushion component. However, the chamber and inner cushion may be formed in various configurations. The chamber may be formed by one or a plurality of discrete cells that each contain the same chamber material or different chamber materials depending on the desired flexibility to be achieved by the different sections or cells of the chamber. Additional example embodiments showing various chamber configurations are illustrated in the cross-sectional illustrations of FIGS. 14C through 14E.

Figure 14E:
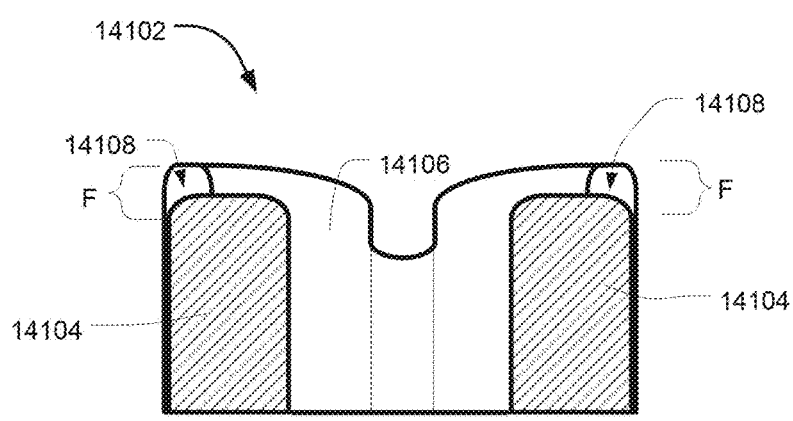

In FIG. 14C, a chamber 14108 extends along a partial perimeter of the inner cushion component 14104. In this example, a chamber 14108 substantially extends along a limit of an Interior Side Wall portion (shown as "ISW" in FIG. 14C and FIG. 14D) of the mask cushion and along a limit of a Face Contact top Side portion (shown as "FCS" in FIG. 14C and FIG. 14D) but not substantially along the Exterior Side Wall portion (shown as "ESW" in FIG. 14C and FIG. 14D). In FIG. 14C, the chamber 14108 extends substantially along a limit of the face contact top side portion of the mask cushion without extending substantially along either of the interior side wall portions or the exterior side wall portions. In the example of FIG. 14E, the chamber is formed along a limit of a portion of the facial-contact top side portion of the mask cushion to form a chamber flap F that may be flexible. Although the flap F portion of FIG. 14E is illustrated extending from the facial-contact top side portion near an exterior side wall portion, an alternative or additional flap portion (not shown) may optionally extend from the facial-contact top side portion near the interior side wall portion. Optionally, although each of these embodiments is generally shown as a substantially continuous enclosed chamber, the interior side wall portion, exterior side wall portion and the facial-contact top side portion in some embodiments may each be formed by a discrete cell of the chamber and may be adjacent to one or more of the other discrete cells of the chamber.

Figure 14F:
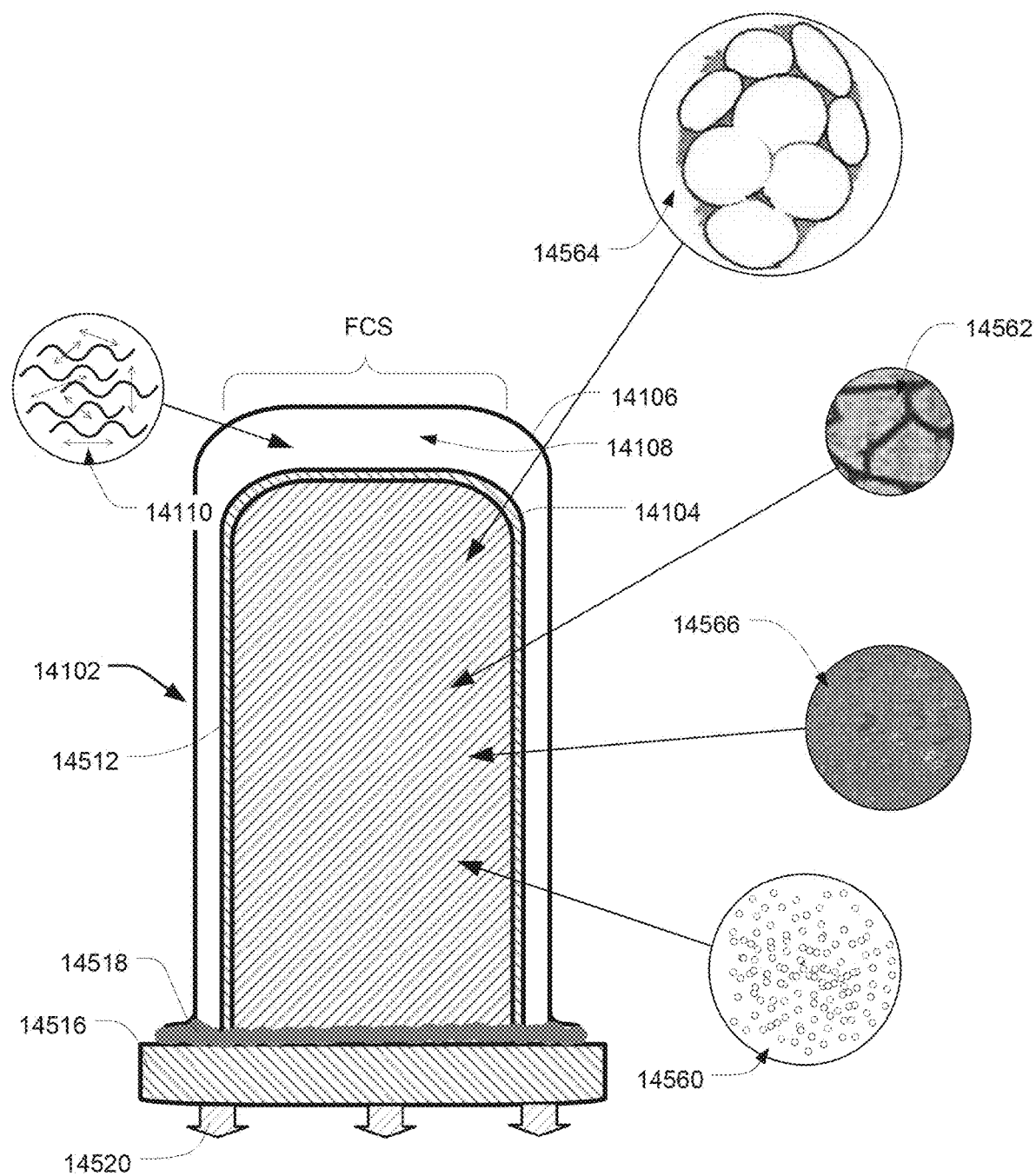
FIG. 14F is a cross-sectional view of a still further embodiment of a portion or part of the mask cushion of the present technology illustrating various filler materials.

Beneficially, the different materials or material properties of the components of the cushion may be combined to yield a synergistic performance when used as a cushion for a respiratory mask. Thus, as illustrated in FIG. 14F, the inner cushion component of any of the embodiments may be a soft springing foam 14560 such as an open cell or closed cell foam. This component may optionally be formed with a polyether, urethane or other elastomer 14562. It may also be formed with a gel 14566 or such a gel with air bubbles, beads, pellets, polyester and/or foam balls 14564 therein. In such a case, the beads, pellets and/or foam balls may be soft and/or flexible. Optionally, such beads, pellets and/or foam balls may be in a liquid or any other of the inner cushion component or chamber materials. The inner cushion component may even be formed with an open cell foam that is saturated or impregnated by a gel. By way of further example, the inner cushion component may be formed with three dimensional spacer fabrics such as in a matrix structure or other three dimensional structure or pattern.

When the chamber material is a flowable substance or other material having a sufficiently low viscosity to promote its movement throughout the chamber, one or more benefits discussed herein may be achieved. For example, the material may be a gas such as air or a liquid such as water, a liquid gel, saline solution or oil. The material may also be sterile. With such a low viscosity, the chamber material 14110 may not only move through the chamber, but it may also optionally flow so as to permeate through or within the material or structure of the inner cushion component. Thus, in some embodiments, the chamber material may saturate the inner cushion component or move through a porous or open structure of the inner cushion component to the extent that the portion of the inner cushion component is encapsulated or retained within the enclosure of the chamber. Such a permeation of the fluid within, for example, a foam inner cushion component can provide an inner cushion with a density greater than without the fluid and it can then provide a different feeling for a patient upon contact or under pressure.

Figure 14G:
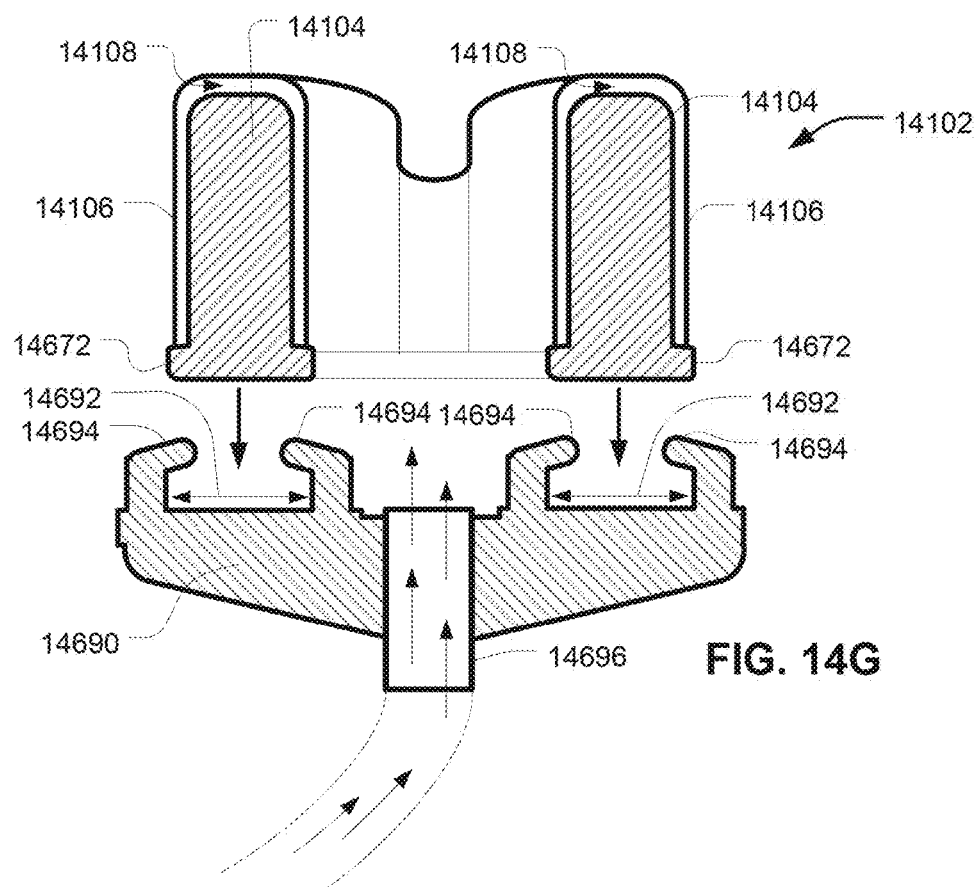
FIGS. 14G-H illustrate another embodiment of a removable mask cushion and an example frame assembly with a channel for retaining the mask cushion.
Figure 14H:
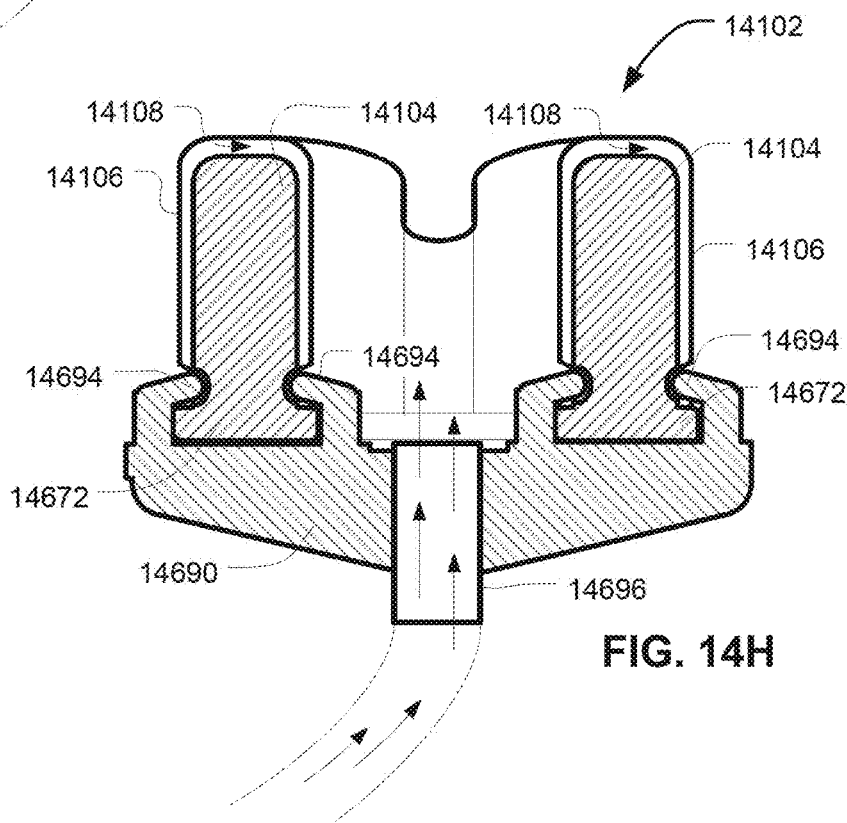
Figure 14I:
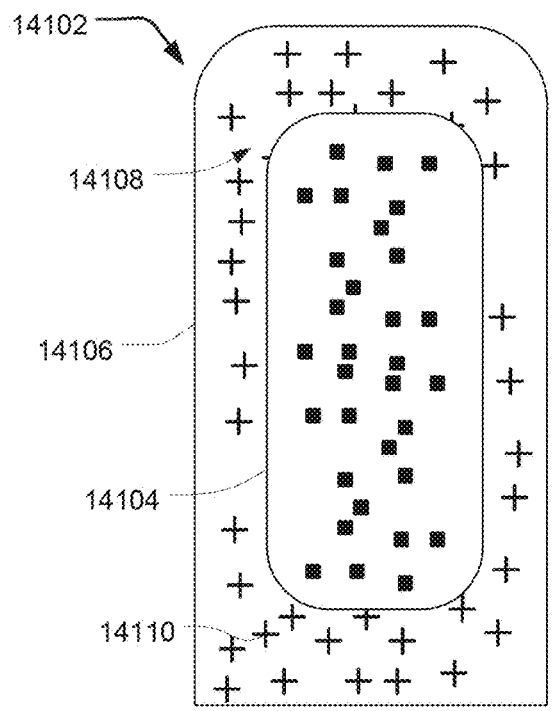
FIGS. 14I-J are illustrations of a cross section of an example mask cushion in a non-compressed state and a compressed state, respectively.
Figure 14J:
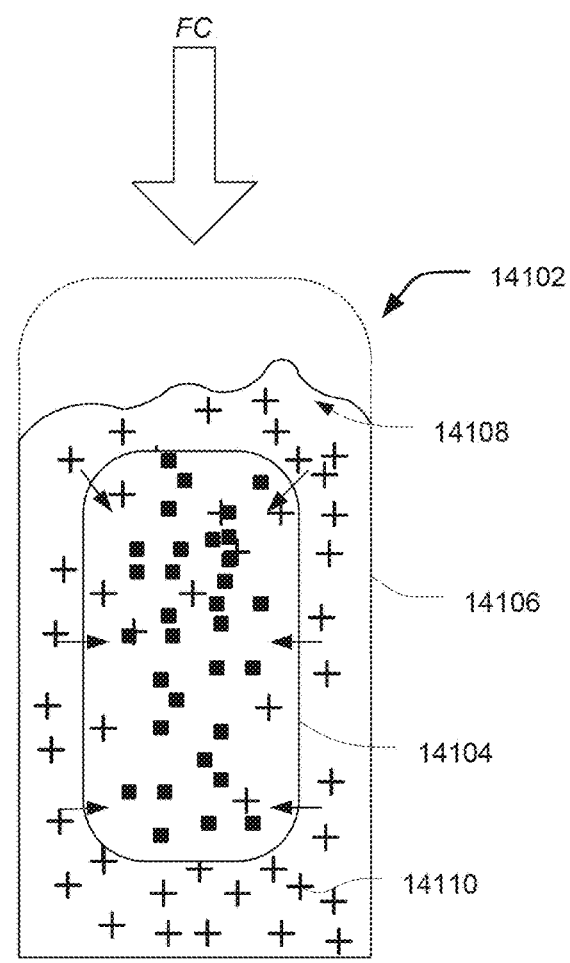

An example of a migration of the chamber material, such as a fluid or gas, between the chamber and the inner cushion component may be considered with reference to FIGS. 14I and 14J. In this example, the mask cushion 14102 has the chamber material 14110, represented by "+" symbols in these figures, within the chamber 14108. When an external force FC, such as a patient contact on the outer barrier 14106 as illustrated in FIG. 14J, is applied, chamber material 14110 may flow (illustrated by the arrows of FIG. 14J which cross the boundary between the inner cushion 14104 and the chamber 14108) as the mask cushion is compressed. Thus, under a load, the outer chamber 10 material may migrate to the inner cushion component, or an aperture thereof, at a rate that is viscoelastic in nature. Releasing the load or force FC may then permit the mask cushion 14102 to return to its non-compressed state illustrated by FIG. 14I. In such a case, the chamber material 14110 may return to the chamber 14108 as the force FC recedes.

However, in some embodiments, such as the cushion illustrated in FIG. 14F, an optional internal barrier membrane 14512 may be included to impede or prevent the chamber material from permeating through or within the material or structure of the inner cushion component. In this way, the internal barrier membrane may internally encapsulate the inner cushion component and prevent material aggregation between the chamber and the inner cushion component. Thus, inner and outer barrier membranes can serve as a dual seal bladder for the chamber material to separate the chamber from the inner cushion component. Thus, for example, gels of different viscosities could be utilized for the inner cushion component and chamber material. For example, a gel with a higher viscosity may be utilized for the material of the inner cushion component (within the inner barrier membrane) and a lower viscosity gel could be utilized for the chamber material in the chamber. Similarly, the flow of a fluid such as water in the chamber can be prevented from combining with, for example, a gel inner cushion component with the inner barrier membrane therebetween. By way of further example, by preventing a permeation of the fluid such as water within, for example, a foam inner cushion component, the inner cushion may be provided with a lighter feel for patient use. Furthermore, by varying the ratio of a quantity of foam for the inner cushion component with a quantity of liquid in the chamber, the hardness or comfort of the mask cushion as perceived by the patient may be adjusted. Similarly, by otherwise varying the degrees of the flexibility or pliability of the inner cushion component with respect to the flexibility or pliability of the chamber and/or outer barrier can provide unique mask performance qualities.

As further illustrated in FIG. 14F, the components of the mask cushion of the present technology may include an integrated or separate mask interconnect component 14516, which may optionally be adhered to another portion of the mask cushion with an adhesive 14518 or other fastening compound or component. The mask interconnect component can serve as an attachment device to combine the cushion with a mask frame for a mask assembly. In this example, the mask interconnect component 14516 includes optional clips 14520 for temporarily affixing the interconnect to the mask frame. The mask interconnect component 14516 can also serve as a cap to assist with retaining the chamber material within the outer barrier membrane. Thus, the interconnect may be adhered with the outer barrier membrane. It may also optionally be adhered to the inner cushion component and inner barrier membrane, if implemented in such an embodiment.

A further implementation of a removable mask cushion 14102 for a mask frame 14690 is illustrated in the embodiment of FIGS. 14G-H. In this version, the flexible nature of the material used for the cap portion 14672 of the inner cushion component 14104, permits the cap portion 14672 of the inner cushion component to serve as an interconnect to a mask frame. In the example, the mask frame includes a channel 14692 sized for fitting with the cap portion. As shown in FIG. 14H, the mask cushion may then be push fit or otherwise inserted into and retained by the channel 14692. The compression fitting formed by ridges 14694 of the channel 14692 and the flexibility of the cap portion 14672, outer barrier membrane and/or inner cushion component create a pressure seal to prevent a treatment gas pressure leak between the mask frame and mask cushion when gas is supplied to the mask via a gas port 14696 of the mask frame.

2.11.5.3.2 Bespoke Gel Cushions

The filler composition, such as for insertion within the chamber previously described, or one or more compartments of a cushion or a bladder of a mask cushion, may itself be selected based on collected patient data to optimise comfort and/or performance. Such compositions may include the use of one or more gels, or other flowable materials. When disposed in a cushion, the different types of gels or materials provide varying structural properties, allowing for customisation for each patient.

Figure 14K:
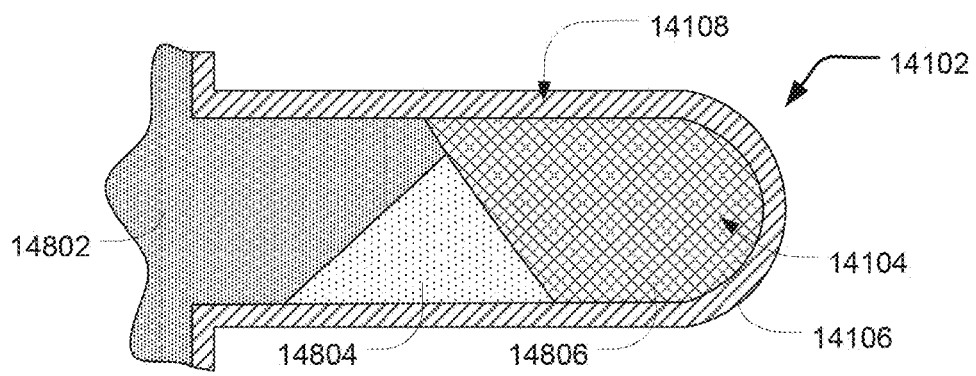
FIGS. 14K-L are cross-sectional views of two cushions having a plurality of materials disposed in an inner cushion components.
Figure 14L:
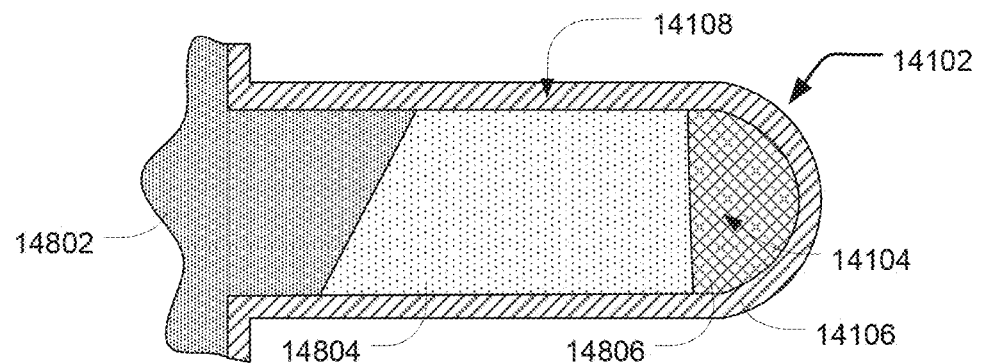

In one example (see FIG. 14K and FIG. 14L), a mask cushion 14102 may employ an inner cushion component 14104 and an outer barrier 14106, applied to the inner cushion to form a chamber 14108 or cell with respect to the inner cushion component 14104. Properties of cushion 14102 may be varied by, for example, customising the amount, shape, alignment and/or other property (e.g., thickness, shape, flexibility, directional flexion) of each material added to each compartment of the inner cushion component 14104 and in its configuration. Thus, in the example shown in FIG. 14K, a first layer 14802, a second layer 14804 and a third layer 18106 are stacked in inner cushion component 14104. As shown, each of the layers includes a different material. Moreover, though three layers of three materials are shown, any number of layers or materials may be used and variations are possible as will be described in greater detail below. In this example, the three layers include three different materials. However, one or more of the layers may include the same material as another layer. It will be understood that in this document, references to different 'materials' are not to be limited to materials of varying chemical composition. For example, references to different materials may include use of one substance (e.g. of a single chemical compound of mixture) in different configurations to achieve varying material properties (e.g. for use in various aforementioned layers). For example, by varying a density of a compressible substance, or by varying a porosity of a foam-like substance, variations in material properties may result, effectively creating different 'materials'.

The materials disposed in layers 14802, 14804, 14806 may be flowable, such silicones or gels of varying properties, such as, for example, gels having varying durometer or porosity. Having materials with varying properties may allow the use of layers of flowable material of varying shapes and thicknesses to be formed in inner cushion component 14104 to achieve the desired properties for the cushion 14102. In some cases, different types of materials may be used in a single cushion (e.g. a cushion may include both a gel and a predetermined grade of silicone). In at least some examples, varying grades of silicone are used for the layers. Moreover, porous foam-like silicone may be used, in which case the porosity/density of the foam may be varied to adjust the resulting mechanical property of the substance in the layer, and as a result, the cushion itself. Additionally, "hollow' layers (e.g., layers of air or other suitable gasses) may be used. Where compressible materials are used, a pressure at which the material is contained (e.g. in the inner cushion component 14104) may be varied to vary the resulting property.

In some cases, foam-like silicone may be produced from a chemical reaction, which may produce gaseous by-products. A manufacturing process for the patient interface (or the inner cushion component 14104) may be configured so that the gaseous by-products may be directed to a predetermined location within the patient interface, or to remain in the chamber wherefrom the gaseous by-product may have originated. At least some of the hollow layers may be configured to receive the gaseous by-products to fill and/or pressurize the hollow layers. Additionally, or alternatively, the gaseous by-products may be utilised to pressurize any chambers containing the foam-like silicone that the gaseous by-products has originated from. In some cases, the patient interface (or the inner cushion component 14104) may be oriented such that a predetermined destination location for the gaseous by-product may be above the source of the gaseous by-product, such that the gaseous-by product may rise to the destination location.

Other suitable materials for placement in the inner cushion component 14104 may be configured to sense and respond to an external variable, such as temperature. For example, the inner cushion component 14104 may comprise a layer configured to change colour according to a temperature (i.e., thermochromic). Such a layer may provide a visual feedback mechanism for a patient (or a clinician) to determine where the inner cushion component 14104 may be in close contact with the face.

Layering of each material may be achieved by sequentially providing the materials and/or varying the quantity of each material which is introduced to form each layer. The shape and structure of each layer may also be varied through the use of different sized compartments in inner cushion component 14104 to inject the material into (see, for example, FIGS. 14A-C), or by varying the orientation of cushion 14102 as the material is injected. Each layer may be visibly differentiated from other layers, e.g. by colouring each layer differently, so that visual confirmation is provided of the layers used to the designer. This may also provide a visual confirmation of customisation of the layers used in the mask to a user, and allow for improved feedback in obtaining data for the next iteration of the mask. For example, a patient may simple say that the "red" component is too rigid, allowing the designer to quickly identify the problem and possible solutions. Additionally, by colouring the materials or layers, aesthetics may be improved or customised as desired by the patient. In some cases, one or more layers may comprise one or more scenting agents, such as according to the patient's preference, for identification of layers. Furthermore, one or more layers may include medications, which may be configured to be released, such as for absorption through the skin or into the air path for inhalation.

Thus, the number of layers and the materials as well as the shapes and the relative positions of the layers chosen may be selected with the patient in mind. Using information from data collection 4300, a first cushion for patient A may be manufactured with material X injected into a first compartment and material Y injected into a second compartment (or as a first layer and a second layer respectively, in one compartment). For a second patient, patient B, data collection may show that material Y is preferably injected into the first compartment and material Z injected into the second compartment (or as a first layer and a second layer respectively, in one compartment).

It will be understood that the layers or compartments need not be of the same size or shape. For example, in the cross-section of cushion 14102 of FIG. 14K, layer 14802 is larger than layer 14804 and substantially similar in size to layer 14806. However, the shapes of the three layers 14802, 14804, 14806 are entirely different. For a different patient, the same cushion 14102 may be selected and the same materials, but the size and shape of the layers may vary as in FIG. 14L. In this example, layer 14806 is the smallest and layer 14804 is the largest. Thus, greater or less rigidity may be achieved in varying locations by changing the size and shape of the layers or compartments.

One or more compartments may be configured to be customisable at an on-going level. For example, one or more compartments may comprise a port through which flowable substances could be introduced or removed. In particular, it may be advantageous to include ports in communication with chambers that are to be placed on a relatively sensitive region of the patient's face (e.g. nasal bone or lip superior). Thus, for example, if a patient finds that the patient interface as purchased in 'standard' configuration is applying too much pressure on the patient's nasal bone, the patient may remove a portion of the flowable material in the appropriate chamber through the port.

Figure 14M:
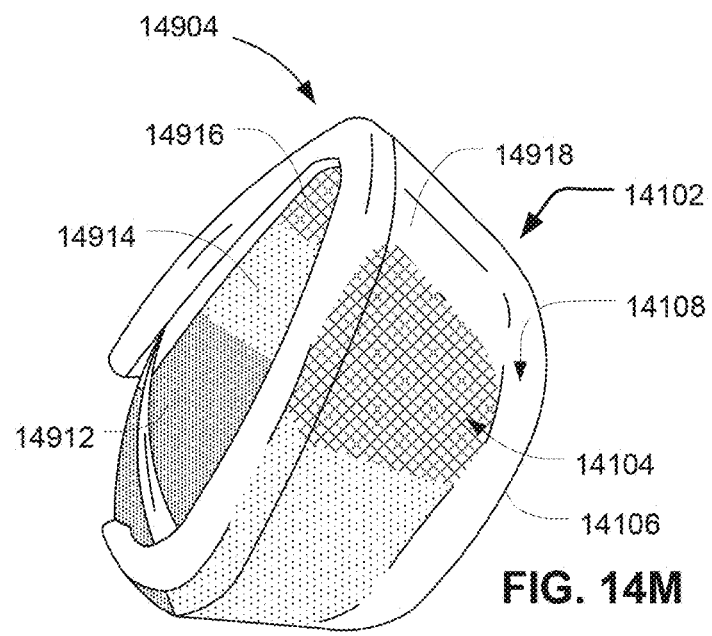
FIGS. 14M-N are examples of a cushion having a plurality of materials arranged in layers in an inner cushion components.
Figure 14N:
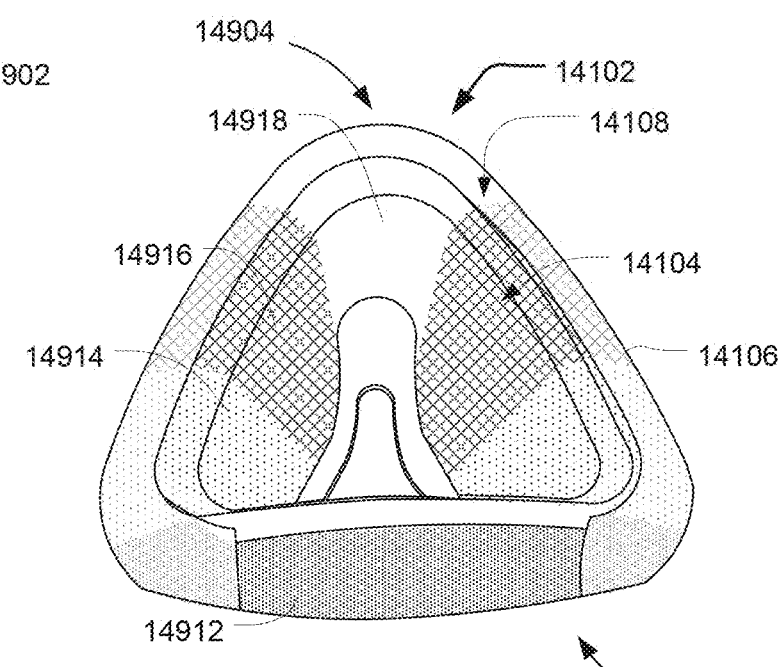

FIGS. 14M and 14N show one example of a layered gel cushion 14102. In this example, layers have been arranged in the vertical direction, so that the properties of the cushion may vary in the vertical direction from the bottom end 14902 (e.g., proximal to a user's mouth) of cushion 14102 to the top end 14904 (e.g., proximal to a bridge of a user's nose) of cushion 14102. Thus, a first layer 14912 formed of, for example, a first gel is used near bottom end 14902, followed by a second layer 14914 of a second gel, a third layer 14916 of a silicone and a fourth "hollow" layer 14918 having air disposed therein.

As briefly discussed, the number of layers used may vary, such that anything from one layer to any number of layers may be used. If a single layer is used, a patient interface may still be customised by varying the type of flowable material which is introduced into the housing for each patient, or the quantity of the flowable material introduced. Relatedly, the stiffness of selected portions of cushion 14102 may also be varied at each point or different areas (e.g. via varying wall thicknesses or wall material properties such as elastic moduli) using this process as the cushion 14102 may be capable of bellowing out as the material is loaded into inner cushion component 14104. Thus, a first quantity of a material may be loaded within cushion 14102 in a first area, while a second quantity of a material (or a second material altogether) may be loaded within cushions 14102 in a second area, to vary an amount of bellowing of the cushion which occurs in the second area in comparison to the bellowing which occurs in the first area. For example, the second area of the cushion may comprise a reduced exterior wall thickness in comparison to the first area, causing the second area to assume a more bellowed shape. This also allows production of customised cushions using standardised tools. Additionally, it will be understood that though cushion 14102 are shown as being symmetric, this need not be the case.

In some cases, an inner cushion component 14104 may be configured so that its rigidity may be varied, such as for customisation. In one form, the inner cushion component 14104 may initially be configured to be relatively flexible, such that the inner cushion component may be placed on the patient to be deformed according to the patient's face, and then 'set' to a higher rigidity. For example, the inner cushion component 14104 may comprise a plurality of chambers not in fluid communication with each other (see FIG. 14P), and configured to be relatively flexible such that it would deform when placed on the patient's face. The plurality of chambers may contain flowable materials which, upon mixture with each other, would increase rigidity. The plurality of chambers may be separated at least partially by one or more frangible seals 14922 configured to be breakable by the patient, for example by flexure of the inner cushion component 14104, and/or by applying a force to a tab 14924 connected to any of the frangible seals 14922. The tab may be in a form of a plate protruding from an exterior surface of the cushion. In one form, the tab may be connected to the inner cushion component 14104 by a perforation, such that it may be removed therefrom. In such an arrangement, the inner cushion component 14104 may be configured that to application of force to remove the tab may also break the frangible seal 14922.

Furthermore, the inner cushion component 14104 may be configured such that the patient would have sufficient time to initiate a reaction to increase rigidity of the inner cushion component 14104, and place the inner cushion component on the face prior to occurrence of permanent setting. In other cases, the inner cushion component 14104 may be configured with a short reaction time to setting, such that the reaction to increase rigidity thereof may be initiated while the inner cushion is placed on the patient's face.

The inner cushion component 14104 may comprise with a re-settable material to allow a plurality of conversions between a set configuration, and a flexible configuration. In one form, the inner cushion component 14104 may comprise a thermoplastic material which, when heated, may be flexible to allow the patient to place it upon their face. Advantageously, use of a re-settable material may allow the patient to re-configure a patient interface according to any changes to a shape of the patient's face, or to allow for any mistakes caused during the setting process (e.g. dropping the inner cushion component 14104, or incorrect placement).

In a yet another example, inner cushion component 14104 may comprise a material that may be 'set' to a higher rigidity in portions. For example, the inner cushion component 14104 may comprise a photopolymer liquid, which may set (i.e., cure) when exposed to ultraviolet light. In this form, the patient may place the inner cushion component 14104 on their face and subject the inner cushion component 14104 to ultraviolet light to cure. Additionally, or alternatively, the patient may only subject portions of the inner cushion component 14104 to ultraviolet light where curing is desired. In some examples, a laser may be used as a source of ultraviolet light in order to accurately and precisely cure the desired regions, while allowing the other regions to remain flowable.

Figure 14O:
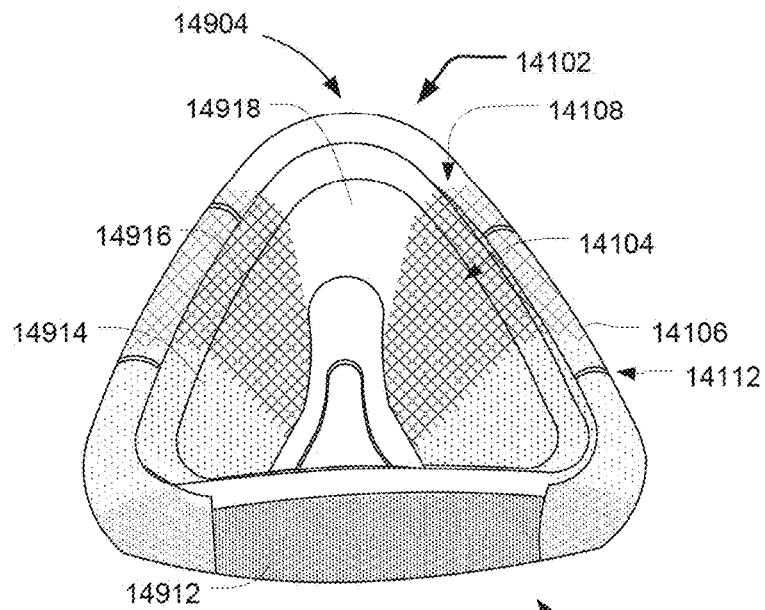
FIG. 14O is an example of a cushion having a plurality of materials arranged in layers in an inner cushion components, and ribs for providing additional rigidity.
Figure 14P:
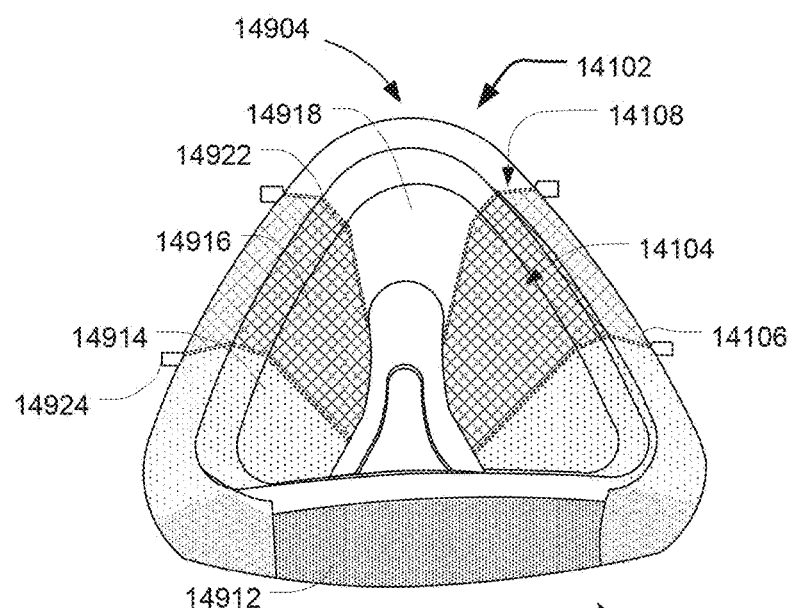
FIG. 14P is an example of a cushion having a plurality of materials arranged in layers in an inner cushion components separated by frangible seals.

In addition to varying the number of layers and the number or quantity of materials used in each layer, cushion 14102 itself may be modified in several ways to improve customisation. For example, cushions 14102 may be formed of multiple standard sizes (e.g., small, medium, large, extra-large) or may include inner cushion components 14104 of differing sizes. Additionally, cushion 14102 may itself be formed of materials or in configurations to vary the stiffness and/or be sizes to accept a certain amount of material within a particular region of inner cushion component 14104. Thus, cushion 14102 may range from being substantially rigid when no material is disposed therein to being a thin membrane, substantially having no structural rigidity in at least some directions, serving instead as a vessel for accepting a material therein, such as a gel, which then provides rigidity. Additional structural elements may also be added to the cushion 14102 to stiffen the structure at predetermined locations. For example, as seen in FIG. 14O, ribs 14112 are added across chamber 14108 to increase stiffness at four locations. Ribs 14112 may be formed of thin bands of wire, or co-molded plastic or polymeric material. It will be understood that the inclusions, location, quantity and/or orientation of ribs 14112 may be varied based on data collection 4300 to stiffen the structure as desired.

Thus, information from data collection 4300 may be used to produce a bespoke cushion. This information may include laser scanning data, passive stereo photogrammetry data, contact collection data, deforming device data, pressure mapping data, as well as any other type of data discussed above including information related to topography, facial structural data (e.g. stiffness in various directions), and/or underlying facial structure (e.g. skin, muscular, and/or bone thickness to predict and/or derive stiffness data).

Such information from data collection 4300 may be used to form a bespoke cushion. In one example, a system may be configured to receive anthropometric data or other information from data collection 4300 and to select an appropriate cushion or cushion component (such as a chamber). The system may then instruct an injector to introduce one or more materials in at least one layer to the chambers of a cushion based on the received anthropometric data.

Feedback from the patient may also be used to improve the fit of cushion 14102. For examples, images of the patient's face may be obtained shortly after use of a cushion 14102. The image may indicate areas where the pressure between the patient interface and the patient may be too high (e.g., by looking for redness that indicates high pressure). The patient may also provide feedback regarding areas where there may be leak (i.e., insufficient contact with the skin). Such feedback may be sent to the manufacturer or designer via the internet or a smart phone application. Using this data, cushion 14102 may be refined to include increased stiffness in leaking regions and/or reduced stiffness where excessive pressure was present between the patient and the patient interface.

2.11.5.4 Volume Scaling

Having considered contact comfort, sealing and stability, attention will now be turned to physical dead space and breathing comfort. Physical dead space and breathing comfort correspond to patient interface volume. Thus, having produced the overall shape of the patient interface and the components, a scaling step may be performed to change the volume of the patient interface in a range from about 1% to about 50%. This scaling may be either upward or downward. That is, in some examples, a preferred volume is first determined and the patient interface shape is either scaled up or down as desired to control the physical dead-space to match the preferred volume. Such scaling may account for comfort and sealing such that significant points are unaltered during the scaling process. For example, the contact area may remain the same while the patient interface is offset outwardly from the patient's nose and/or mouth as desired. It will be appreciated that scaling the patient interface volume may also aid in tuning the vent flow requirements.

2.11.5.5 Headgear and Anchoring Components

In addition to the three elements of the patient interface discussed above, the headgear may also be customised for patients. Proper headgear performance may affect a variety of properties including sealing, comfort and aesthetics and may be realized by modifying the components and locations of the components.

Figure 15A:
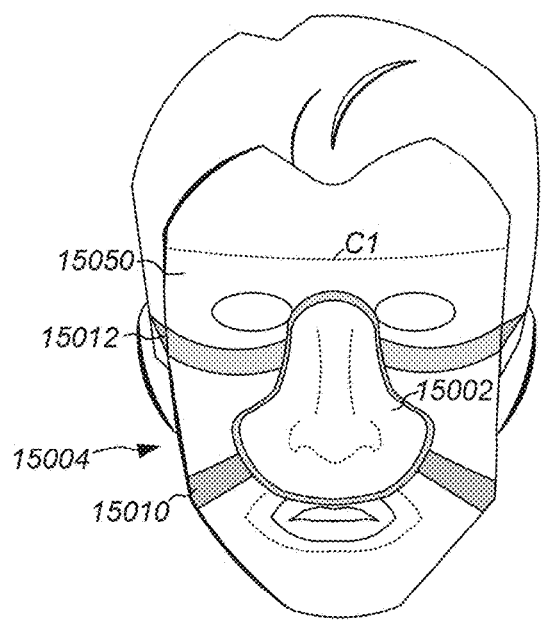
FIGS. 15A-B illustrate one example of headgear associated with a patient's mask.
Figure 15B:
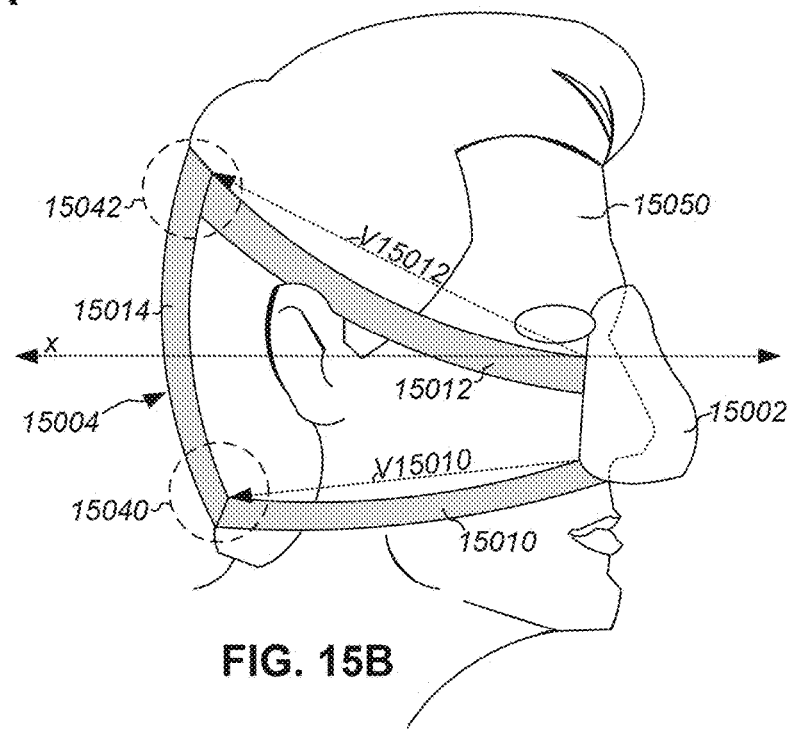

FIGS. 15A-B illustrate one example of the headgear associated with a patient's patient interface. Patient 15050 is wearing a patient interface 15002 secured by headgear 15004. In this example, headgear 15004 includes first straps 15010 and second straps 15012 attached at first ends to patient interface 15002. Second straps 15012 may include rigidizers capable of forming a predetermined shape. First straps 15010 and second straps 15012 extend toward the back of the patient's head (see FIG. 15B) and attach to third strap 1514 at neck attachment 15040 and crown attachment 15042, respectively. As best shown in FIG. 15B, the vectors formed by first straps 15010 and second straps 15012 are labeled V15010 and V15012, respectively.

Headgear 15004 may be modified in several ways. First, strap vectors V15010 and V15012 may be adjusted. By analyzing collected patient data such as the clearance of ears, mouth and eyes, as well as the head shape, neck shape and facial contours, the vectors may be modified. In some examples, depending on the number of attachment points and the clearing of sensitive features on the face (eyes, ears, etc.), vectors V15010 and V15012 may be adjusted from about 0 degrees to about 90 degrees from horizontal plane x.

Second, rigidizers of second straps 15012 may also be modified. In some examples, by knowing the location of the eyes and the cheek contours, straps 15012 may be formed to follow the contours of the patient's face and also clear the patient's eyes reducing irritation and view obstruction from the patient interface.

Third, the lengths of any of straps 15010, 15012, 15014 may be modified in view of the collected head and/or neck shape and/or size. For example, knowing the circumference of the head at different latitudes (for example, C1), the lengths of the straps may be predicted and recommended to patients. In some examples straps 15010, 15012, 15014 may be elastic. In such cases, the length and/or stiffness of the elastic material may be adjusted based on the collected data.

Finally, neck attachment 15040 and crown attachment 15042 may be adjusted in view of collected data on head and/or neck shape and size. In such examples, the geometries of the head and neck shape may dictate the location (latitude) of the neck attachment 15040 and crown attachment 15042. The length of third strap 15014 may also be adjusted based on neck attachment 15040 and crown attachment 15042.

Figure 16A:
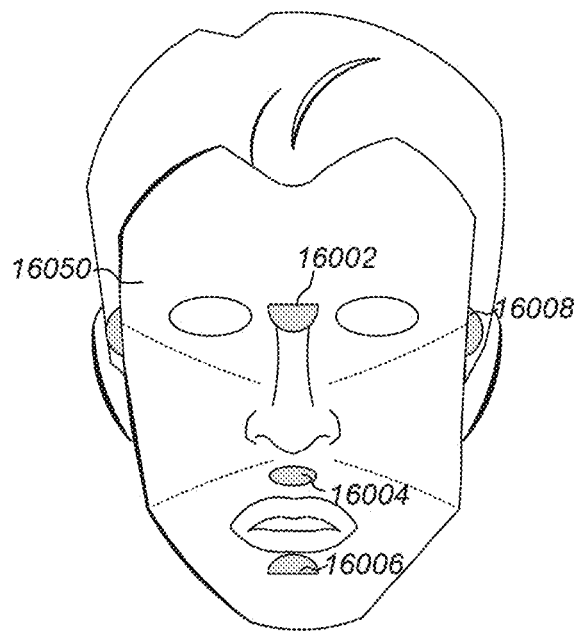
FIG. 16A illustrates examples of anchoring points associated with a patient's mask.

Moreover, to improve stability of the patient interface when worn by a patient, anchoring points may be chosen based on the collected data. Like glasses, where the anchoring points are the nose bridge; the nose bridge, mouth, ears and teeth may act as anchoring points for a respiratory patient interface. Thus, by knowing the location of these features, the patient interface may be designed to perform with greater stability. FIG. 16A illustrates examples of the anchoring points associated with a patient's patient interface. Collected data may be analysed using algorithms to decide the optimal locations of the anchoring points. Certain potential anchor points have been identified in FIG. 16A and include nose bridge anchor point 16002, mouth anchor points 16004, 16006 and ear anchor points 16008. Collecting data and analyzing the locations of the anchor points from the collected data may be used to form patient interfaces and headgears with optimal performance and stability.

Figure 16B:
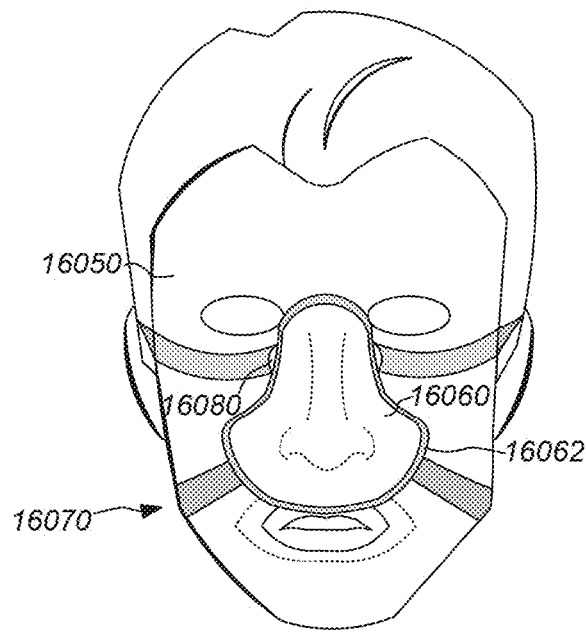
FIG. 16B illustrates examples of motion transfer throughout components of a patient's mask.

Turning now to FIG. 16B, during CPAP therapy the transfer of undesired movement from the positioning and stabilising structure 16070 (e.g. headgear) or from the patient 16050 may be decoupled or separated from patient interface 16060, and specifically from sealing element 16062 via components of the positioning and stabilising structure 16070 or the patient interface itself that prevent this transfer of seal disrupting force. This can be achieved by elastic or compliant joint features 16080 within a connection between the positioning and stabilising structure 16070 and patient interface frame or sealing element 16062. Since the patient interface is customised, sealing element 16062 be can sensitive to small physical disturbances so the positioning and stabilising structure 16070 and also the patient interface and sealing element 16062 can be decoupled from each other to reduce the impact of such disturbances. A customised patient interface enables a less bulky patient interface which may not have sealing element 16062 of a traditional thickness to handle seal disruption forces. A sleek customised patient interface with a thinner sealing element 16062 may obtain stability by maintaining a very reliable static seal through decoupling of the seal disruption forces caused for example by tube torque or patient head movement.

2.11.6 Techniques for Dynamic Stabilisation

In addition to the techniques and examples disclosed above for providing customisation of different portions of a patient interface 16110, techniques for dynamic stabilisation may also be employed. As previously discussed, a patient's facial features and skin are not static elements, but deform and move frequently during therapy. Accordingly, techniques may be directed to stabilising and providing adequate sealing for the patient interface 16110 during movement and/or deformation of the patient's skin and/or facial features. To aid in illustrating these techniques, FIGS. 16C and 16D illustrate certain effects of patient head movement on the patient interface 16110 in different sleeping positions.

Figure 16C:
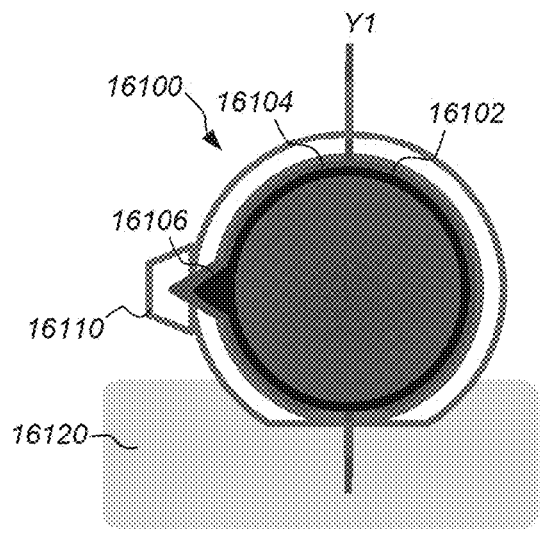
FIGS. 16C-D illustrate the location of a patient interface relative to a patient's head in different sleeping positions.

As shown in FIG. 16C, a schematic representation of the patient's head 16100 is shown lying sideways on a bed pillow 16120. Head 16100 includes skull 16102, skin 16104 and nose 16106, head 16100 further being donned with patient interface 16110. When the patient's head 16100 is resting on its side on bed pillow 16120 as shown in FIG. 16C, skull 16102, skin 16104 and patient interface 16110 are all generally aligned with axis "Y1" and patient interface 16110 aligns with and is cantered about nose 16106 so that there exists adequate sealing between the patient's skin 16104 and patient interface 16110 around the nasal region.

Figure 16D:
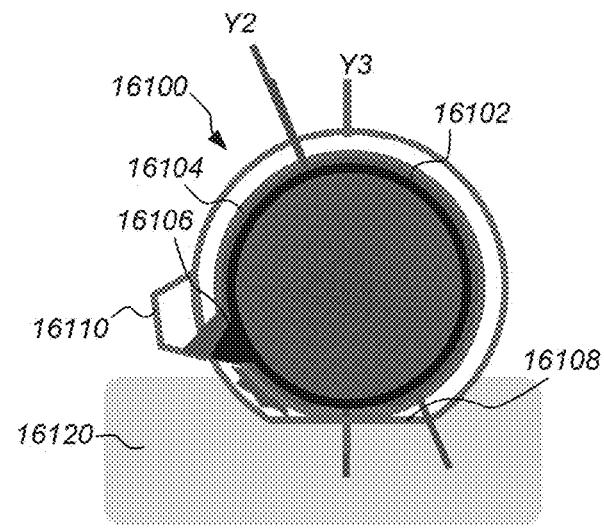

Turning to FIG. 16D, if patient 16100 begins to move his head, difficulties in alignment begin to emerge. Specifically, as seen in FIG. 16D, when skull 16102 is turned toward bed pillow 16120, patient interface 161100 does not move as much as skin 16104 and skull 16102 due to friction between the patient interface's associated headgear 16108 and the pillow. Thus, axis "Y2" generally represents skin alignment and axis "Y3" represents patient interface alignment, Y2 and Y3 being different from one another. In at least some examples, the difference between Y2 and Y3 may be between approximately 1 degree and approximately 60 degrees or in the range of about 10 degrees and about 75 degrees. A patient interface may be configured to compensate for this misalignment.

Figure 16E:
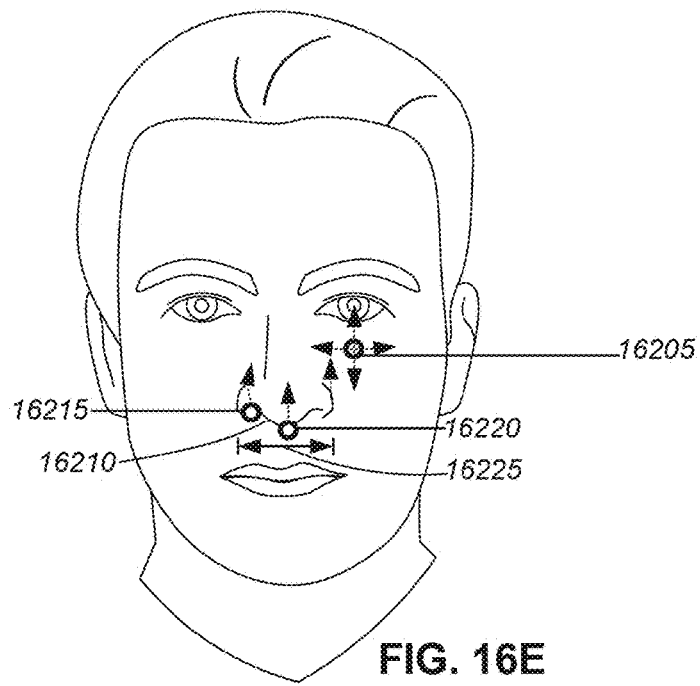
FIGS. 16E and 16F illustrate some possible facial deformations for which a patient interface may compensate.
Figure 16F:
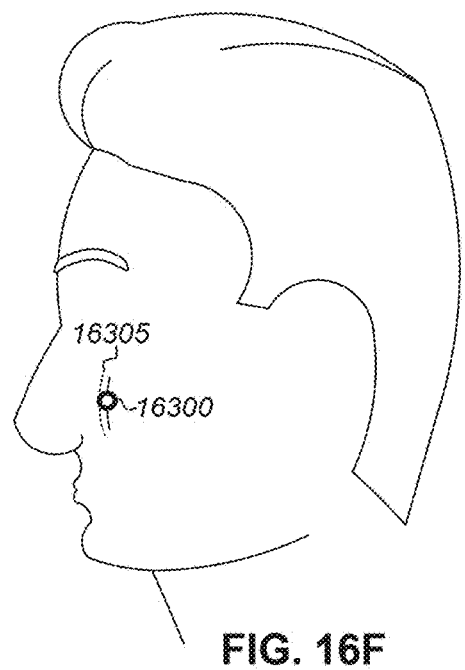

Skin movement and/or deformation may be characterised as sheering and deflection properties in relation to certain facial features. Features of a patient interface may be configured to compensate for such movement and or deformation at certain locations on the skin. For example, the skin sheer may occur at suborbital 16205 (shown in FIG. 16E). A patient interface may be formed to compensate for skin sheer, for example, of between approximately 1 mm and approximately 50 mm, and preferably approximately 40 mm of longitudinal movement (e.g., up and down), and between approximately 1 mm and approximately 50 mm, and preferably approximately 28 mm of lateral movement (e.g., sideways). In other words, movement may occur in any direction within a range of approximately 50 mm.

A patient interface 16110 may also be manufactured that is capable of compensating for up twitch/nose twitch, such as when a patient draws their upper lip upwards. Specifically, a patient interface 16110 may be configured to compensate for variation of the alar angle 16210 during therapy of between approximately 1 degree and 30 degrees, and preferably approximately 27 degrees that may occur when the corners of the nose 16215 moves upwards due to nose twitching and sideways due to side nose twitches. This compensation is used to design and configure the shape and profile of the sealing element 16062 and/or frame 12020. Tolerances for the sealing element 16062 and/or frame 12020 are introduced based on this compensation. For example, if there is less patient movement from their nose twitches, a more precise sealing element 16062 and/or frame 12020 may be provided. On the other hand, if the patient's nose twitches movements are of a greater distance, more tolerance may be provided for the sealing element 16062 and/or frame 12020 to minimise or avoid seal disruption. A patient interface 16110 may additionally or alternatively compensate for an upward movement of the nose corners 16215 and nose middle 16220 which may rise by up to 9 mm and 4 mm, respectively. The patient interface may further compensate for an increase in the width 16225 of the nose by between about 1 mm and about 4 mm. A patient interface may also be configured to accommodate a cheek bulge from a first condition 16300 to a second condition 16305 which may result from all types of nose twitch motion (e.g., sideways and/or up and down), the first condition 16300 and second condition 16305 being spaced by between approximately 1 mm and 10 mm.

Figure 16G:
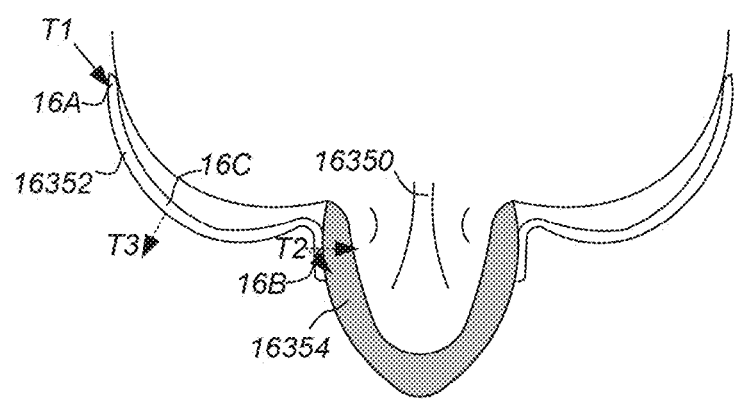
FIG. 16G is an top view illustrating the effects of applying an external force to a positioning and stabilising structure worn by a patient.

FIG. 16G is a top view illustrating the effects of applying a force to headgear 16352, also referred to herein as a positioning and stabilising structure, worn by patient 16350. As shown, a first diagonal force T1 is applied to headgear 16352 at a location 16A near the patient's ear. Force T1 results in a second force T2 at location 16B at the junction between headgear 16352 and frame 16354 as well as a third force T3 at location 16C. In some configurations, a patient interface may be configured to outwardly billow at location 16C to isolate the frame from moving, and decouple the nare frame from movement caused by tube drag, and maintain a seal. In at least some examples, headgear 16352 is configured to compensate for a force of between approximately 1 Newtons and approximately 10 Newtons without diminishing the sealing contact or disrupting the seal with the patient or causing discomfort to the patient that are likely to cause red marks on the patient's face. Several examples are shown below for compensating for such a force, although it will be understood that these are mere exemplary and that other methods and techniques are also possible.

In a second embodiment shown in FIG. 16H, patient interface 16400 includes conduit 16401 connected to sealing element 16402, which in turn is attached to a headgear 16403 having a first portion 16404 and a second portion 16406. As shown, first portion 16404 and second portion 16406 may be formed of different materials. Specifically, first portion 16404 and second portion 16406 may be formed of materials have different material properties. For example, first portion 16404 disposed around the back of the patient's head may be formed of a substantially non-elastic material (e.g., less elastic than second portion 16406), while second portion 16406 disposed over the cheeks and extending to sealing element 16402 may be formed of an elastic material, that is more elastic than the first portion 16404. Alternatively, first portion 16404 may be formed of a sticky or adhering material that does not easily slide on or against the patient's skin while second portion 16406 may be formed of a different material that slides over the skin more easily. First portion 16404 and second portion 16406 may be formed of materials having different coefficients of friction relative to the skin (e.g., first portion 16404 having a higher coefficient of friction than second portion 16406), such that second portion 16406 slides more than first portion 16404 when similar forces are applied to both portions 16404, 16406.

The first portion 16404 may be made from relatively non-stretchable material and the second portion 16406 is made from a stretchable material. A textile cover or wrap may be provided on the second portion 16406. The face contacting surface of the second portion 16406 may be provided with features (e.g. silicone tabs) or made from a material that increases friction to prevent/minimise relative movement between the second portion 16406 and the patient's skin. The outer facing surface of the second portion 16406 may be smooth to prevent translation of forces from patient movement against a bed pillow or bed linen to the patient interface 16400. With patient interface 16400, sealing element is decoupled from most perturbations acting on the headgear as the properties of second portion 16406 allow it to compensate for stretching forces and movement. Moreover, forces at first portion 16404 are not fully transferred to sealing element 16402 via second portion 16406. Thus, the headgear 16403 of patient interface 16400 provides a stable and firm hold on the patient's head, and is easy to don and doff.

In a third embodiment shown in FIG. 16I, patient interface 16410 includes conduit 16411 connected to sealing element 16412, which in turn is attached to a headgear 16413 having a first portion 16414 (e.g., crown strap) and a second portion 16416 (e.g., side straps). The second portion 16416 has an elastic inner layer 16417a that contacts the patient's skin and has more elasticity than the first portion 16414. The first portion 16414 may be relatively inelastic and unable to stretch, for example, made of a neoprene material. As shown, first portion 16414 and second portion 16416 may be formed, second portion 16416 having a double layer configuration of layers 16417a, 16417b. The inner layer 16417a (e.g., patient contacting layer) of the second portion 16406 is a material that is rigid in tension and relatively collapsible in compression, for example, a ribbon. The side strap 16416 is length adjustable via a buckle 16419. Reducing the length of side strap 16416 increases the tension of the elasticity of side strap 16416. At rest under no tension of the side strap 16416, but there is a length mismatch between the elastic inner layer 16417a and outer layer 16417b of the side strap 16416 and the elastic inner layer 16417a is slightly buckled. When tension is applied, for example, by tube torque, the side strap 16416 directly translates the tension to the crown strap 16414. Since the operative portions of the headgear 16413 are relatively inelastic under this condition, there is no stretching of the headgear 16413 which may cause seal disruption. With patient interface 16410, sealing element 16412 is decoupled from almost all but extreme forces acting on the headgear 16413 as the layers of second portion 16416 allow it to compensate for stretching forces and movement. Additionally, the headgear of patient interface 16410 includes first and second portions 16414, 16416 that collapse when compressive forces are applied so that the elastic material maintains tension.

In a fourth embodiment shown in FIG. 16J, patient interface 16420 includes conduit 16421 connected to sealing element 16422, which is turn is attached to a headgear 16423 having a first portion 16424, a second portion 16426 and a wireform 16428 extending through second portion 16426 and coupling first portion 16424 to sealing element 16422. Second portion 16426, which may be in the form of a cheek pillow is configured to traverse along (e.g., slides back and forth) wireform 16428 such as by gliding (e.g., a headgear slide) so that facial friction against second portion 16426 does not translate to movement of sealing element 16422. In one example, the second portion 16426 is slidable between the patient's ear and the patient's upper lip. In other words, the second portion 16426 can slide between the distal ends of the wireform 16428. As shown, wireform 16428 includes an upper wire and a lower wire, although it will be understood that wireform 16428 may include only a single wire or more than two wires or other suitable materials or structures connecting first portion 16424 and sealing element 16422. As shown, first portion 16424 is formed of silicone or Breath-O-Prene and second portion 16426 may be formed from a textile material that may be knitted or woven. With patient interface 16420, sealing element 16422 is firmly held in place with adequate sealing at the patient's nose even in the presence of movement or external forces being applied to second portion 16426. For example, friction between a bed pillow and second portion 16426 may cause movement of the second portion without a comparable force being applied to the sealing element 16422. For example, the maximum amount of force that can be tolerated before the sealing element is disrupted is 10 Newtons. The face contacting surface of the second portion 16246 may be provided with features (e.g. silicone tabs) or made from a material that increases friction to prevent/minimise relative movement between the second portion 16246 and the patient's skin. The outer facing surface of the second portion 16246 may be smooth to prevent translation of forces from patient movement against a bed pillow or bed linen from to the patient interface 16420.

It will be understood that in some examples, combinations of the embodiments described above are possible. For example, a cheek pillow may be combined with other portions having different materials or rigidity to further minimize movement of a patient interface 16400.

2.11.7 Custom Nare Covers

Figure 17A:
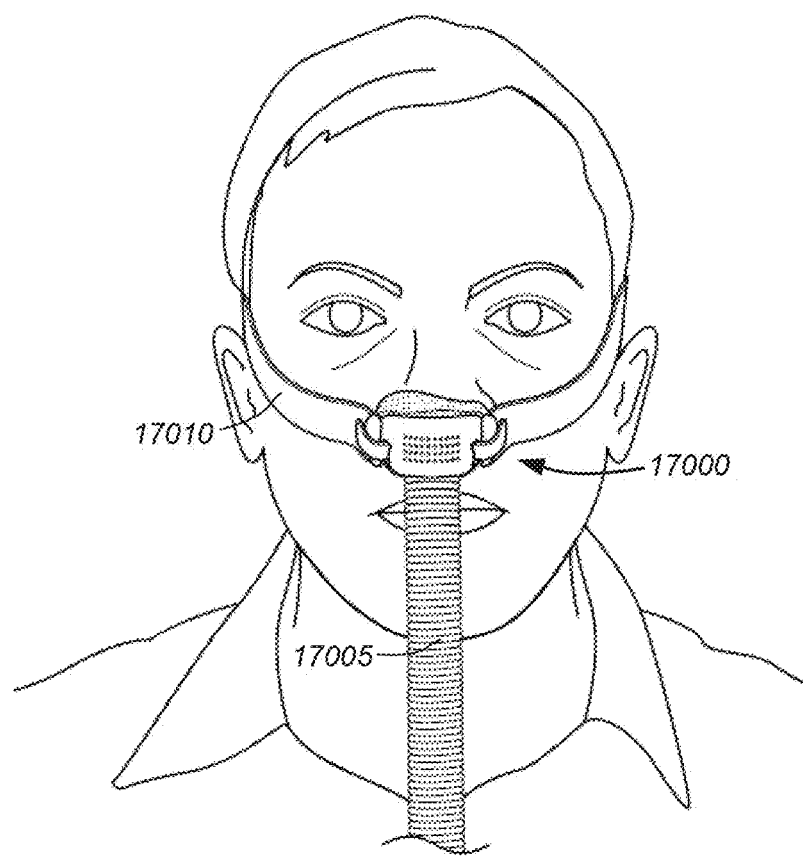
FIG. 17A illustrates one example of a nare cover.

While the preceding embodiments have attempted to provide additional structures for compensating for forces on the headgear, examples are described below that stabilise the patient interface while minimising the size of the patient interface, in one example, particularly the size of the sealing element and surface area of the sealing element in contact with the patient's face. In another example, the thickness of the sealing element and depth of the patient interface are minimised. FIG. 17A illustrates one such example of a patient interface aimed at providing both stability and minimisation. In this example, the patient interface includes a frame assembly in the form of a nare cover 17000 that is attached to an air delivery conduit or tube 17005 and headgear 17010. Details of each of these components will be separately described in more detail with reference to forthcoming figures.

Figure 17B:
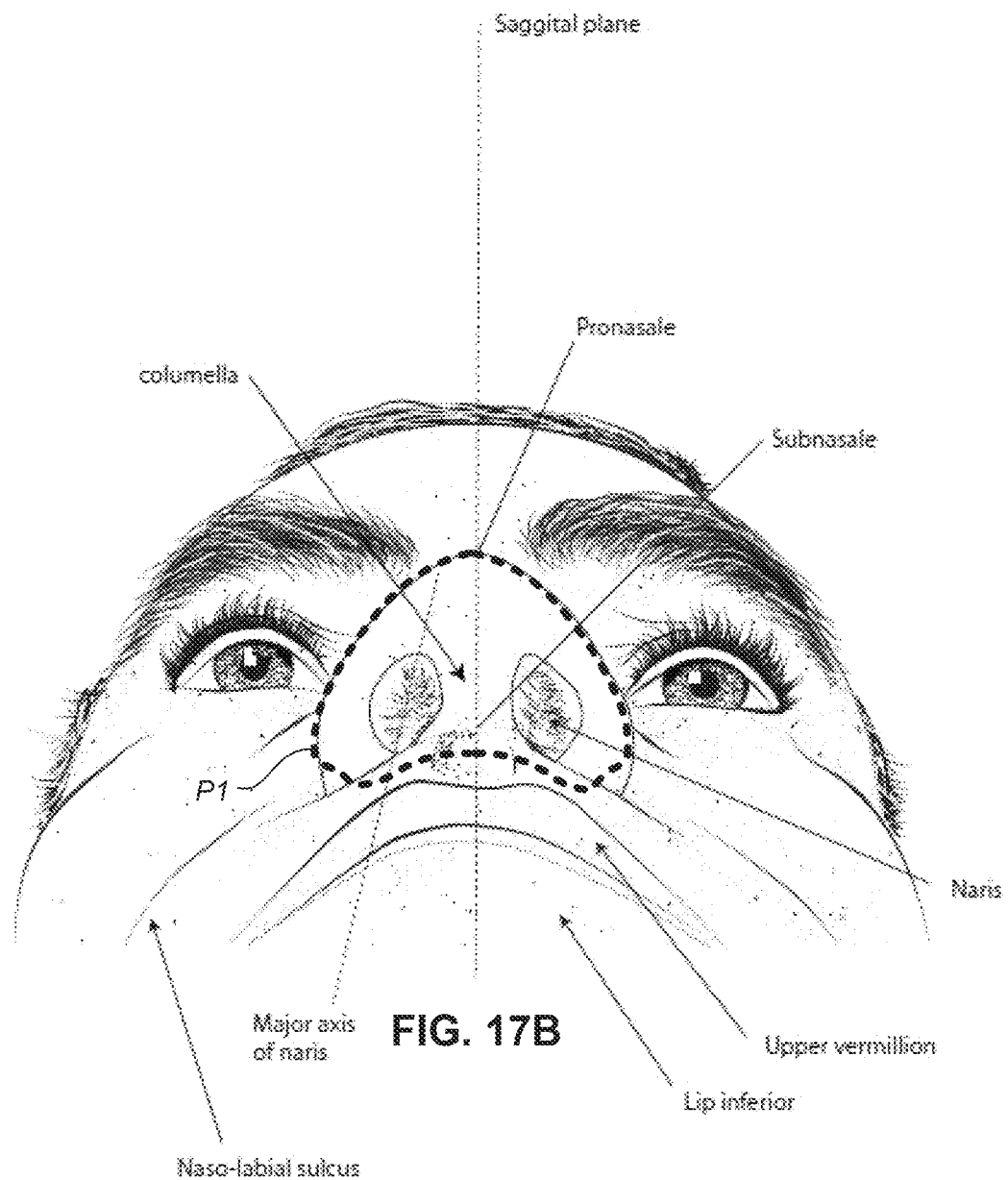
FIG. 17B is an annotated diagram showing the coverage of the nare cover of FIG. 17A.

FIG. 17B is an annotated diagram showing the structure of the bottom of the nose including the position of the nares, subnasale, pronasale, columella, upper vermillion, lip inferior and naso-labial sulcus. A nare cover 17000 may be configured to form a seal around a perimeter indicated by dashed line P1 extending along the pronasale, the outer perimeters of both nares and the subnasale, essentially enclosing or surrounding both nares therein. The perimeter may be minimised by taking care to not encroach on the upper vermillion, the naso-labial sulcus or the lips.

Figure 17C:
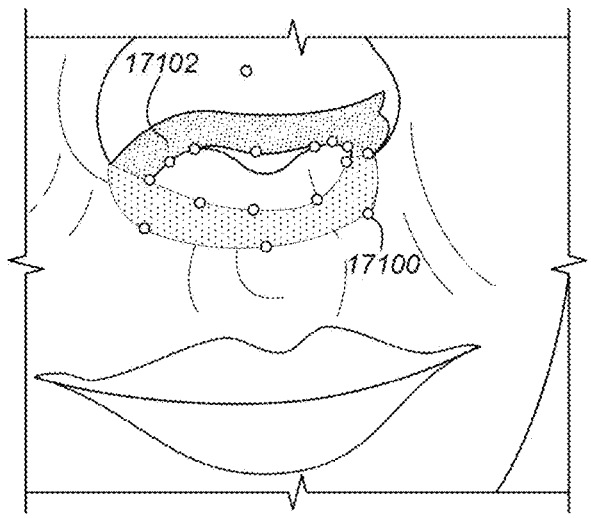
FIGS. 17C-E illustrates image capture and geometric modeling used for forming a custom nare cover.

The size and shape of each component of nare cover 17000 may be customised for each patient to provide proper fitment. By obtaining measurements as described in data collection 4300, a three-dimensional model of the desired nare cover may be computer generated in part, or in its entirety, for each patient. For example, as shown in FIG. 17C, in the image capture step, a plurality of markers 17100 are selected on a patient's nose and patient's upper lip (in this case sixteen points of interest), and a model of a nare cover 17000 is designed based on these markers 17100. In other examples, markers 17100 may be selected at different locations on the patient's face including the eyes, ears, forehead, chin, cheeks, etc. Markers 17100 may be placed at more or less locations, but ideally include placement around the perimeter of each nare, the columella (i.e., the middle segment between the nares), the nostril sill, the corners of the nose, the alarfacial groove, and the under profile of the nose. In at least some examples, the number of points varies based on the requisite resolution (e.g., the distance between adjacent markers). In at least some examples, the resolution around the nose is between about 0.1 mm and about 0.75 mm. The resolution around the nose may also be about 0.5 mm and may be greater than resolution at other areas of the face, which may be only 0.75 mm. The selected markers 17100 may be selected so as to define a plane that is parallel with the nasolabial angle. A contoured surface, shown as shaded surface 17102, may then be defined by markers 17100 that correspond to the surface of the nose around the nares and a portion of the upper lip, the contoured surface having a perimeter that corresponds to perimeter P1 of FIG. 17B.

Figure 17D:
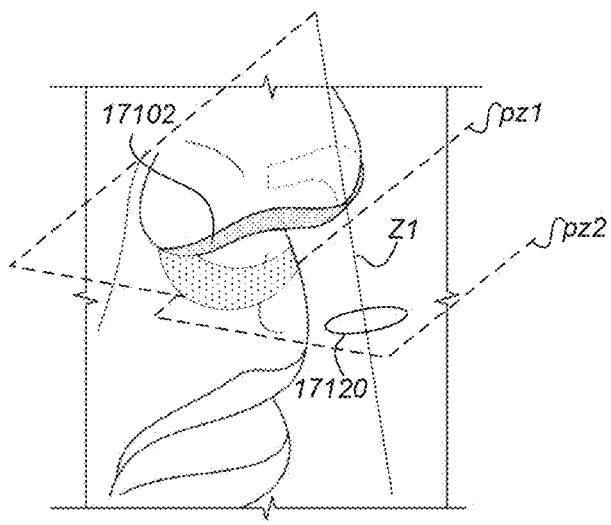

As previously described with reference to FIG. 17A, a delivery conduit 17005 will be connected to the custom nare cover 17000 so that air or other gases can flow therethrough. Movement of delivery conduit 17005 may affect the stability of nare cover 17000. Thus, nare cover 17000 may be configured to receive tube 17005 at a predetermined position, angle and orientation to reduce the effects of hypothetical or expected forces from the tube 17005 onto the nare cover 17000. In one example, during the data collection stage, an elliptical position 17120 may be defined in free space below surface 17102, elliptical position 17120 defining a plane pz2 that is parallel to the plane pz1 of the nasolabial angle (FIG. 17D). To minimize tube torque and the resulting expected forces on a custom nare cover, the angle, position and orientation of a tube may be chosen to reduce the moment arm at the tube-nare cover junction (e.g., a tube connection/connection port of the nare cover 17000) by bringing the junction as close as possible to the patient's face along axis Z1 without making physical contact with the patient's face and allowing a sufficient volume for dead space in the plenum chamber of frame assembly 17200. This minimises seal disruption during therapy caused by tube torque and reduces the bulk of the mask by reducing its depth.

Figure 17E:
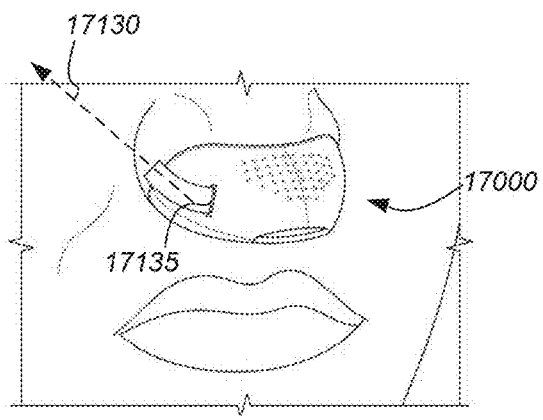
Figure 17F:
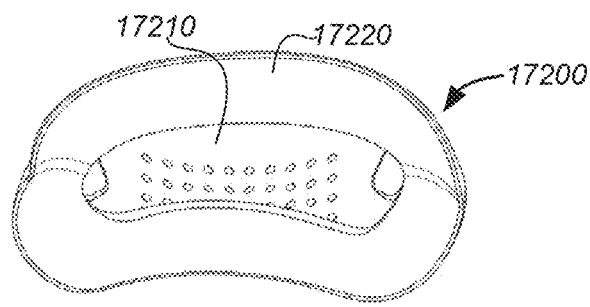
FIGS. 17F, 17G-1, 17H, and 17I illustrate a frame defining a plenum chamber of a nare cover.

In some examples, nare cover 17000 may be attached to the patient via additional headgear 17010 as shown in FIG. 17A. As shown in FIG. 17E, in order to manufacture a nare cover with the proper fitment, headgear vectors 17130 for a rigidizer arm 17250 of a headgear may also be defined. A headgear vector 17130 is an imaginary line that may preferably intersect the mid-point between the patient's eyes and ears and a point on the nare cover 17000. A slot 17135 or recess or socket is then defined in the nare cover 17000. The angle, orientation and location of slots 17135 are discussed in greater detail below. With the image capture and modeling completed, components of nare cover 17000 may be manufactured and assembled. It will be understood that each component may be customised for a specific patient. Customisation may include producing a plurality of fitments (e.g., twenty fitments) for each component, and the patient matched to one of the fitments. Alternatively, customisation may include forming a bespoke component that is individually manufactured for a given patient.

2.11.7.1 Custom Frame Defining a Plenum Chamber

As seen in FIG. 17F-I, the customised nare cover 17000 forms part of the surface of a frame assembly 17200 defining a plenum chamber. Frame 17200 may be formed of a rigid, or semi-flexible material and may define a generally hemispherical or dome-shaped structure. As seen from the inside of the frame 17200 (FIG. 17F), the frame may include an inner wall 17210, and seal receiving surface 17220. Frame 17200 may define a plenum chamber, dead space or cavity between its inner walls 17210 and the patient's skin, while seal receiving surface 17220 may provide an interface for accepting a sealing element as will be described with reference to FIGS. 17K-N.

Figures 1, 17G:
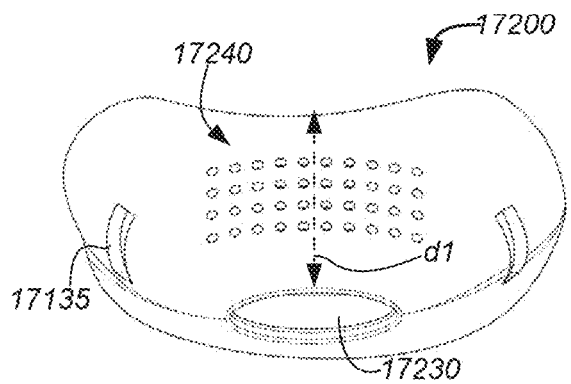
Figures 2, 17G:
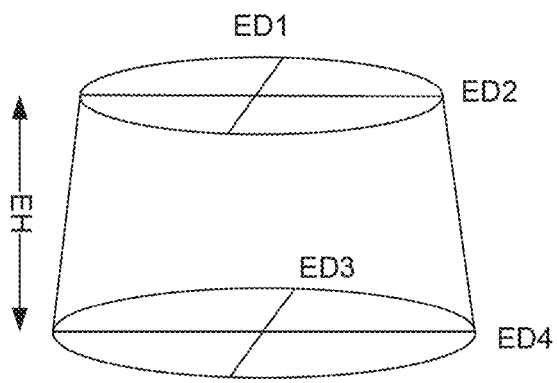
Figure 17H:
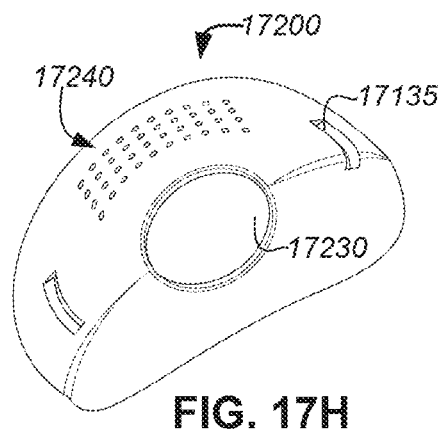
Figure 17I:
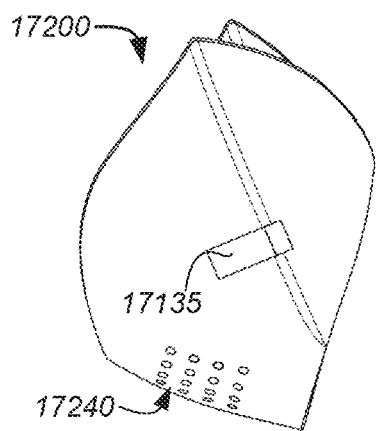

Frame 17200 imparts a 3D shape to the sealing element to form an air-tight housing around both nares and define a small cavity defined by the perimeter of the two nares and a small distance d1 away from the nares (see FIG. 17G-1). Distance d1 is typically less than 30 mm, and ideally as small as possible without making physical contact with the patient's face and allowing a sufficient volume for dead space in frame 17200. In some examples, the dead space or cavity defined as the area enclosed within frame 17200 and the patient's skin is defined by an estimation of the space within a truncated cone (FIG. 17G-2) that approximates a plenum chamber within frame 17200. Thus, the volume within a plenum chamber may be estimated as follow:

$$\text{Volume} = (EH)*\pi/12[(ED1*ED2)+(ED3*ED4)+(ED1*ED2*ED3*ED4)^{1/2}]$$

Where ED1 and ED2 are the estimated diameters of the tube entrance, ED3 and ED4 are approximate diameters of the perimeter of the nose markings, EH is the estimated distance of the tube entrance to the nose. In at least some examples, the size of frame 17200 is a function of the person's nose size, approximately a multiplier between 1 to 2 times of the patient's nose. The height of the truncated cone (i.e. the depth, distance d1, of frame 17200) is controllable and adjustable. In one example, distance d1 is selected to minimise the dead space in the frame 17200 to the lowest distance possible. In another example, the patient's venting preference may be considered, and distance d1 is selected to achieve a user-defined level of breathing comfort and therefore may not be the lowest distance possible.

2.11.7.2 Custom Vent

As previously noted, frame 17200 may include a plurality of slots 17135, in this example two slots, for accepting headgear. Located between slots 17135 is a generally oval or circular aperture 17230 for accepting a delivery conduit (not shown). Frame 17200 may also include vent holes 17240 on its outer surface above aperture 17230. The location of the vent holes 17240 on frame 17200 may be such that they facilitate better carbon dioxide washout, and to improve breathing comfort. For example, vent holes 17240 may be located adjacent the location of the columella only as shown. Although vent holes 17240 are shown on the frame 17200, it will be understood that vent holes may also be located in an elbow located on an elbow disposed between aperture 17230 of the frame 17200 and delivery conduit 17005. The elbow may be a quick release elbow such that the elbow together with the delivery conduit 17005 may be disengaged by the patient from frame 17200.

The number of vent holes 17240 may be selected based on the dead space defined by the plenum chamber (e.g., the volume enclosed within the frame 17200 and the patient's face). The dead space may be calculated and the number of vent holes required to facilitate better carbon dioxide washout, and to improve breathing comfort may be selected. In some examples, a computer algorithm or a look-up table may be used to determine the number of vent holes 17240. The number of vent holes 17240, the location of the vent holes 17240 on a complex surface of the frame 17200, the geometry/profile of the vent holes 17240 and inlet/outlet direction of the vent holes 17240 is selected based on the intended therapy pressure, intended noise level, intended CO2 washout and intended diffusivity. These features of the vent may also be selected based on a function of the volume of the dead space. These features of the vent may also be selected based on a desired humidity level, for example, to prevent rainout. In another example, a baffle or a diffuser may be customised and provided to achieve intended noise level and intended diffusivity. Customisation of the vent 17240 may involve automated computational fluid dynamics (CFD) for each patient and/or comparison with lookup tables based on the volume and geometry of the volume of the dead space when it has been calculated.

FIG. 17J illustrates frame 17200 after coupling delivery conduit 17005 to aperture 17230 and headgear 17010 to slots 17135 via rigidizer arm 17250. In one example, rigidizer arm 17250 may be substantially L-shaped and may include a first end 17252 generally extending in the coronal plane for insertion and coupling to slot 17135 and second end 17254 generally extending in the sagittal plane for coupling to headgear 17010 (e.g., for coupling to any of the straps described above). Rigidizer arm 17250 may be substantially rigid and stiff and may be formed of a metal or other rigid polymer such as polypropylene, Hytrel, etc. Additionally, the L-shape of rigidizer arm 17250 may provide stable fixation and sealing of the frame against the patient's skin, receiving headgear forces, for example force F1, and producing a force F2 on the frame 17200 to push the frame toward the patient's nostrils. Additional customisation of headgear 17010 will be discussed in greater detail below.

2.11.7.3 Custom Sealing Element

In order to provide comfort and superior sealing, a nare cover may include a customised sealing element 17300 coupled to the seal receiving surface 17220 of frame 17200. The sealing element 17300 may be in the form of a cushion that is attachable to the frame 17200, and may have an adhering or tacky member to preserve a seal against the patient's skin during patient movement or in the presence of an external force (e.g., the force of a bed pillow against a portion of the headgear). Such a sealing element 17300 may compensate for the minimisation of the frame 17200 and may provide a patient-friendly solution to movement, resulting in a more comfortable and less bulky patient interface.

Figure 17K:
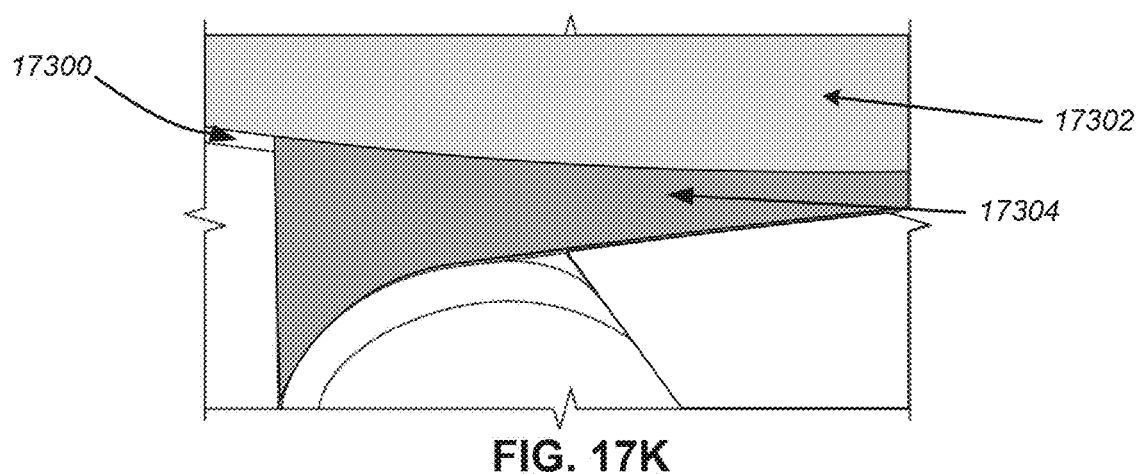
FIG. 17K shows one embodiment of a seal interface including two laminated layers.

Sealing element 17300 may be configured to fasten onto a portion of the patient's nose via an adhesive. As shown in FIG. 17K, sealing element 17300 may be in the form of a cushion comprising multiple layers. The exposed layers may be an adhesive layer. Between the adhesive layers may be a low density (more compliant) foam layer and a high density (less compliant) foam layer. These layers are sandwiched together. The foam layers may together form a thin foam layer 17302. Suitable foams are disclosed in PCT publication no. WO 2014/117227, incorporated herein by reference in its entirety. In use, the low density foam layer is closer to the patient's face than the high density foam layer. The low density foam layer may have a thickness of 4 mm, and the high density foam layer may have a thickness of 3 mm. In other examples, the high density foam layer may be closer to the patient's face in use. In further examples, there may be a single layer of foam with consistent density. One of the adhesive layers is a pressure-sensitive adhesive (PSA) backing 17304 laminated onto or applied to the foam layer 17302. As used herein, the terms sealing element, and cushion may be used interchangeable, although it will be understood that the materials described for the sealing element 17300 are merely exemplary and that other suitable materials may be used. Other suitable adhesives and/or tacky materials may include silicone adhesives, acrylic adhesives and adhesives disclosed in U.S. Pat. No. 8,291, 906 incorporated herein by reference in its entirety. The adhesive may be laminated onto a foam material. A silicone-based adhesive may offer some compliance compared to an acrylic based adhesive. The silicone based adhesive is re-usable and washed to recover adhesion, compared to acrylic based adhesives which are generally used once or twice. In some examples, foam layer 17302 may include sticky foam. Sealing element 17300 may be capable of comfortably sticking to the patient skin on one side, and being coupleable to frame 17200 on a second side. For example, adhesive may be disposed on both the patient-contact side and the non-patient contacting side of sealing element 17300 such that the sealing element keeps the frame 17200 coupled to the patient's skin. Alternatively, sealing element 17300 may be mechanically and releasably engageable to frame 17200 and include only one adhesive side for coupling to the patient's skin. In other examples, the sealing element 17300 may engage with frame 17200 via a hook and loop fastener. In some examples, sealing element 17300 has a perimeter that corresponds to perimeter P1 of FIG. 17B and may be customised to form a desired shape based on data acquired in data collection 4300. The same data collected for forming frame 17200 may also be used to form a sealing element 17300 having superior fit for the patient.

Figure 17L:
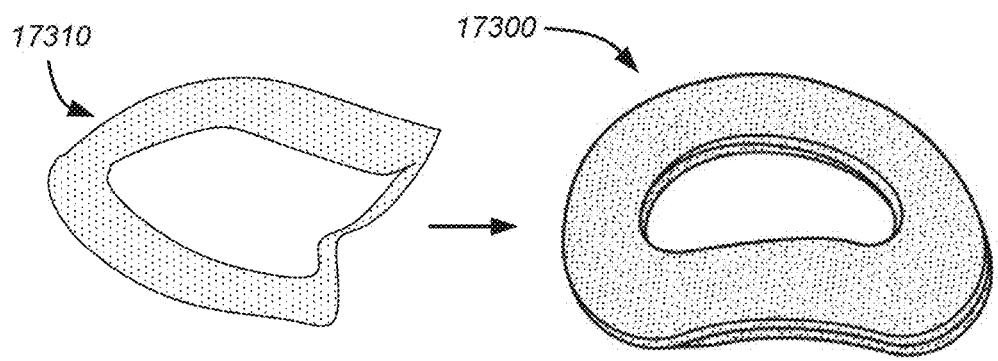
FIGS. 17L-N illustrate the making and use of a seal interface.

During manufacturing, a three-dimensional model 17310 of sealing element 17300 is computer generated for a specific patient may be converted to a two-dimensional flat profile 17300 (FIG. 17L). The three-dimensional model 17310 of the sealing element 17300 is unfolded and flattened by a software program to obtain a two-dimensional flat profile of the sealing element 17300. The sealing element 17300 may be laser cut from a flat sheet, bagged and labeled with a patient's name, thereby creating a custom sealing element 17300 for each patient and a bespoke or custom fit. The conversion of a three-dimensional model 17310 to a two-dimensional flat profile results in quicker manufacturing, optimisation of storage and easier shipment of the sealing element to the patient.

In some examples, sealing elements 17300 of several patients having similar dimensions may be grouped to provide a best fit that more closely fits the patient's anthropometric features compared to conventional mask cushions which generally are only offered in 1 to 3 standard sizes corresponding to the patient's nose width. The grouping may, for example, include twenty sizes of sealing elements 17300 having given lengths, widths, thicknesses and curvatures with a built-in tolerance for each dimension. For each grouping a single flat profile 17310 may be manufactured, the single profile being suitable for several patients of a given group within a given tolerance. For example, the tolerance for a single profile may be +/−2.5 mm for a length dimension and +/−2.5 mm for a width dimension.

Figure 17M:
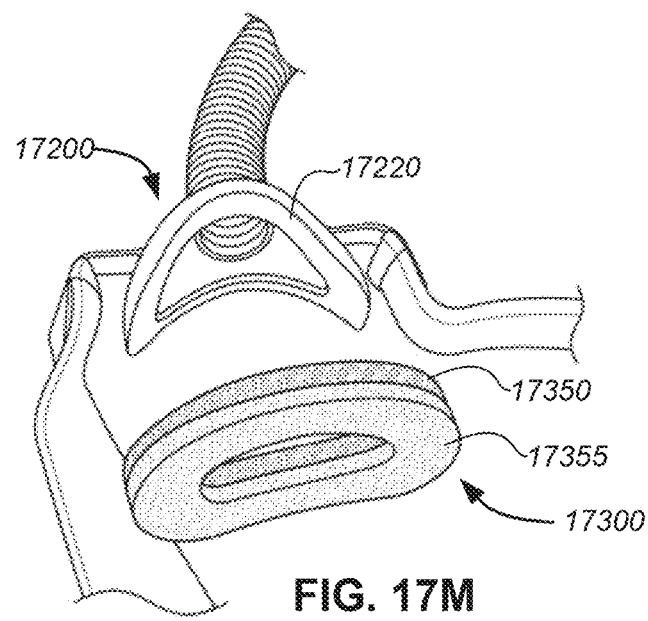
Figure 17N:
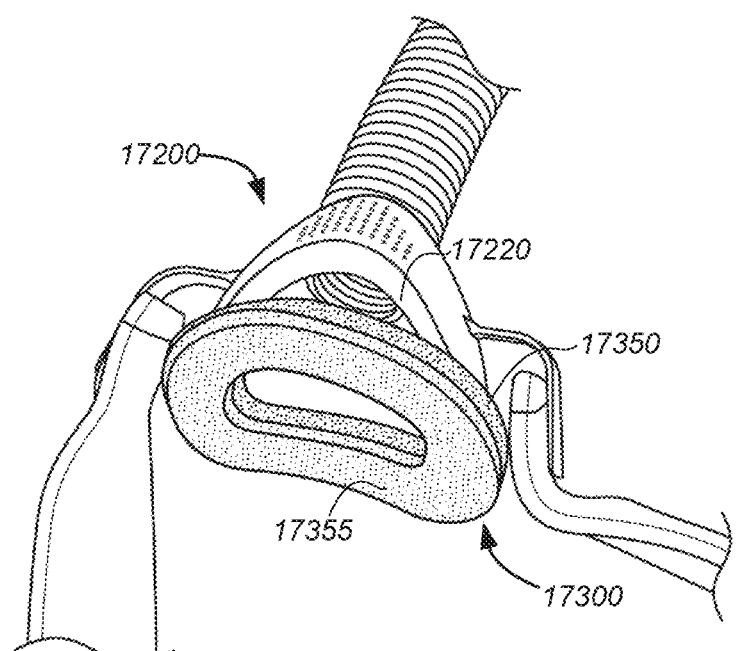

Sealing element 17300 may be coupled to frame 17200 as shown in FIGS. 17M and 17N. Specifically, a first surface 17350 of sealing element 17300 may be adhered or coupled to seal receiving surface 17220 of frame 17200, while a second surface 17355 may adhere or otherwise provide a seal against the patient's skin. Sealing element 17300 may also decoupled from seal receiving surface 17220 as desired. For example, if the adhesive on second surface 17355 of sealing element 17300 begins to wear away, reaches its end of life, or if sealing element 17300 needs to be replaced, it may simply be discarded and another sealing element 17300 may be installed in its place. In at least some examples, sealing element 17300 includes a dual-layered foam construction having an adhesive. The first layer of foam may be disposed on the surface proximal to the frame during use and may be stiffer than the second layer of foam, which is to be disposed proximal to the user's face during use. Such a dual-layer construction may allow for macro and micro adjustments, and ensures a reliable and comfortable seal for the patient. As previously noted, adhesive may be provided on both sides of sealing element 17300. In some examples, the adhesive on the first layer of foam (e.g., the layer adjacent the frame 17200) has more adhesive strength than the adhesive on the second layer of foam (e.g., the layer adjacent the patient's skin). Such a configuration may allow the patient to adjust the position of the frame 17200 without the sealing element 17300 becoming detached from frame 17200. It will be understood that the use of adhesive is merely optional and that other methods of coupling the sealing element 17300 to frame 17200 are contemplated such as mechanical engagement or magnetic engagement.

2.11.7.4 Custom Headgear

The headgear 17010 of the patient interface may also be customised. Using the measurement of the patient's head circumference, the length, elasticity and thickness of headgear straps can be adjusted for a specific patient to provide a secure, stable and comfortable patient interface that is not too tight or too loose and requires little or no manual adjustment by the patient. Additionally, the texture or surface finishing of headgear straps such as smoothness or roughness may be selected specific for a patient, for example, if they have facial hair or head hair. The profile, shape, arc length and flexibility of the rigidizer arm 17250 may be selected specific for a patient. For example, a patient may have a wide face or a narrow face, and the rigidizer arm 17250 is customised to exert minimal clamping pressure against the patient's face and closely follow the contours of the patient's face, and also direct the headgear straps to pass optimally between the patient's eyes and ears.

In some examples, optimisation of the length, elasticity and thickness of headgear straps allows tightening or loosening the headgear strap (e.g., if length adjustable) or via elasticity if it is an elastic headgear, to control the headgear tension force in the Frankfort horizontal plane for retaining the mask firmly against the patient's face. The headgear tension force may customised depending on the patient's comfort level and while ensuring that a minimum amount of headgear tension required to maintain a seal. Some patient's may prefer a higher headgear tension force than is necessary to maintain a seal because the feeling of tightness of the headgear is reassuring and provides greater confidence for these types of patients.

Additionally, the angle, position and orientation of slots 17135, which accept a corresponding tab or protrusion of rigidizer arm 17250 of the headgear may be selected to create a custom headgear fit and custom headgear vector for each patient. As previously noted with reference to FIG. 17E, changing the angle, position and orientation of slot 17135 changes the headgear vectors 17130 for a rigidizer arm 17250 of a headgear and allows for the customisation of the headgear for superior fit. In some examples, the rigidizer arm 17250 is customised to lie beneath every patient's cheek bone and optimally pass between the patient's eyes and ears. Thus, by knowing the patient's anthropometric features from the data collection 4300 step, the angle of the headgear vector may be tuned to achieve better performance. The angle of the headgear vector may be determined relative to the Frankfort horizontal. An optimal angle for the headgear vector may improve comfort and stability of the patient interface because the angle for the headgear vector causes the sealing surface/sealing perimeter of the sealing element 17300 to provide even pressure on against the patient's face (e.g. patient's nose and patient's upper lip). Without such optimisation of the headgear vector, tightening headgear straps may result in mask ride up and therefore a less than optimum seal as the force to effect the seal by the seal element 17300 is not evenly distributed.

In another example, an optimal angle for the headgear vector may include a bias to preload (typically a slightly higher angle), to take into account tube torque in a downwardly direction. In other words, if the tube 17005 is pulled downward by a certain amount of force, the preloading of the angle for the headgear vector is able to accommodate this certain amount of force before mask stability is influenced.

2.11.7.5 Assembled Nare Cover

Figure 17O:
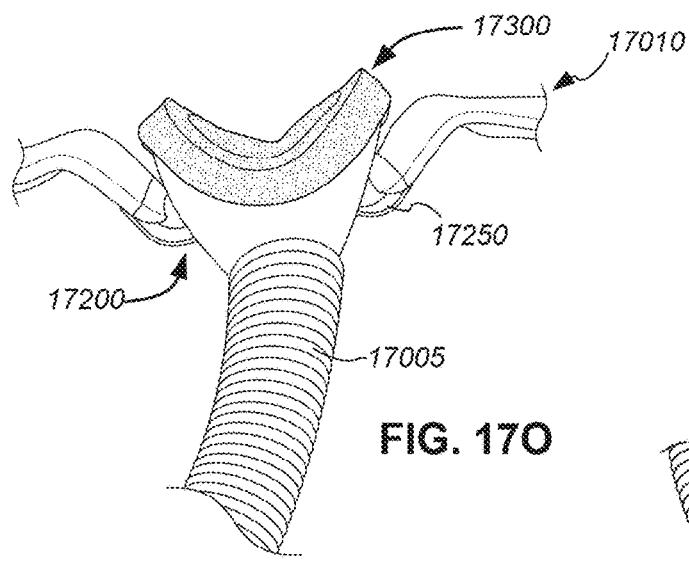
FIGS. 17O-Q illustrates a nare cover.
Figure 17P:
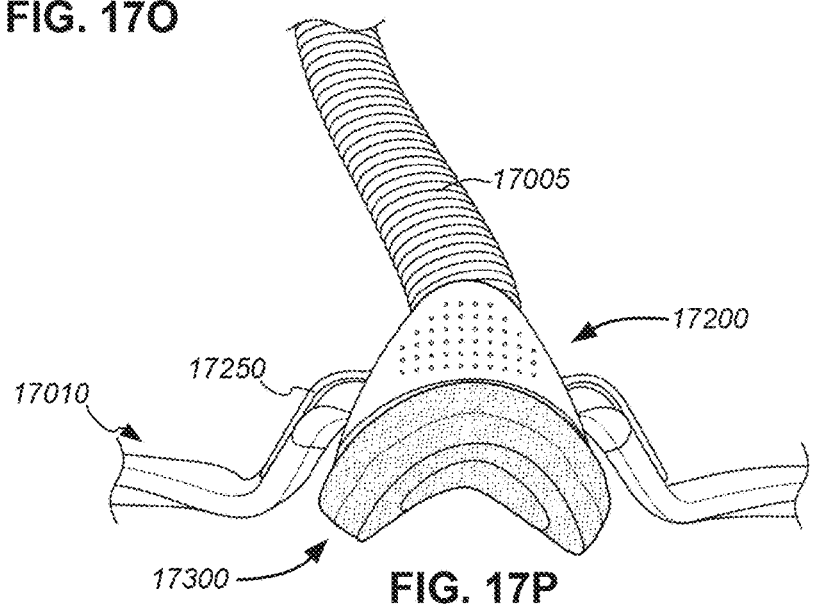
Figure 17Q:
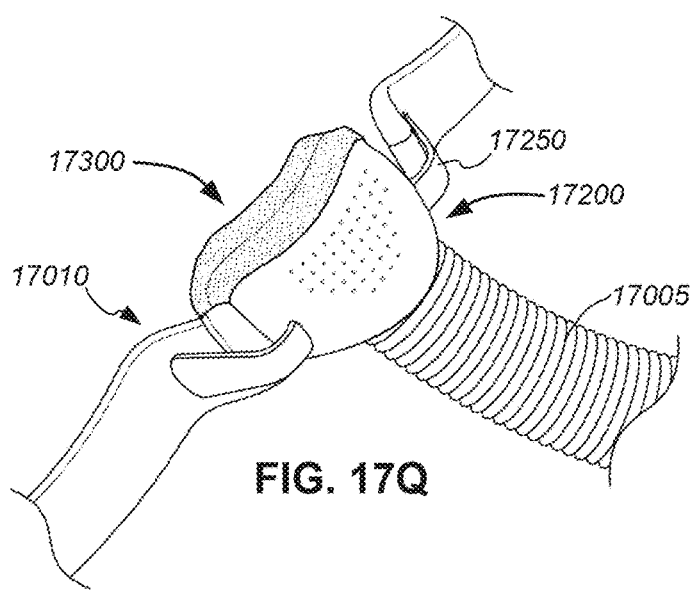
Figure 17R:
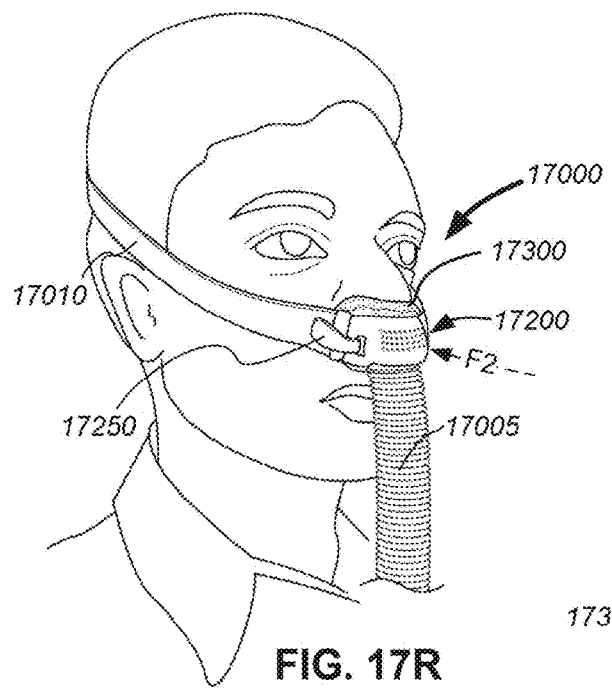
FIGS. 17R-T illustrates the use of a nare cover.
Figure 17S:
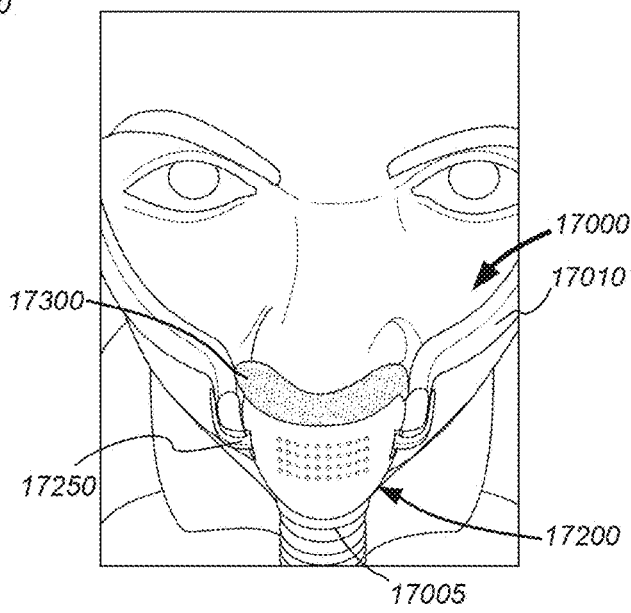
Figure 17T:
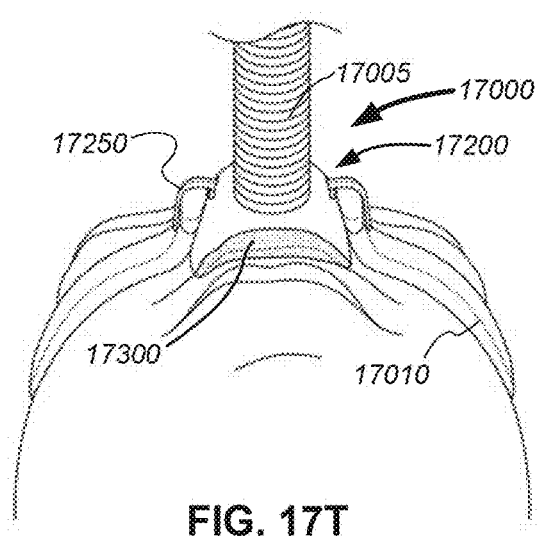

A fully assembled nare cover 17000 including frame 17200, rigidizer arm 17250, sealing element 17300, headgear 17010 and delivery conduit 17005 is shown by itself in FIGS. 17O-Q, and as donned in FIGS. 17R-T. The patient may couple sealing element 17300 to frame 17200 and don the customised nare cover 17000 using headgear 17010. As previously discussed, rigidizer arms 17250 serve as a transition from frame 17200 to headgear 17010 and redirect forces from the headgear so that frame 17200 and sealing element 17300 are pushed towards the patient's face, resulting in a desirable seal of sealing element 17300 with the patient's face. By using data acquired during data collection 4300, the angle, location and orientation of slots 17135 may be carefully selected to ensure that the rigidizer arms 17250 to be received pass between the mid-point between the patient's eyes and ear, or other desirable angles/positions/orientations to provide an optimal, stable and comfortable seal for the small nare cover assembly.

Thus, the result of having such a nare cover is a customised mask, which is as small as possible while being stable. Specifically, the combination of superior contact of sealing element 17300 to the patient's face, the sealing element 17300 interface with frame 17200 and the use of L-shaped rigidizer arms 17250, as well as the customisation from data collection results in a small mask that is stable despite tube drag, and body movements that occur under therapy. It will be understood that customisation has been discussed herein with reference to frame 17200, vent holes 17240, sealing element 17300 and headgear 17010. In some examples, a fully assembled custom nare cover 17000 includes one or more customised elements. Additionally, customised and standard components may be combined in various combinations to reduce cost (e.g., a bespoke frame 17200 and a standard-sized sealing element 17300), and also to offer various choices for the patient.

2.11.8 Complete Patient Interface Design Package 4550

With the patient interface and/or the headgear customised, completed patient interface design package 4550 is the group of files which includes files for each of the individually designed patient interface components, ready for the manufacturing. Completed patient interface design package 4550 may include data or information relating to any of the following: the list of components in the patient interface system (e.g., frame, intermediate structure, sealing element, headgear and/or any additional accessories such as elbows, tubes, headgear clips and such), CAD or data file for each component, the manufacturing technique for each component, the material(s) required for each component and designer and/or user comments. The patient's CAD file and/or photos (if any) may be retained to support the selection of visually aesthetic features to stylise the patient interface according to the patient's preference and taste.

2.11.9 Manufacturing 4600

Completed patient interface design package 4550 may be sent to manufacturing 4600. There are many different manufacturing techniques available for fabricating any of the components discussed above. Additionally, it will be understood that a combination of the techniques discussed herein may be used to form different components of a respiratory patient interface.

Figure 18A:
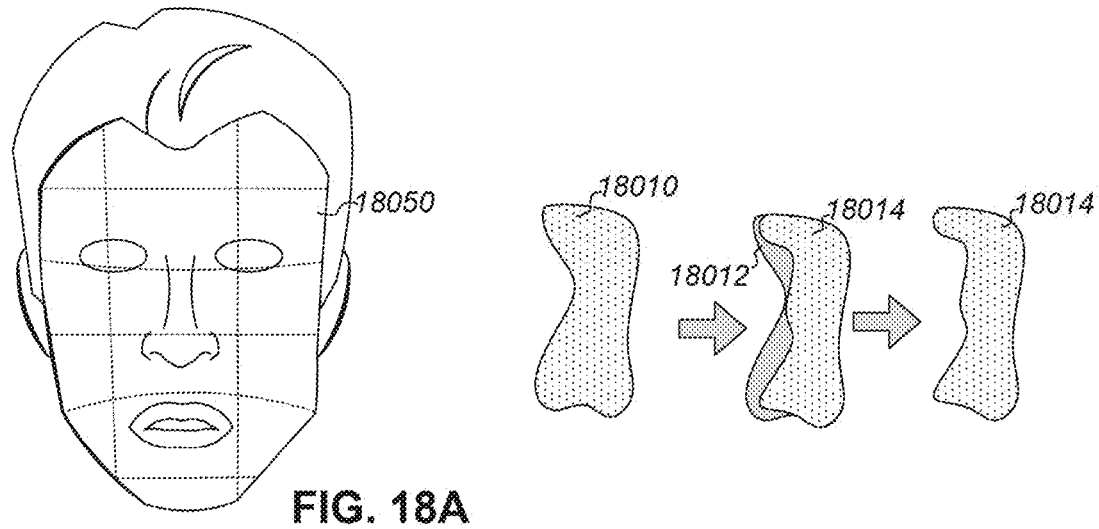
FIGS. 18A-B illustrate examples of the manufacturing process of different components of a patient's mask.
Figure 18B:
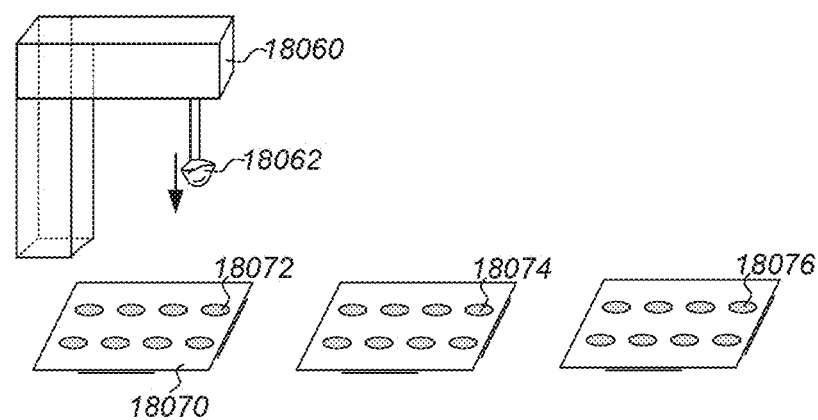

The first group of techniques may be referred to as subtractive techniques. In subtractive techniques, data may be collected and analysed from patient skin 18050 and a completed patient interface design package sent for manufacturing (FIG. 18A). A large blank component 18010 may be modified to remove extra material 18012 such that the remaining portion 18014 forms the required custom component. In some examples, large blank component 18010 is large enough to encompass most possible variations for custom component 18014. Several exemplary methods under the subtractive techniques including machining using a CNC machine to form the component out of a large block or generic patient interface-shaped material. In some examples, a material such as silicone or thermoplastic elastomer may be frozen into a rigid structure prior to machining. A laser etching machine may also be used to remove material from a larger block of material to create the component. This may be used to form rigid components or cut thin materials (foams, fabrics, silicone sheets, etc.). Abrasive chemicals may also be used to remove materials to create different finishes on the components. Some examples include the use of acetone on plastics. Cutting tools, such cutting tool 18060 shown in FIG. 18B, may also be used to stamp out components 18072, 18074, 18076 from sheets of material 18070. Thus gel components 18072, silicone components 1804, and foam components 18076 may all be formed by changing the type of sheet. This technique may be used, for example, to create headgear and sealing elements. Moreover, cutting tool 18060 may have curved cutting edges 18062 to form three-dimensional shapes.

A second group of techniques may be referred to as additive techniques. These may include SLS/SLA/FDM Printing, which involves printing the plastic or silicone components directly, thereby reducing waste material from subtractive manufacturing. Components may be printed using a high quality 3D printers. Silicone components may also be fabricated via additive manufacturing through using a fast curing silicone grades. Silicone and elastomer printing machines may also be used. When available, patients may also be able to print their own patient interfaces at home or at a local three-dimensional printer outlet. This method is efficient and sustainable as there is almost no waste or scraps leftover from blanks. Textile spraying is also possible, which involves spray a first material onto a second material. For example, a flocking material (felt, silk, textile blend etc.) may be sprayed onto the intermediate component effectively creating a sealing element. In some examples, the material may be sprayed through a multi axis CNC nozzle, mixed with glue/binding agent. Thus, varying numbers of layers may be applied to all or parts of the sealing surface, forming a customised sealing element.

Additionally, different manufacturing techniques may be used for components of a mask assembly. For example, when forming a custom nare cover, a frame and a sealing element may be formed of the same or different techniques. Additionally, multiple techniques may be used to shape one component of a custom nare cover.

The frame 17200 may, for example, be formed by machining different-sized molded blanks. In at least some examples, a plurality of different-sized blanks are molded to cover a broad spectrum of sizes. After data acquisition, the blank closest to the intended mask design may be selected and the blank may be machined from the blank. Alternatively, a number of different sized frames may be formed using size probabilities to mold a given volume of each size, and the frame of the closest size may be chosen for a patient.

Non-traditional machining techniques may also be applied to molded or cut blanks to form the frame and/or the sealing element. These techniques may include electrical discharge machining, chemical etching, water jet cutting and/or laser cutting. In electrical discharge machining, complex geometries of a component such as a frame or a sealing element may be processed with a high degree of resolution. By using electrical discharge machining, a clean surface finish may be formed in delicate elements as no direct contact is made with the working piece. In some examples, electrical discharge machining may be used to create vent holes or rigidizer receiving slots in a frame. Chemical etching may also be used to subtractively remove material and create a customised geometry with high resolution in a frame and/or a sealing element. In some examples, chemical etching is desired when manufacturing fragile elements of the frame and/or sealing element as there is no need for high heat which may damage a heat affected zone of a component. Water jet cutting may also be used to shape a frame and/or a sealing element through a simple process with no heat affected zones to create intricate geometries with high resolution. Laser cutting may also be used to create precise edges and cuts through a variety of materials that may be suitable for a frame and/or a sealing element.

Additionally, the sealing element may be milled with a high speed abrasive cutting tool to shape the sealing element into the desired shape. In at least some examples, the sealing element is frozen prior to the milling process. Later, the sealing element is thawed or heated to room temperature, if necessary. It will be understood that multiple techniques may be used in series or sequentially.

2.11.10 Tooling

Figure 18C:
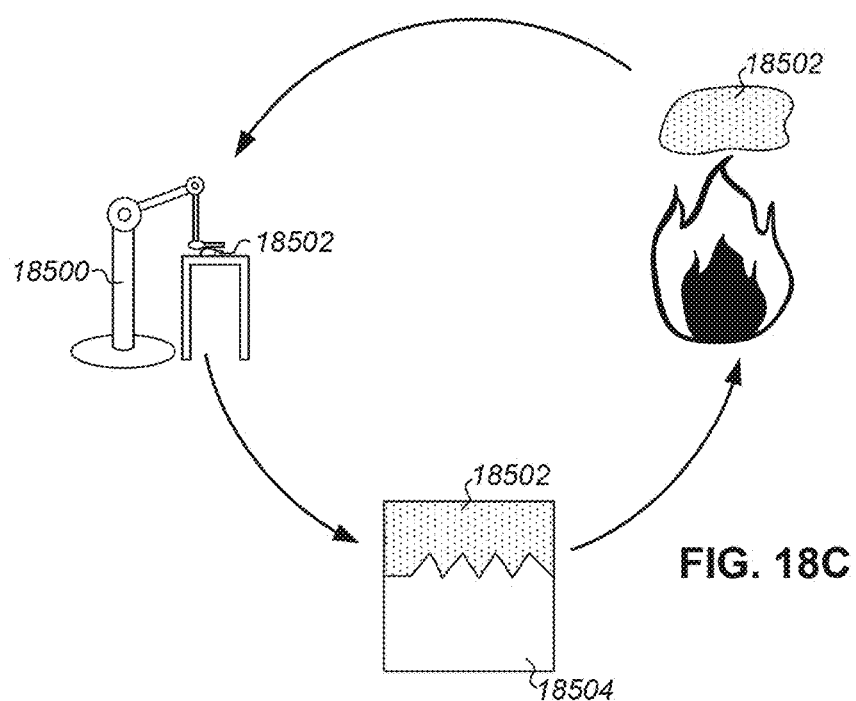
FIGS. 18C-D illustrate additional examples of manufacturing processes for different components of a patient's mask.

For a more efficient method of manufacturing custom components than additive manufacturing, the moulding tools can be rapidly prototyped (e.g., 3D printed). In some examples, rapid three-dimensional printed tooling may provide a cost-effective method of manufacturing low volumes. Soft tools of aluminium and/or thermoplastics are also possible. Soft tools provide a low number of moulded parts and are cost effective compared to steel tools. As shown in FIG. 18C, a machine 18500 may be used to create a soft tool 18502 to mould components 18504. After use, soft tools 18502 may be melted down, recycled and made into a different shape for manufacturing a different custom patient interface.

Hard tooling may also be used during the manufacture of custom components. Hard tooling may be desirable in the event of favourable volumes being produced. Hard tools may be made of various grades of steel or other materials for use during moulding/machining processes. The manufacturing process may also include the use of any combination of rapid prototypes, soft and hard tools to make any of the components of the patient interface. The construction of the tools may also differ within the tool itself, making use of any or all of the types of tooling for example: one half of the tool, which may define more generic features of the part may be made from hard tooling, while the half of the tool defining custom components may be constructed from rapid prototype or soft tooling. Combinations of hard or soft tooling are also possible.

Figure 18D:
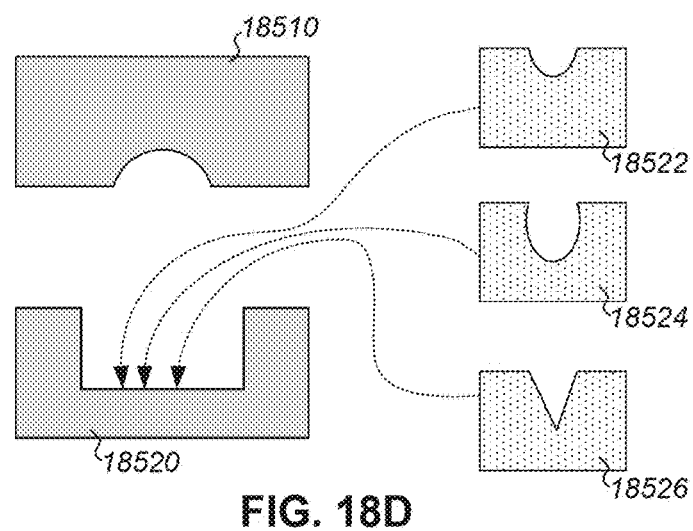

FIG. 18D illustrates an additional example of manufacturing using changeable tool inserts. In this method, a hard steel (or other suitable hard material for injection moulding) tool base is formed. In FIG. 18D, two portions 18510 and 18520 form the hard tool base. Interchangeable tool inserts 18522, 18524, 18526 are formed using, for example, aluminium or 3D printed plastic materials, each insert corresponding to a different patient's needs. Inserts 18522, 18524, 18526 may be customised to each individual patient. Alternatively, multiple inserts may be coupled to the same tool, so that different inserts may control different sections of the patient interface e.g. nose bridge, mouth width, patient interface depth, etc.

Other manufacturing techniques may also include multi-shot injection moulding for patient interfaces having different materials within the same component. For example, a patient interface cushion may include different materials or softness grades of materials at different areas of the patient interface. Thermoforming (e.g., vacuum forming), which involves heating sheets of plastic and vacuuming the sheets onto the tool mould and then cooling the sheets until it takes the shape of the mould may also be used. This is a viable option for moulding components of the custom nare cover. In a yet another form, a material which may be initially malleable may be used to produce a customised patient interface frame (or any other suitable component such as a headgear or portions thereof, such as a rigidizer). A 'male' mould of the patient may be produced using one or more techniques described herewithin, upon which a malleable 'template' component may be placed to shape the component to suit the patient. Then, the customised component may be 'cured' to set the component so that it would no longer be in a malleable state. One example of such a material may be a thermosetting polymer, which is initially malleable until it reaches a particular temperature (after which it is irreversibly cured), or a thermosoftening plastic (also referred to as thermoplastic), which becomes malleable above a particular temperature. Custom fabric weaving/knitting/forming may also be used. This technique is similar to three-dimensional printing processes except with yarn instead of plastic. The structure of the textile component may be knitted into any three-dimensional shapes, which are ideal for fabricating custom headgear.

Table A, below, illustrates some potential component and manufacturing components. It will be understood that these combinations are merely exemplary and that variations of these combinations are possible.

2.11.11 Exemplary Embodiments

Table B, below, illustrates some exemplary embodiments of customised respiratory patient interfaces. Again, it will be understood that these combinations are merely exemplary and that variations of these combinations are possible.

TABLE B

Custom Patient interface Embodiments

| Embodiment | # of Parts | Frame | Intermediate Structure | Sealing Element |
|---|---|---|---|---|
| A | 3 | Custom | Custom | Custom |
| B | 3 | Custom | Custom | Standardised |
| C | 3 | Custom | Standardised | Standardised |
| D | 3 | Custom | Standardised | Custom |
| E | 3 | Standardised | Standardised | Custom |
| F | 3 | Standardised | Custom | Custom |
| G | 3 | Standardised | Custom | Standardised |
| H | 2 | Standardised | Custom | |
| I | 2 | Custom | | Standardised |
| J | 2 | Custom | Standardised | |
| K | 1 | | Custom | |

Figures 19A, 19B, 19C:
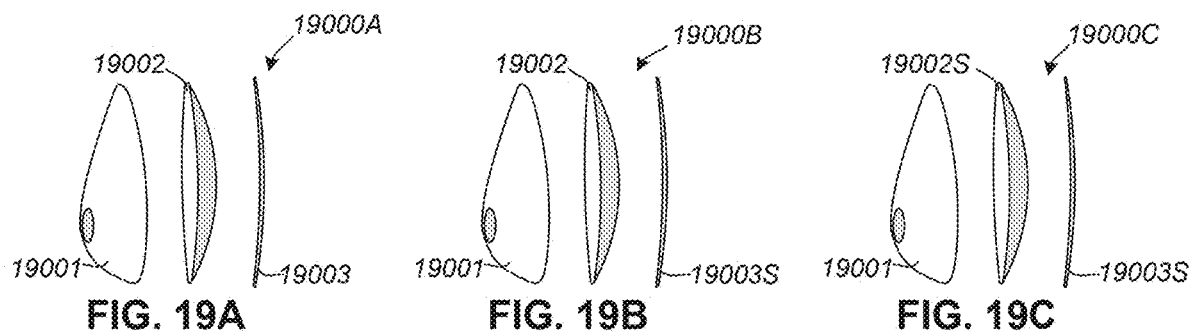
FIGS. 19A-K illustrate several embodiments of customised masks.

Embodiments A-K of Table B correspond to FIGS. 19A-K illustrating patient interfaces 1900A-K. In FIG. 19A, patient interface 19000A includes three customised components, frame 19001, intermediate structure 19002 and sealing element 19003. In this example, frame 19001 is customised based on the patient's facial construct, and modified to maximise comfort and stability while minimising the size of

TABLE A

Component Manufacturing

| Component | Possible Manufacturing Techniques |
|---|---|
| Frame | Machining with laser etching (machining the component from a larger generic moulded dummy patient interface and using laser or chemicals to etch the finer details).<br>SLS/SLA Printing (directly printing the frame component).<br>Rapid tooling (3D printed or aluminium tooling to mould low volumes of components).<br>Interchangeable tool inserts<br>Thermoforming (along with rapid tooling and/or interchangeable tool inserts). |
| Intermediate Structure | Rapid tooling<br>SLS/SLA printing (silicone, TPE or foam printers)<br>Interchangeable tool Inserts<br>Compression cutting (if the Intermediate component comprises of foam or textile materials; cutting knives can be flexible and adjustable to achieve the different shapes, with robotic method of positioning the knives or materials).<br>Multi-shot injection moulding (for different materials within the same component) |
| Sealing Element | SLS/SLA Printing (silicone, TPE or foam printers)<br>Rapid tooling<br>Inter-changeable tool Inserts<br>Compression Cutting (if sealing element comprises a foam or textile, or flocked foam (Bamberg) materials); cutting knives can be flexible and adjustable to achieve the different shapes, with robotic method of positioning the knives or materials.<br>Multi-shot injection moulding |
| Headgear | Compression cutting (custom cut the templates for the headgears; cutting knives may be flexible and adjustable to achieve the different headgear shapes).<br>Custom fabric weaving/knitting/forming (knit out the headgear template with control over the thickness, length and elasticity; form custom shapes by heating the fabrics into a malleable state and them moulded onto tools). | the part. This geometry would be mostly driven by the acquired three-dimensional surface data. Further input into the frame design may come from the user preferences input such as: tube/elbow type and position, vent position/type, colour etc. Intermediate structure 19002 is also customised to provide a customised geometry or material composition that provides some finer tuning to the patient's facial construct both geometrically and interstitially. Customisation of intermediate structure 19002 may be driven by both the 3D surface model and 2D pressure map. Sealing element 19003 is also customised to provide the micro adjustments required to achieve a reliable and comfortable seal. Such finer adjustments may be in an effort to account for the differences between the relaxed and deformed state (e.g., thicker areas of soft material to account for areas of large deflection/movement in use or in areas of discomfort). The data collection techniques and the modification algorithms discussed above may be used to create patient interface 19000A.

Patient interface 19000B of FIG. 19B is generally the same as patient interface 19000A, except that a standard sealing element 19003S is used. In this embodiment sealing element 19003S is a standard thin layer of elastomer, foam, gel and/or tacky material that is easily attached to the intermediate component in such a way that it does not crease/deform in an undesired manner and can be easily cut to each custom shape.

Figures 19D, 19E, 19F:
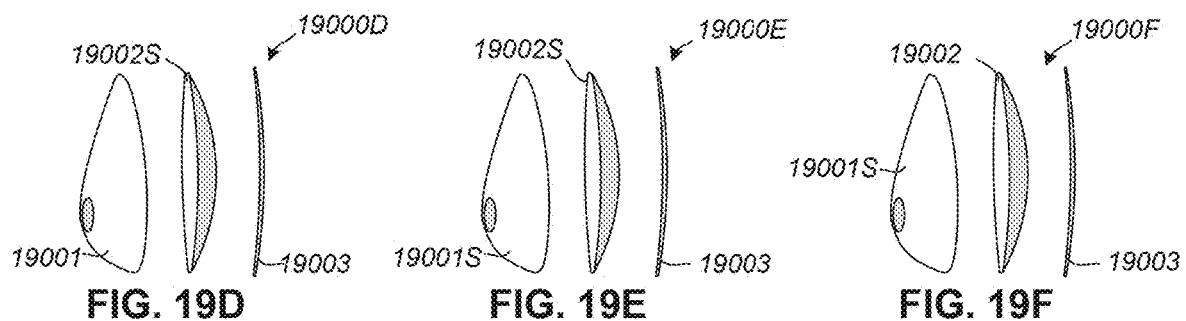

Patient interface 19000C of FIG. 19C is generally the same as patient interface 19000B, except that a standard intermediate structure 19002S is used. In this embodiment, several sizes of standard intermediate components are used that suit different anthropometric ranges to provide the offset and compliance zones, similar to areas found in a conventional patient interface. Patient interface 19000D includes a standardised intermediate structure 19002S with a customised frame 19001 and sealing element 19003 (FIG. 19D). In patient interface 19000E, only sealing element 19003 is customised, while frame 19001S and intermediate structure 19002S are standardised (FIG. 19E). In this embodiment, standardised frame 19001S may consist of one of several available sizes that can interface with one of or all of several sizes of intermediate components 19002S. While, this embodiment refers largely to standardised frame geometry the user may still provide input for venting or colour or tube type/position.

Figure 19G:
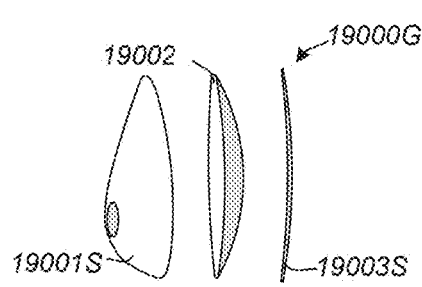
Figure 19H:
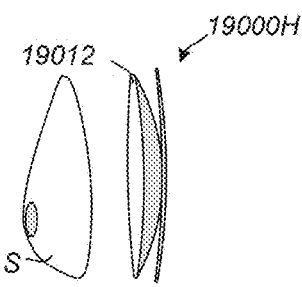
Figure 19I:
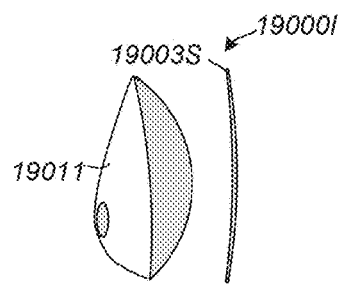

In patient interface 1900F of FIG. 19F, only intermediate structure 19002 is customised, while standardised frame 19001S and sealing element 19003S are provided. Intermediate structure 19002 may provide an area that provides the proper offsetting function, compliance region and customised macro and micro adjustments to suit individual facial geometry, thus enabling a stable and comfortable customised platform to which a sealing layer can be attached. In this example, intermediate structure 19002 and sealing element 19003 may be provided as a single piece to the patient but consist of 2 different materials. The surface of intermediate structure 19002 that interfaces with the standardised frame may have to take a geometry that enables fixation to the frame. This could be achieved by way of a surface blend, from the patient data driven custom surfaces, to the required standard surfaces. In one variation, patient interface 19000G is similar to patient interface 19000F, except that sealing element 19003S is not customised in this embodiment (FIG. 19G). In another variation, patient interface 1900H includes a unitary intermediate structure and sealing element 19012 (FIG. 19H). Unitary intermediate structure and sealing element 19012 may be moulded of a single material or formed of a multi-shot mould of differing materials or through additive manufacturing using single or multiple materials. Thus, unitary intermediate structure and sealing element 19012 is formed as a single component designed and manufactured as one, which then attaches to a standard or pre-existing frame 19001S. Patient interface 19000I provides a customised unitary frame/intermediate structure 19011 with a standardised sealing element 19003S (FIG. 19I).

Figure 19J:
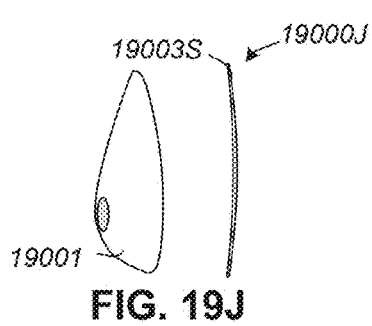
Figure 19K:
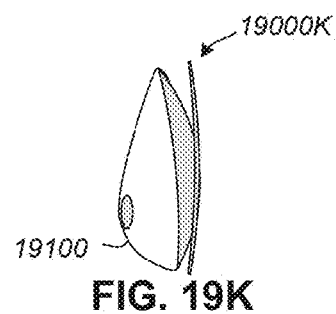

In FIG. 19J, patient interface 19000J is formed having a customised frame 19001 and a standardised sealing element 19003S. This embodiment eliminates an intermediate structure. Instead, the customised frame 19001 functions as both a frame and an intermediate structure. Finally, in FIG. 19K, a fully-customised single component 19100 patient interface 19000K is shown. Single component 19100 may be formed of a single material (e.g., Mirage FX, Nano) or a combination of any of the materials discussed above. In some examples, patient interface 19000K is formed of a single shot of a single material in a custom tool. Alternatively, patient interface 19000K may be produced using multiple materials, using multi-shot injection moulding in a custom tool, or produced directly via rapid manufacturing techniques that include multiple materials with different properties 3D printed using either multi-head FDM or multi-material photopolymer printing or similar.

2.11.12 Distribution 4700

In order to provide the best benefit to the patient and to ensure that adequate sealing is accomplished, for example, between a frame and sealing element as described with respect to a custom nare cover, information relating to a mask may be recorded and stored on a central server. Such information may be entered when a patient opens an online account and creates a patient profile, and include data relating to an initial facial geometry scan, designed custom mask geometry, personal aesthetic preferences or flow generator preferences, and the like. The online account may hold the patient's custom mask information and therefore can act as a platform where the custom mask details like the current patient facial geometry can be updated and also a platform where patients may order more of their custom masks and therefore optimise the benefits of their custom mask, keeping up compliance of that patient with the desirable therapy.

Along with this online account a patient ID number or sequence (e.g., a barcode) may be assigned to the patient. The patient ID number may be labeled onto the custom mask to give the product identification, so that each mask may be traced back to their respective owners for returns, optimisation and the like. For patient purchasing a mask product in person, the ID number or sequence may be scanned and mask components may be ordered in through traditional retail locations or online. In at least some example, the ID number or sequence may include at least one of a barcode sequence, or a symbol (numeric, alphabetical, etc.) that is pad printed, three-dimensional colour printed, or geometrically printed onto a mask component. A radiofrequency ID chip may also be embedded in a mask, which may be three-dimensionally printer-embedded or inserted after manufacturing. Additionally, physical copies of a customised mask component (e.g., a frame) may be stored, and may later be scanned if replenishments are desired.

2.12 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

3 REFERENCE NUMERALS outer chamber 10
patient 1000
bed partner 1100
virtual portal 1400
rpt device 1500
third strap 1514
air circuit 1600
humidifier 1700
nare cover 1700
silicone component 1804
edition published 2011
patient interface 3000
patient interface sealing surface 3100
plenum chamber 3200
headgear system 3300
vent 3400
forehead support 3500
swivel 3510
socket 3520
connection port 3600
iso 3744
asphyxia valve 3800
patient interface customisation method 4000
remote external communication network 4282
local external communication network 4284
remote external device 4286
local external device 4288
display driver 4292
display 4294
patient data collection 4300
step 4300
relaxed state data collection 4301
deformed state data collection 4302
pressure mapping 4303
user input 4304
processing module 4310
pressure compensation algorithm 4312
vent flow rate calculation algorithm 4314
leak flow rate algorithm 4316
respiratory flow rate algorithm 4318
phase determination algorithm 4321
target ventilation determination algorithm 4328
data processing step 4400
post processing step 4401
experienced pressure 4402 specific feature processing 4403
patient preference 4404
output data package 4450
geometric surface model design package 4451
pressure map design package 4452
patient interface design 4500
patient interface design package 4550
manufacturing 4600
distribution 4700
final product 4700
laser scanning system 5000
laser 5001
len 5002
sensor 5003
object 5050
humidifier reservoir 5110
humidifier reservoir dock 5130
temperature sensor 5216
camera 6001
camera 6002
display 6003
patient 6050
data collection system 7000
rod 7001
force sensor 7002
processor 7003
patient's face 7050
cast material 7060
mould 7065
scanner 7070
tooling 7075
rigid deforming device 8001
face deforming device 8001
camera 8002
device 8010
dummy patient interface 8020
pressure film 8021
tactile pressure film sensor 8021
processor 8022
pressure map 8030
patient's skin 8050
nasal bridge 8051
surface 8055
patient 9000
nasian 9003
nasal 9004
philtrum 9005
lip fold 9008
mental eminence 9009
suborbital 9015
inferior malar 9016
lateral nostril 9017
labial ridge 9018
canina 9019
sub canina 9020
nose patient interface 10000
first input 10010
corresponding padding 10012
second input 10020
corresponding gel portion 10022
third input 10030
beard patch 10032
patient 10100
patient 10200
patient's head 10300
patient interface 10401
patient interface 11000
frame 11001
intermediate structure 11002
sealing element 11003
custom sealing element 11003
patient interface frame 12010
custom frame assembly 12020
frame 12030
standardised frame 12040
frame 12041
standardised frame 12042
patient's face 12050
interlock system 12060
customised component 12070
intermediate structure 13010
first component 13012
second component 13014
frame 13040
frame 13042
patient 13050
sealing element 13510
optimal sealing element 13510
sealing element 13511
sealing element 13520
sealing element 13522
patient's face 13550
patient interface 13552
cushion 14102
inner cushion component 14104
outer barrier 14106
chamber 14108
chamber material 14110
rib 14112
optional internal barrier membrane 14512
mask interconnect component 14516
adhesive 14518
optional clip 14520
soft springing foam 14560
elastomer 14562
foam ball 14564
gel 14566
cap portion 14672
mask frame 14690
channel 14692
ridge 14694
gas port 14696
first layer 14802
second layer 14804
layer 14806
bottom end 14902
top end 14904
first layer 14912
second layer 14914
third layer 14916
fourth "hollow" layer 14918
frangible seal 14922
tab 14924
patient interface 15002
headgear 15004
first strap 15010
second strap 15012
third strap 15014
neck attachment 15040
crown attachment 15042
patient 15050
nose bridge anchor point 16002
mouth anchor point 16004
mouth anchor point 16006 ear anchor point 16008
patient 16050
patient interface 16060
sealing element 16062
precise sealing element 16062
structure 16070
compliant joint feature 16080
patient's head 16100
skull 16102
patient's skin 16104
nose 16106
patient interface's associated headgear 16108
patient interface 16110
bed pillow 16120
suborbital 16205
alar angle 16210
nose corner 16215
nose middle 16220
width 16225
second portion 16246
first condition 16300
second condition 16305
patient 16350
headgear 16352
patient interface 16400
conduit 16401
sealing element 16402
headgear 16403
first portion 16404
second portion 16406
patient interface 16410
conduit 16411
sealing element 16412
headgear 16413
crown strap 16414
second portion 16416
buckle 16419
patient interface 16420
conduit 16421
sealing element 16422
headgear 16423
first portion 16424
second portion 16426
wireform 16428
nare cover 17000
delivery conduit 17005
headgear 17010
marker 17100
surface 17102
elliptical position 17120
headgear vector 17130
slot 17135
frame 17200
inner wall 17210
seal receiving surface 17220
aperture 17230
vent hole 17240
rigidizer arm 17250
first end 17252
second end 17254
sealing element 17300
foam layer 17302
adhesive PSA backing 17304
single flat profile 17310
dimensional model 17310
first surface 17350
second surface 17355 large blank component 18010
extra material 18012
custom component 18014
patient 18050
tool 18060
curved cutting edge 18062
material 18070
component 18072
component 18074
component 18076
third layer 18106
machine 18500
soft tool 18502
component 18504
portion 18510
portion 18520
interchangeable tool insert 18522
interchangeable tool insert 18524
interchangeable tool insert 18526
frame 19001
intermediate structure 19002
sealing element 19003
unitary frame/intermediate structure 19011
sealing element 19012
single component 19100
rpt device 40000
external housing 40100
upper portion 40120
portion 40140
panel 40150
chassi 40160
handle 40180
pneumatic block 40200
pneumatic component 41000
air filter 41100
inlet air filter 41120
outlet air filter 41140
inlet muffler 41220
outlet muffler 41240
pressure generator 41400
blower 41420
brushless DC motor 41440
air circuit 41700
air circuit 41710
supplemental oxygen 41800
electrical component 42000
pcba 42020
board Assembly PCBA 42020
power supply 42100
present technology power supply 42100
input device 42200
central controller 42300
clock 42320
therapy device controller 42400
protection circuit 42500
memory 42600
transducer 42700
pressure transducer 42720
flow rate sensor 42740
motor speed transducer 42760
data communication interface 42800
output device 42900
algorithm 43000
therapy engine module 43200
phase determination algorithm 43210
waveform determination 43220
ventilation determination 43230 inspiratory flow limitation determination 43240
apnea/hypopnea determination 43250
snore determination 43260
airway patency determination 43270
target ventilation determination algorithm 43280
target ventilation determination 43280
therapy parameter determination algorithm 43290
therapy control module 43300
method 45000
step 45200
step 45300
step 45400
step 45500
step 45600
humidifier 50000
humidifier outlet 50040
humidifier base 50060
humidifier reservoir 51100
conductive portion 51200
reservoir dock 51300
locking lever 51350
water level indicator 51500
humidifier transducer 52100
air pressure sensor 52120
flow rate transducer 52140
temperature transducer 52160
humidity sensor 52180
heating element 52400
humidifier controller 52500
central humidifier controller 52510
heating element controller 52520
air circuit controller 52540
patient interface 161100
central controller 423000
therapy engine module 432000
elastic inner layer 16417*a*
inner layer 16417*a*
outer layer 16417*b*
location 16A
location 16B
location 16C
patient interface 19000A
patient interface 19000B
patient interface 19000C
patient interface 19000D
patient interface 19000E
patient interface 19000F
patient interface 19000G
patient interface 19000I
patient interface 19000J
patient interface 19000K
standard frame 19001S
standard intermediate structure 19002S
standard sealing element 19003S
patient interface 1900F
patient interface 1900H
first diagonal force T1
second force T2
third force T3

The invention claimed is:

1. A patient interface for delivery of a supply of pressurised air or breathable gas to an entrance to the patient's airways comprising:
 a frame assembly having walls and configured to be disposed over nares of the patient and extending along a generally elliptical path that covers outer peripheries of the nares including alar sidewalls and a portion of a columella of the patient, the frame assembly defining a plenum chamber between its walls and the patient's skin; and
 a sealing element capable of forming a seal against skin that surrounds both nares of the patient without being partially located inside the patient's nose, the sealing element being less rigid than the frame assembly and having an adhesive on at least one side of the sealing element, the sealing element being coupleable to an anterior wall of the frame assembly.

2. The patient interface of claim 1, wherein the sealing element includes a foam layer laminated onto a pressure-sensitive adhesive layer.

3. The patient interface of claim 1, wherein the sealing element includes an adhesive on a patient-contacting side.

4. The patient interface of claim 1, wherein the sealing element includes an adhesive on both a patient-contacting side and a frame contacting side.

5. The patient interface of claim 1, wherein the frame assembly includes a plurality of vent holes.

6. The patient interface of claim 5, wherein the plurality of vent holes includes a number of vent holes that are proportional to a measure of dead space.

7. The patient interface of claim 5, wherein the number of the plurality of vent holes is based on dead space defined by the plenum chamber.

8. The patient interface of claim 1, wherein the frame assembly includes a plurality of slots for accepting rigidizer arms that couple with a headgear.

9. The patient interface of claim 1, wherein the plenum chamber has a volume that is approximately a multiplier between 1 to 2 times of the patient's nose.

10. A patient interface for sealed delivery of a flow of air at a continuously positive pressure with respect to ambient air pressure to an entrance to the patient's airways comprising:
 a mask assembly;
 a sealing element coupleable to the mask assembly and in contact with the patient's face; and
 a positioning and stabilising structure, coupled to the mask assembly, the positioning and stabilising structure being configured to maintain the sealing element in sealing contact with an area surrounding an entrance to the patient's airways while maintaining a therapeutic pressure at the entrance to the patient's airways;
 wherein at least one of the mask assembly, the sealing element and the positioning and stabilising structure is configured to compensate for skin movement and deformation.

11. The patient interface of claim 10, wherein the positioning and stabilising structure is configured to compensate for longitudinal skin sheer of between approximately 1 mm and approximately 50 mm with respect to a longitudinal axis of the patient's face.

12. The patient interface of claim 10, wherein the positioning and stabilising structure is configured to compensate for lateral skin sheer of between approximately 1 mm and approximately 30 mm with respect to a longitudinal axis of the patient's face.

13. The patient interface of claim 10, wherein the positioning and stabilising structure is configured to compensate for nare angle deflection of between approximately 1 degree and 30 degrees.

14. The patient interface of claim 10, wherein the positioning and stabilising structure is configured to compensate for an upward movement of corners and middle of a nose of a maximum of approximately 9 mm and approximately 4 mm, respectively.

15. The patient interface of claim 10, wherein the positioning and stabilising structure is configured to compensate for an increase in a width of the patient's nose of between approximately 1 mm and approximately 4 mm.

16. The patient interface of claim 10, wherein the positioning and stabilising structure is configured to compensate for a cheek bulge from a first condition to a second condition, the first condition and second condition being spaced by between approximately 1 mm and 10 mm.

17. The patient interface of claim 10, wherein the positioning and stabilising structure includes a first portion and a second portion, the first portion and the second portion being configured to compensate for perturbations such that the sealing element remains in contact with the patient's face when a force of up to 10 Newtons is applied to a portion of the positioning and stabilising structure.

18. The patient interface of claim 17, wherein the first portion is formed of a non-elastic material and the second portion is formed of an elastic material.

19. The patient interface of claim 10, wherein the positioning and stabilising structure includes a first portion and a second portion, at least one of the first portion and the second portion having an elastic material configured to compensate for perturbations such that the sealing element remains in contact with the patient's face when a force of up to 10 Newtons is applied to the positioning and stabilising structure.

20. The patient interface of claim 10, wherein the positioning and stabilising structure includes a first portion, a second portion, and a path portion coupled to the first portion and coextensive with the second portion, the second portion being capable of translation along the path portion.

21. The patient interface of claim 20 wherein the path portion comprises a wireframe.

22. The patient interface of claim 20, wherein the skin movement and deformation is characterized as sheering and deflection properties in relation to patient's facial features.

* * * * *